(12) United States Patent
Gupta et al.

(10) Patent No.: US 8,067,208 B2
(45) Date of Patent: *Nov. 29, 2011

(54) PROBES AND METHODS FOR HEPATITIS C VIRUS TYPING USING MULTIDIMENSIONAL PROBE ANALYSIS

(75) Inventors: Amar P. Gupta, Danville, CA (US); Stephen Gordon Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 11/474,092

(22) Filed: Jun. 23, 2006

(65) Prior Publication Data

US 2007/0141560 A1    Jun. 21, 2007

Related U.S. Application Data

(60) Provisional application No. 60/695,991, filed on Jun. 30, 2005, provisional application No. 60/696,253, filed on Jun. 30, 2005, provisional application No. 60/696,293, filed on Jun. 30, 2005, provisional application No. 60/696,303, filed on Jun. 30, 2005.

(51) Int. Cl.
*C12P 19/34* (2006.01)
*C12Q 1/68* (2006.01)

(52) U.S. Cl. ........................ 435/91.2; 435/6.1
(58) Field of Classification Search .................. 435/91.2
See application file for complete search history.

(56) References Cited

U.S. PATENT DOCUMENTS

| | | | | | |
|---|---|---|---|---|---|
| 5,837,442 | A | * | 11/1998 | Tsang | 435/5 |
| 5,846,704 | A | * | 12/1998 | Maertens et al. | 435/5 |
| 6,472,156 | B1 | * | 10/2002 | Wittwer et al. | 435/6 |
| 2002/0106638 | A1 | | 8/2002 | Maertens et al. | |
| 2003/0054372 | A1 | * | 3/2003 | Jaeger | 435/6 |
| 2004/0005613 | A1 | * | 1/2004 | Norton | 435/6 |
| 2004/0072761 | A1 | * | 4/2004 | Campbell et al. | 514/18 |

FOREIGN PATENT DOCUMENTS

| | | |
|---|---|---|
| EP | 0 787 807 A2 | 8/1997 |
| EP | 06013294.1 | 6/2007 |
| JP | 2002272475 | 9/2002 |
| JP | 2002345467 | 12/2002 |
| WO | WO 99/28500 A1 | 6/1999 |
| WO | WO 01/48234 A2 | 7/2001 |
| WO | WO 03/040367 A1 | 5/2003 |
| WO | WO 2004/014313 A2 | 2/2004 |
| WO | WO 2004/044182 A2 | 5/2004 |
| WO | WO 2004/074447 A2 | 9/2004 |
| WO | WO 2005/028650 A2 | 3/2005 |

OTHER PUBLICATIONS

Maliwal et al. Biopolymers, vol. 35, pp. 245-255, 1995.*
Bullock, G., 2002, Hepatitis C Genotype Determination by melting Curve analysis with a single set of fluorescence resonance energy transfer probes, *Clinical Chemistry*, 48 (12): 2147-2154.
Harris, K., et al. 2001, Diversity of Hepatitis C Virus Quasispecies evaluated by denaturing gradient gel electrophoresis, *Clinical and Diagnostic Laboratory Immunology*, 8 (1): 62-73.
Schröter, M., et al., 2002, Genotyping of Hepatitis C Virus Types 1, 2, 3, and 4 by a One-Step LightCycler Method Using Three Difference Pairs of Hybridization Probes, *Journal of Clinical Microbiology*, 40 (6): 2046-2266.
Stuyver, L., et al., 1996, Second-Generation Line Probe Assay for Hepatitis C Virus Genotyping, *Journal of Clinical Microbiology*, 34 (9): 2046-2266.
Lin, Zhili, et al., 2004, "A high throughput Beta-globin genotyping method by multiplexed melting temperature analysis", Molecular Genetics and Metabolism, 81:237-243.

* cited by examiner

*Primary Examiner* — Gary Benzion
*Assistant Examiner* — Cynthia Wilder
(74) *Attorney, Agent, or Firm* — David J. Chang; Rhea C. Nersesian; Vivien M. Banholzer

(57) ABSTRACT

This invention provides compositions and methods for HCV typing, e.g., genotyping and/or subtyping. The compositions and methods of the invention can be used to assign an HCV isolate to one of at least five HCV types (for example, selected from types 1, 2, 3, 4, 5 or 6), or to one of at least five subtypes (for example, subtypes 1*a/b/c*, 2*a/c*, 2*b*, 3*a*, 4*a*, 5*a* or 6*a*). These methods integrate the hybridization data from a plurality of HCV typing probes in a multidimensional analysis to make an HCV type assignment for an HCV in an experimental sample. The invention also provides related compositions, including, for example, the HCV typing probes and HCV typing diagnostic kits.

26 Claims, 32 Drawing Sheets

| Genomic Heterogeneity Terminology | Definition | Percent Nucleotide Sequence Identity Over the Full HCV Genome |
|---|---|---|
| Genotype | Genetic heterogeneity among different HCV isolates | 65.7–68.9 % |
| Subtype | Closely related isolates within each of the major genotypes | 76.9–80.1 % |
| Quasispecies | Complex of genetic variants within individual isolates | 90.8–99 % |

FIG. 2

| Subtype | Percent nucleotide identity with a 222-nucleotide segment derived from the NS5 region at positions 7975 to 8196 of the prototype HCV viral genome ||||||||||||
| | 1a | 1b | 1c | 2a | 2b | 2c | 3a | 3b | 4a | 5a | 6a |
| --- | --- | --- | --- | --- | --- | --- | --- | --- | --- | --- | --- |
| 1a | 100 | 81 | 85 | 65 | 66 | 63 | 67 | 66 | 68 | 69 | 64 |
| 1b | | 100 | 77 | 64 | 67 | 64 | 67 | 71 | 64 | 70 | 65 |
| 1c | | | 100 | 68 | 70 | 67 | 65 | 70 | 64 | 61 | 61 |
| 2a | | | | 100 | 82 | 77 | 67 | 67 | 66 | 66 | 68 |
| 2b | | | | | 100 | 81 | 64 | 69 | 65 | 67 | 66 |
| 2c | | | | | | 100 | 64 | 65 | 65 | 66 | 65 |
| 3a | | | | | | | 100 | 79 | 65 | 67 | 64 |
| 3b | | | | | | | | 100 | 66 | 68 | 61 |
| 4a | | | | | | | | | 100 | 66 | 66 |
| 5a | | | | | | | | | | 100 | 68 |
| 6a | | | | | | | | | | | 100 |

FIG. 3

| HCV Genotype/Subtype | Known Isolates |
|---|---|
| 1a | HCV-1, HCV-H, HC-J1 |
| 1b | HCV-J, HCV-BK, HCV-JT |
| 1c | HC-G9, Td-6, YS-117 |
| 2a | HC-J6, HC-J5, HCV-K2a |
| 2b | HC-J8, HC-J7, HCV-K2b |
| 2c | CH114, S83, T-983 |
| 3a | NZL1, E-b1, BR36, K3a/650, HCV-K3a, T-1, T-7 |
| 3b | NE137, HCV-Tr, T9, MN6, T-10 |
| 4a | GB809-4, Z4, Z8, Z5, Syr1, Syr2, N5, Cam600, Z1, N1, N2, DK13 |
| 5a | BE95, SA1, SA-7 |
| 6a | VN11, HK2, HK-2, VN506 |

FIG. 4

| HCV Type | 5'-UTR Consensus Base Sequence | SEQ ID NO: |
|---|---|---|
| 1a/1b/1c | TGAGTACACC GGAATTGCCA GGACGACCGG GTC | 1 |
| 2a/2c | ---------- ---------- ----G----A- ---T--- --- | 2 |
| 2b | ---------- ---------- ----A--G -A-A- ---T--- --- | 3 |
| 3a | ---------- ---------- ----C--TG --GT- --- --- | 4 |
| 4a | ---------- ---------- ----C------G ---T--- --- | 5 |
| 5a | ---------- ---------- ---------G- ---T--- --- | 6 |
| 6a | ---------- ---------- ---------- ---T--- --- | 7 |
| 2a variant quasispecies | ---------- ---------- ------TG --A- ---T--- --- | 8 |

FIG. 5

| Probes | Length (nt) | Base sequence | SEQ ID NO: |
|---|---|---|---|
| AG0203A | 21 | FCGGAATTGCCAGGACGACCGG | 9 |
| AG0203A-FAM | 21 | FCGGAATTGCCAGGACGACCGGP | 10 |
| AG0203A_HEX | 21 | HCGGAATTGCCAGGACGACCGGP | 11 |
| AG0203A_JA | 21 | WCGGAATTGCCAGGACGACCGGP | 12 |
| AG0203A_ET | 21 | WFCGGAATTGCCAGGACGACCGGP | 13 |
| AG0303A | 21 | CGGAATTGCCAGGACGACCGG | 14 |
| AG0303B | 21 | FJCGGAATTGCCAGGACGACCGG | 15 |
| AG0403B | 21 | FVMKKBBMVVKMKVVMMP | 16 |
| AG0503A | 22 | FCCGGAATTGCCAGGACGACCGG | 17 |
| AG0503B | 23 | FACCGGAATTGCCAGGACGACCGG | 18 |
| AG0503D | 24 | FCACCGGAATTGCCAGGACGACCGG | 19 |
| AG0503E | 22 | FCGGAATTGCCAGGACGACCGGG | 20 |
| AG0503F | 23 | FCGGAATTGCCAGGACGACCGGGT | 21 |
| AG0503G | 24 | FCGGAATTGCCAGGACGACCGGGTC | 22 |
| AG0503H | 23 | FCCGGAATTGCCAGGACGACCGGG | 23 |
| AG0303A-SYBR | 21 | CGGAATTGCCAGGACGACCGG | 24 |
| AG0307D | 22 | FDGGAASSGDDAGGADGADDGGP | 25 |
| AG0307M | 22 | FCGGAATTGCCAGGACGACCGGGP | 26 |
| AG0307N | 22 | FDGGAASSGDDAGGADGADDGGGP | 27 |
| AG0308A | 20 | FDGGAASSGDDAGGADGADDGP | 28 |
| AG0308B | 19 | FDGGAASSGDDAGGADGADDP | 29 |
| AG0308F | 25 | FGTACACCGGAATTGCCAGGACGACCP | 30 |
| AG0308L | 24 | FGTACACCGGAATTGCCAGGACGACP | 31 |
| AG0308M | 23 | FGTACACCGGAATTGCCAGGACGAP | 32 |
| AG0308N | 22 | FGTACACCGGAATTGCCAGGACGP | 33 |
| AG0308P | 24 | FTACACCGGAATTGCCAGGACGACCP | 34 |
| AG0308Q | 23 | FACACCGGAATTGCCAGGACGACCP | 35 |
| AG0308R | 22 | FCACCGGAATTGCCAGGACGACCP | 36 |
| AG0308S | 23 | FTACACCGGAATTGCCAGGACGACP | 37 |
| AG0308T | 26 | FAGTACACCGGAATTGCCAGGACGACCP | 38 |

FIG. 6

| Probes | length (nt) | Base sequence | SEQ ID NO: |
|---|---|---|---|
| AG0308U | 27 | FGAGTACACCGGAATTGCCAGGACGACCP | 39 |
| AG0308V | 28 | FTGAGTACACCGGAATTGCCAGGACGACCP | 40 |
| AG0308W | 26 | FGTACACCGGAATTGCCAGGACGACCGP | 41 |
| AG0308X | 27 | FGTACACCGGAATTGCCAGGACGACCGGP | 42 |
| AG0308Y | 28 | FGTACACCGGAATTGCCAGGACGACCGGGP | 43 |
| AG0308Z | 27 | FAGTACACCGGAATTGCCAGGACGACCGP | 44 |
| AG0308AB | 25 | FAGTACACCGGAATTGCCAGGACGACP | 45 |
| AG0308AC | 25 | FGAGTACACCGGAATTGCCAGGACGAP | 46 |
| AG0308AD | 25 | FTGAGTACACCGGAATTGCCAGGACGP | 47 |
| AG0308C | 21 | FCGGAATTGCCAGGATGACCGGP | 48 |
| AG0308D | 21 | FCGGAATTGCCGGGACGACCGGP | 49 |
| AG0308E | 21 | FCGGAATTGCCGGGATGACCGGP | 50 |
| AG0308H-FAM | 21 | FCGGAATCGCCGGGATGACCGGP | 51 |
| AG0308H-HEX | 21 | HCGGAATCGCCGGGATGACCGGP | 52 |
| AG0308J | 21 | HCGGAATTGCTGGGAAGACTGGP | 53 |
| AG0308K | 21 | HCGGAATCGCTGGGGTGACTGGP | 54 |
| AG0308G (FAM) | 21 | FCCCGCAAGACTGCTAGCCGAGP | 55 |
| AG0308G (HEX) | 21 | HCCCGCAAGACTGCTAGCCGAGP | 56 |
| AG0308AA | 30 | FTTCTTGGATCAACCCGCTCAATGCCTGGAGP | 57 |

F=6-carboxy-fluorescein (FAM)
H=2', 4, 4', 5', 7, 7'-hexachlorofluorescein (HEX)
W=JA270 rhodamine derivative (see, US Patent No. 6,184,379, issued Feb. 6, 2001, to Josel *et al.*)
P=3'-terminal phosphate group/enzymatically blocked
J=acridine
S=5-propynyl-dU
D=5-Me-dC
B=2'-O-methyl-U
K=2'-O-methyl-rA
M=2'-O-methyl-rG
V=2'-O-methyl-rC

FIG. 6 (cont.)

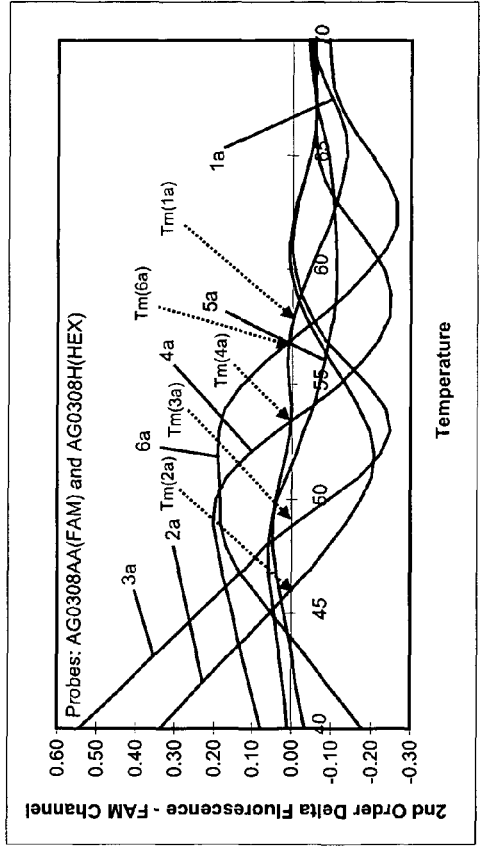
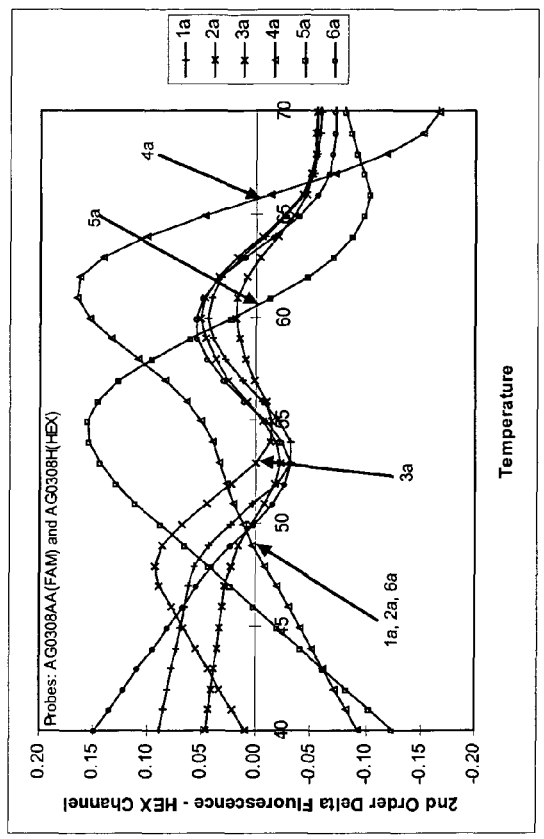
Second Derivative Plots
FAM CHANNEL AG0308AA
HEX CHANNEL AG0308H
FIG. 25

SEQUENCE LISTING

<160> NUMBER OF SEQ ID NOS: 60

<210> SEQ ID NO 1
<211> LENGTH: 33
<212> TYPE: DNA
<213> ORGANISM: hepatitis C virus

<400> SEQUENCE: 1
tgagtacacc ggaattgcca ggacgaccgg gtc    33

<210> SEQ ID NO 2
<211> LENGTH: 33
<212> TYPE: DNA
<213> ORGANISM: hepatitis C virus

<400> SEQUENCE: 2
tgagtacacc ggaattgccg ggaagactgg gtc    33

<210> SEQ ID NO 3
<211> LENGTH: 33
<212> TYPE: DNA

```
<213> ORGANISM: hepatitis C virus

<400> SEQUENCE: 3
tgagtacacc ggaattaccg gaaagactgg gtc                                   33

<210> SEQ ID NO 4
<211> LENGTH: 33
<212> TYPE: DNA
<213> ORGANISM: hepatitis C virus

<400> SEQUENCE: 4
tgagtacacc ggaatcgctg gggtgaccgg gtc                                   33

<210> SEQ ID NO 5
<211> LENGTH: 33
<212> TYPE: DNA
<213> ORGANISM: hepatitis C virus

<400> SEQUENCE: 5
tgagtacacc ggaatcgccg ggatgaccgg gtc                                   33

<210> SEQ ID NO 6
<211> LENGTH: 33
<212> TYPE: DNA
<213> ORGANISM: hepatitis C virus

<400> SEQUENCE: 6
tgagtacacc ggaattgccg ggatgaccgg gtc                                   33

<210> SEQ ID NO 7
<211> LENGTH: 33
<212> TYPE: DNA
<213> ORGANISM: hepatitis C virus

<400> SEQUENCE: 7
tgagtacacc ggaattgcca ggatgaccgg gtc                                   33

<210> SEQ ID NO 8
<211> LENGTH: 33
<212> TYPE: DNA
<213> ORGANISM: hepatitis C virus

<400> SEQUENCE: 8
tgagtacacc ggaattgctg ggaagactgg gtc                                   33

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 9
nggaattgcc aggacgaccg g                                                21

<210> SEQ ID NO 10
<211> LENGTH: 21
<212> TYPE: DNA
<213> ORGANISM: Artificial
<220> FEATURE:
<223> OTHER INFORMATION: Synthetic oligonucleotide probe
```

```
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 10
nggaattgcc aggacgaccg n                                              21

<210> SEQ ID NO 11
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 3',4,4',5',7,7'-
      hexachlorofluorescein (HEX)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 11
nggaattgcc aggacgaccg n                                              21

<210> SEQ ID NO 12
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with JA270
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 12
nggaattgcc aggacgaccg n                                              21

<210> SEQ ID NO 13
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM) and JA270
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 13
nggaattgcc aggacgaccg n                                              21
```

```
<210> SEQ ID NO 14
<211> LENGTH: 21
<212> TYPE: DNA
<213> ORGANISM: Artificial
<220> FEATURE:
<223> OTHER INFORMATION: Synthetic oligonucleotide probe

<400> SEQUENCE: 14
cggaattgcc aggacgaccg g                                              21

<210> SEQ ID NO 15
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with acridine and 6-carboxy-
      fluorescein (FAM)

<400> SEQUENCE: 15
nggaattgcc aggacgaccg g                                              21

<210> SEQ ID NO 16
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is 2'-O-methyl-rC modified with 6-carboxy-
      fluorescein (FAM)
<220> FEATURE:
<221> NAME/KEY: misc_feature
<222> LOCATION: (2)..(3)
<223> OTHER INFORMATION: n is 2'-O-methyl-rG
<220> FEATURE:
<221> NAME/KEY: misc_feature
<222> LOCATION: (4)..(5)
<223> OTHER INFORMATION: n is 2'-O-methyl-rA
<220> FEATURE:
<221> NAME/KEY: misc_feature
<222> LOCATION: (6)..(7)
<223> OTHER INFORMATION: n is 2'-O-methyl-U
<220> FEATURE:
<221> NAME/KEY: misc_feature
<222> LOCATION: (8)..(8)
<223> OTHER INFORMATION: n is 2'-O-methyl-rG
<220> FEATURE:
<221> NAME/KEY: misc_feature
<222> LOCATION: (9)..(10)
<223> OTHER INFORMATION: n is 2'-O-methyl-rC
<220> FEATURE:
<221> NAME/KEY: misc_feature
<222> LOCATION: (11)..(11)
<223> OTHER INFORMATION: n is 2'-O-methyl-rA
<220> FEATURE:
<221> NAME/KEY: misc_feature
<222> LOCATION: (12)..(13)
<223> OTHER INFORMATION: n is 2'-O-methyl-rG
<220> FEATURE:
<221> NAME/KEY: misc_feature
<222> LOCATION: (14)..(14)
<223> OTHER INFORMATION: n is 2'-O-methyl-rA
<220> FEATURE:
<221> NAME/KEY: misc_feature
<222> LOCATION: (15)..(15)
<223> OTHER INFORMATION: n is 2'-O-methyl-rC
<220> FEATURE:
<221> NAME/KEY: misc_feature
<222> LOCATION: (16)..(16)
```

```
<223> OTHER INFORMATION: n is 2'-O-methyl-rG
<220> FEATURE:
<221> NAME/KEY: misc_feature
<222> LOCATION: (17)..(17)
<223> OTHER INFORMATION: n is 2'-O-methyl-rA
<220> FEATURE:
<221> NAME/KEY: misc_feature
<222> LOCATION: (18)..(19)
<223> OTHER INFORMATION: n is 2'-O-methyl-rC
<220> FEATURE:
<221> NAME/KEY: misc_feature
<222> LOCATION: (20)..(20)
<223> OTHER INFORMATION: n is 2'-O-methyl-rG
<220> FEATURE:
<221> NAME/KEY: misc_feature
<222> LOCATION: (21)..(21)
<223> OTHER INFORMATION: n is 2'-O-methyl-rG modified with 3'-terminal
      phosphate

<400> SEQUENCE: 16
nnnnnnnnnn nnnnnnnnnn n                                              21

<210> SEQ ID NO 17
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 17
ncggaattgc caggacgacc gg                                             22

<210> SEQ ID NO 18
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: dA modified with 6-carboxy-fluorescein (FAM)

<400> SEQUENCE: 18
nccggaattg ccaggacgac cgg                                            23

<210> SEQ ID NO 19
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 19
naccggaatt gccaggacga ccgg                                           24

<210> SEQ ID NO 20
<211> LENGTH: 22
<212> TYPE: DNA
<213> ORGANISM: Artificial
<220> FEATURE:
<223> OTHER INFORMATION: Synthetic oligonucleotide probe
```

-continued

```
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 20
nggaattgcc aggacgaccg gg                                              22

<210> SEQ ID NO 21
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 21
nggaattgcc aggacgaccg ggt                                             23

<210> SEQ ID NO 22
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 22
nggaattgcc aggacgaccg ggtc                                            24

<210> SEQ ID NO 23
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)

<400> SEQUENCE: 23
ncggaattgc caggacgacc ggg                                             23

<210> SEQ ID NO 24
<211> LENGTH: 21
<212> TYPE: DNA
<213> ORGANISM: Artificial
<220> FEATURE:
<223> OTHER INFORMATION: Synthetic oligonucleotide probe

<400> SEQUENCE: 24
cggaattgcc aggacgaccg g                                               21

<210> SEQ ID NO 25
<211> LENGTH: 21
<212> TYPE: DNA
<213> ORGANISM: Artificial
<220> FEATURE:
<223> OTHER INFORMATION: Synthetic oligonucleotide probe
```

```
<220> FEATURE:
<221> NAME/KEY: misc_feature
<222> LOCATION: (1)..(1)
<223> OTHER INFORMATION: n is 5-Me-dC modified with 6-carboxy-
      fluorescein (FAM)
<220> FEATURE:
<221> NAME/KEY: misc_feature
<222> LOCATION: (6)..(7)
<223> OTHER INFORMATION: n is 5-propynyl-dU
<220> FEATURE:
<221> NAME/KEY: misc_feature
<222> LOCATION: (9)..(10)
<223> OTHER INFORMATION: n is 5-Me-dC
<220> FEATURE:
<221> NAME/KEY: misc_feature
<222> LOCATION: (15)..(15)
<223> OTHER INFORMATION: n is 5-Me-dC
<220> FEATURE:
<221> NAME/KEY: misc_feature
<222> LOCATION: (18)..(19)
<223> OTHER INFORMATION: n is 5-Me-dC
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 25
nggaanngnn agganganng n                                            21

<210> SEQ ID NO 26
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (22)..(22)
<223> OTHER INFORMATION: n is dG modified with 3'-terminal phosphate
      group

<400> SEQUENCE: 26
nggaattgcc aggacgaccg gn                                           22

<210> SEQ ID NO 27
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is 5-Me-dC modified with 6-carboxy-
      fluorescein (FAM)
<220> FEATURE:
<221> NAME/KEY: misc_feature
<222> LOCATION: (6)..(7)
<223> OTHER INFORMATION: n is 5-propynyl-dU
<220> FEATURE:
<221> NAME/KEY: misc_feature
<222> LOCATION: (9)..(10)
<223> OTHER INFORMATION: n is 5-Me-dC
<220> FEATURE:
<221> NAME/KEY: misc_feature
<222> LOCATION: (15)..(15)
<223> OTHER INFORMATION: n is 5-Me-dC
<220> FEATURE:
<221> NAME/KEY: misc_feature
<222> LOCATION: (18)..(19)
```

```
<223> OTHER INFORMATION: n is 5-Me-dC
<220> FEATURE:
<221> NAME/KEY: misc_feature
<222> LOCATION: (22)..(22)
<223> OTHER INFORMATION: n is dG modified with 3'-terminal phosphate

<400> SEQUENCE: 27
nggaanngnn aggganganng gn                                            22

<210> SEQ ID NO 28
<211> LENGTH: 20
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is 5-Me-dC modified with 6-carboxy-
      fluorescein (FAM)
<220> FEATURE:
<221> NAME/KEY: misc_feature
<222> LOCATION: (6)..(7)
<223> OTHER INFORMATION: n is 5-propynyl-dU
<220> FEATURE:
<221> NAME/KEY: misc_feature
<222> LOCATION: (9)..(10)
<223> OTHER INFORMATION: n is 5-Me-dC
<220> FEATURE:
<221> NAME/KEY: misc_feature
<222> LOCATION: (15)..(15)
<223> OTHER INFORMATION: n is 5-Me-dC
<220> FEATURE:
<221> NAME/KEY: misc_feature
<222> LOCATION: (18)..(19)
<223> OTHER INFORMATION: n is 5-Me-dC
<220> FEATURE:
<221> NAME/KEY: misc_feature
<222> LOCATION: (20)..(20)
<223> OTHER INFORMATION: n is dG modified with 3'-terminal phosphate

<400> SEQUENCE: 28
nggaanngnn aggangannn                                                20

<210> SEQ ID NO 29
<211> LENGTH: 19
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is 5-Me-dC modified with 6-carboxy-
      fluorescein (FAM)
<220> FEATURE:
<221> NAME/KEY: misc_feature
<222> LOCATION: (6)..(7)
<223> OTHER INFORMATION: n is 5-propynyl-dU
<220> FEATURE:
<221> NAME/KEY: misc_feature
<222> LOCATION: (9)..(10)
<223> OTHER INFORMATION: n is 5-Me-dC
<220> FEATURE:
<221> NAME/KEY: misc_feature
<222> LOCATION: (15)..(15)
<223> OTHER INFORMATION: n is 5-Me-dC
<220> FEATURE:
<221> NAME/KEY: misc_feature
<222> LOCATION: (18)..(18)
<223> OTHER INFORMATION: n is 5-Me-dC
<220> FEATURE:
<221> NAME/KEY: misc_feature
<222> LOCATION: (19)..(19)
<223> OTHER INFORMATION: n is 5-Me-dC modified with 3'-terminal
      phosphate
```

-continued

<400> SEQUENCE: 29
nggaanngnn aggangann                                                    19

<210> SEQ ID NO 30
<211> LENGTH: 25
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (25)..(25)
<223> OTHER INFORMATION: n is dC modified with 3'-terminal phosphate
      group

<400> SEQUENCE: 30
ntacaccgga attgccagga cgacn                                             25

<210> SEQ ID NO 31
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (24)..(24)
<223> OTHER INFORMATION: n is dC modified with 3'-terminal phosphate
      group

<400> SEQUENCE: 31
ntacaccgga attgccagga cgan                                              24

<210> SEQ ID NO 32
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (23)..(23)
<223> OTHER INFORMATION: n is dA modified with 3'-terminal phosphate
      group

<400> SEQUENCE: 32
ntacaccgga attgccagga cgn                                               23

<210> SEQ ID NO 33
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature -continued

```
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (22)..(22)
<223> OTHER INFORMATION: n is dG modified with 3'-terminal phosphate
      group

<400> SEQUENCE: 33
ntacaccgga attgccagga cn                                              22

<210> SEQ ID NO 34
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with 6-carboxy-fluorescein
      (FAM)
<220> FEATURE:
<221> NAME/KEY: misc_feature
<222> LOCATION: (24)..(24)
<223> OTHER INFORMATION: n is dC modified with 3'-terminal phosphate
      group

<400> SEQUENCE: 34
nacaccggaa ttgccaggac gacn                                            24

<210> SEQ ID NO 35
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dA modified with 6-carboxy-fluorescein
      (FAM)
<220> FEATURE:
<221> NAME/KEY: misc_feature
<222> LOCATION: (23)..(23)
<223> OTHER INFORMATION: n is dC modified with 3'-terminal phosphate
      group

<400> SEQUENCE: 35
ncaccggaat tgccaggacg acn                                             23

<210> SEQ ID NO 36
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (22)..(22)
<223> OTHER INFORMATION: n is dC modified with 3'-terminal phosphate
      group

<400> SEQUENCE: 36
naccggaatt gccaggacga cn                                              22
```

```
<210> SEQ ID NO 37
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with 6-carboxy-fluorescein
      (FAM)
<220> FEATURE:
<221> NAME/KEY: misc_feature
<222> LOCATION: (23)..(23)
<223> OTHER INFORMATION: n is dC modified with 3'-terminal phosphate
      group

<400> SEQUENCE: 37
nacaccggaa ttgccaggac gan                                          23

<210> SEQ ID NO 38
<211> LENGTH: 26
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dA modified with 6-carboxy-fluorescein
      (FAM)
<220> FEATURE:
<221> NAME/KEY: misc_feature
<222> LOCATION: (26)..(26)
<223> OTHER INFORMATION: n is dC modified with 3'-terminal phosphate

<400> SEQUENCE: 38
ngtacaccgg aattgccagg acgacn                                       26

<210> SEQ ID NO 39
<211> LENGTH: 27
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (27)..(27)
<223> OTHER INFORMATION: n is dC modified with 3'-terminal phosphate
      group

<400> SEQUENCE: 39
nagtacaccg gaattgccag gacgacn                                      27

<210> SEQ ID NO 40
<211> LENGTH: 28
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with 6-carboxy-fluorescein
      (FAM)
<220> FEATURE:
<221> NAME/KEY: misc_feature
<222> LOCATION: (28)..(28)
<223> OTHER INFORMATION: n is dC modified with 3'-termial phosphate
```

-continued

```
      group

<400> SEQUENCE: 40
ngagtacacc ggaattgcca ggacgacn                                           28

<210> SEQ ID NO 41
<211> LENGTH: 26
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (26)..(26)
<223> OTHER INFORMATION: n is dG modified with 3'-terminal phosphate
      group

<400> SEQUENCE: 41
ntacaccgga attgccagga cgaccn                                             26

<210> SEQ ID NO 42
<211> LENGTH: 27
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (27)..(27)
<223> OTHER INFORMATION: n is dG modified with 3'-terminal phosphate
      group

<400> SEQUENCE: 42
ntacaccgga attgccagga cgaccgn                                            27

<210> SEQ ID NO 43
<211> LENGTH: 28
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (28)..(28)
<223> OTHER INFORMATION: n is dG modified with 3'-terminal phosphate
      group

<400> SEQUENCE: 43
ntacaccgga attgccagga cgaccggn                                           28

<210> SEQ ID NO 44
<211> LENGTH: 27
<212> TYPE: DNA
<213> ORGANISM: Artificial
<220> FEATURE:
<223> OTHER INFORMATION: Synthetic oligonucleotide probe
<220> FEATURE:
```

```
<221> NAME/KEY: misc_feature
<222> LOCATION: (1)..(1)
<223> OTHER INFORMATION: n is dA modified with 6-carboxy-fluorescein
      (FAM)
<220> FEATURE:
<221> NAME/KEY: misc_feature
<222> LOCATION: (27)..(27)
<223> OTHER INFORMATION: n is dG modified with 3'-terminal phosphate
      group

<400> SEQUENCE: 44
ngtacaccgg aattgccagg acgaccn                                         27

<210> SEQ ID NO 45
<211> LENGTH: 25
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dA modified with 6-carboxy-fluorescein
      (FAM)
<220> FEATURE:
<221> NAME/KEY: misc_feature
<222> LOCATION: (25)..(25)
<223> OTHER INFORMATION: n is dC modified with 3'-terminal phosphate

<400> SEQUENCE: 45
ngtacaccgg aattgccagg acgan                                           25

<210> SEQ ID NO 46
<211> LENGTH: 25
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with 6-carboxy-fluorescein
      (FAM)
<220> FEATURE:
<221> NAME/KEY: misc_feature
<222> LOCATION: (25)..(25)
<223> OTHER INFORMATION: n is dA modified with 3'-terminal phosphate
      group

<400> SEQUENCE: 46
nagtacaccg gaattgccag gacgn                                           25

<210> SEQ ID NO 47
<211> LENGTH: 25
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with 6-carboxy-fluorescein
      (FAM)
<220> FEATURE:
<221> NAME/KEY: misc_feature
<222> LOCATION: (25)..(25)
<223> OTHER INFORMATION: n is dG modified with 3'-terminal phosphate
      group

<400> SEQUENCE: 47
ngagtacacc ggaattgcca ggacn                                           25
```

```
<210> SEQ ID NO 48
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with (FAM)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 48
nggaattgcc aggatgaccg n                                              21

<210> SEQ ID NO 49
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 49
nggaattgcc gggatgaccg n                                              21

<210> SEQ ID NO 50
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 50
nggaattgcc gggacgaccg n                                              21

<210> SEQ ID NO 51
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (21)..(21)
<223> OTHER INFORMATION: n is dG modified with 3'-terminal phosphate
```

```
<400> SEQUENCE: 51
nggaatcgcc gggatgaccg n                                         21

<210> SEQ ID NO 52
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 3',4,4',5',7,7'-
      hexachlorofluorescein (HEX)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 52
nggaatcgcc gggatgaccg n                                         21

<210> SEQ ID NO 53
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 3',4,4',5',7,7'-
      hexachlorofluorescein (HEX)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 53
nggaattgct gggaagactg n                                         21

<210> SEQ ID NO 54
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 3',4,4',5',7,7'-
      hexachlorofluorescein (HEX)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 54
nggaatcgct ggggtgactg n                                         21

<210> SEQ ID NO 55
<211> LENGTH: 21
<212> TYPE: DNA
<213> ORGANISM: Artificial
<220> FEATURE:
<223> OTHER INFORMATION: Synthetic oligonucleotide probe
<220> FEATURE:
```

```
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 55
nccgcaagac tgctagccga n                                              21

<210> SEQ ID NO 56
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 3',4,4',5',7,7'-
      hexachlorofluorescein (HEX)
<220> FEATURE:
<221> NAME/KEY: misc_feature
<222> LOCATION: (21)..(21)
<223> OTHER INFORMATION: n is dG modified with 3'-terminal phosphate
      group

<400> SEQUENCE: 56
nccgcaagac tgctagccga n                                              21

<210> SEQ ID NO 57
<211> LENGTH: 30
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with 6-carboxy-fluorescein
      (FAM)
<220> FEATURE:
<221> NAME/KEY: misc_feature
<222> LOCATION: (30)..(30)
<223> OTHER INFORMATION: n is dG modified with 3'-terminal phosphate

<400> SEQUENCE: 57
ntcttggatc aacccgctca atgcctggan                                     30

<210> SEQ ID NO 58
<211> LENGTH: 26
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (26)..(26)
<223> OTHER INFORMATION: n is N6-t-butylbenzyl-dA

<400> SEQUENCE: 58
gcagaaagcg tctagccatg gcgttn                                         26

<210> SEQ ID NO 59
<211> LENGTH: 28
<212> TYPE: DNA
<213> ORGANISM: Artificial
<220> FEATURE:
<223> OTHER INFORMATION: Synthetic oligonucleotide primer
```

```
<220> FEATURE:
<221> NAME/KEY: misc_feature
<222> LOCATION: (28)..(28)
<223> OTHER INFORMATION: n is N6-t-butylbenzyl-dA

<400> SEQUENCE: 59
gcaagcaccc tatcaggcag taccacan                                      28

<210> SEQ ID NO 60
<211> LENGTH: 31
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with 6-carboxy-fluorescein
      (FAM)
<220> FEATURE:
<221> NAME/KEY: misc_feature
<222> LOCATION: (14)..(15)
<223> OTHER INFORMATION: BHQ-2 is inserted between nucleotide positions
      14 and 15
<220> FEATURE:
<221> NAME/KEY: misc_feature
<222> LOCATION: (31)..(31)
<223> OTHER INFORMATION: n is dG modified with 3'-terminal phosphate
      group

<400> SEQUENCE: 60
nggtgtactc accgttccgc agaccactat n                                  31
```

PROBES AND METHODS FOR HEPATITIS C VIRUS TYPING USING MULTIDIMENSIONAL PROBE ANALYSIS

CROSS-REFERENCE TO RELATED APPLICATIONS

This application claims priority to and benefit of the following United States Provisional Patent Applications:
Application Ser. No. 60/695,991, filed Jun. 30, 2005;
Application Ser. No. 60/696,253, filed Jun. 30, 2005;
Application Ser. No. 60/696,293, filed Jun. 30, 2005; and
Application Ser. No. 60/696,303, filed Jun. 30, 2005.
Each of these specifications are hereby incorporated by reference in their entirety.

FIELD OF THE INVENTION

The invention relates to viral diagnostic procedures. Specifically, the invention relates to hepatitis C virus typing (e.g., genotyping and subtyping). The invention provides compositions and methods for typing an HCV in a sample, for example, a sample from a patient.

BACKGROUND OF THE INVENTION

Hepatitis C Virus (HCV) infection is a growing worldwide concern. HCV infections are generally persistent and induce chronic liver disease, manifested in cirrhosis of the liver and hepatocellular carcinoma. HCV is the leading cause for liver transplantation in the United States. Worldwide, approximately one million new HCV infections are reported annually; in the United States alone, an estimated four million persons are infected and 30,000 new infections occur annually.

Currently, HCV is responsible for an estimated 8,000 to 10,000 deaths annually in the United States. Without the development of improved diagnostics and therapeutics, that number is expected to triple in the next 10 to 20 years (National Institutes of Health Consensus Development Conference Panel (1997) National Institutes of Health Consensus Development Conference Panel statement: "Management of Hepatitis C," Hepatology 26(Suppl. 1):2S-10S).

The HCV genome is highly polymorphic, and a number of strains (termed genotypes and subtypes) have been characterized. The different viral types correlate with different disease outcomes and different responsiveness to therapeutic regimens. Knowing the viral genotype (and/or subtype) present in an infection provides the clinician with an important indicator for determining an optimal course of treatment for an infected patient. However, the development of diagnostic methods that can differentiate the ever-increasing number of known HCV types has become a challenge.

There is a need in the art to develop improved methods for HCV diagnostics. There is a need for improved methods that can distinguish the increasingly large number of known HCV genotypic isolates, including genotypic subtypes. Furthermore, there is also a need in the art for methods that can simultaneously genotype and quantitate (e.g., determine the viral load or copy number) an HCV in a sample. The present invention provides novel compositions and methods that meet these needs, as well as provides additional benefits.

Prior to a detailed description of the present invention, pertinent aspects of HCV nomenclature and biology are discussed below. These topics, required for understanding the invention, include discussion of the HCV genome, HCV typing nomenclature, clinical relevance of HCV typing and HCV typing methodologies.

HCV Genome

The HCV genome (see, FIG. 1) has a positive-sense single-stranded RNA genome approximately 10 kb in length with marked similarities to the genomes of members of the *Pestivirus* and *Flavivirus* genera. The original HCV isolate (HCV-1) had an approximately 9.4 kB genome containing a poly(A) tail at the 3' end (Choo et al. (1991) "Genetic organization and diversity of the hepatitis C virus," Proc. Natl. Acad. Sci. USA 88:2451-2455). The HCV-1 sequence contained a 5' untranslated region (5'-UTR) of 341 bases, a long open reading frame encoding a polyprotein of 3,011 amino acids, and a 3' untranslated region (3'-UTR) of about 27 bases. See the schematic of the HCV genome and polyprotein in FIG. 1.

The viral RNA genome is translated by the host translation apparatus as a single polyprotein product, which is then subjected to proteolytic processing to produce the viral proteins. The length of the open reading frame (ORF) of each genotype is characteristically different. For example, the open reading frame in type 1 isolates is approximately 9,400 ribonucleotides in length, while that of type 2 isolates is typically 9,099 nucleotides and that of type 3 isolates is typically 9,063 nucleotides (Bukh et al. (1995) "Genetic heterogeneity of hepatitis C virus: quasispecies and genotypes," Semin. Liver Dis., 15:41-63).

The HCV genomic structure/organization is most similar to that of the family Flaviviridae. Consistent with the known functions of most *flavivirus* proteins, the N-terminal HCV proteins are likely structural (including the C (capsid/core), E1 and E2 envelope proteins) and the C-terminal non-structural proteins, including NS2 (metalloprotease), NS3 (serine-protease/helicase), NS4 and NS5 (NS5B RNA polymerase) are believed to function in viral replication. A schematic view showing organization of the HCV RNA genome and encoded polypeptides is provided in FIG. 1.

Following identification and characterization of the prototypical HCV isolate (now termed HCV 1a), other isolates from around the world were (and continue to be) identified. Sequence comparisons reveal that these unique isolates can differ from each other by as much as 35% nucleotide non-identity over the full length of the HCV genome (Okamoto et al. (1992) Virology 188:331-341). Sequence variability is observed throughout the viral genome, with some regions showing more variability than others. For example, generally high sequence conservation is observed in the 5'-UTR region; conversely, some regions, including the envelope (E) region, show hypervariable nucleotide sequences.

HCV Typing Nomenclature

An understanding of HCV typing nomenclature is required prior to discussion of the present invention. Historically, investigators have used several classification systems and nomenclatures to characterize the various HCV strains, resulting in confusion in the scientific literature. A consensus HCV genotype/subtype nomenclature system has now been adopted (Simmonds et al. (1994) Letter, Hepatology 19:1321-1324; see also, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England). According to this system, HCV isolates are classified on the basis of nucleotide sequence divergence into major genetic groups designated as genotypes. These genotypes are numbered (in Arabic numerals), generally in the order of their discovery. HCV strains that are more closely related to each other within a genotype are designated as subtypes, which are assigned lowercase letters, generally in the order of their discovery. Genetic variants found within an individual isolate are termed quasispecies. Quasispecies of HCV result presumably from the accumulation of mutations during viral replication in the host.

The degree of relatedness between any two HCV isolates can be quantitated, for example, by determining the percentage of nucleotide identity between the two genomes over the full length of the genome. One example of this relatedness analysis, and how the nomenclature is used to reflect viral isolate relatedness, is shown in FIG. 2 (adapted from Zein (2000) "Clinical Significance of Hepatitis C Virus Genotypes," Clinical Microbiol. Reviews 13(2):223-235). Using the nomenclature proposed by Simmonds et al. (1994, Letter, Hepatology 19:1321-1324), the increasing degree of interrelatedness between genotypes, subtypes and quasispecies can be observed in the percentage of nucleotide sequence identity over the complete genome. The table in FIG. 2 reflects the proposal that HCV isolates that are quasispecies share the greatest degree of relatedness, and isolates of the same subtype within a genotype share greater sequence identity than isolates of different subtypes also within that genotype.

Alternatively, relatedness between HCV isolates can be quantitated by examining genomic identity over a smaller domain of the genome, as shown, for example, in FIG. 3. This comparison uses a 222 nucleotide segment derived from the viral NS5 open reading frame (nucleotide positions 7975-8196 in the prototype HCV type 1a isolate). This comparison of sequence identity also supports the proposal of Simmonds et al. (1994, Letter, Hepatology 19:1321-1324) that HCV isolates of one subtype are more closely related to other subtypes of that same genotype, than to isolates from any other genotype.

Currently, eleven (11) HCV genotypes are recognized worldwide. However, there is published suggestion that the evolutionary (phylogenetic) relatedness between different genotypes should be reexamined, and the number of recognized genotypes into which HCV isolates are classified/assigned should be reassessed. Some reports suggest that subsets of HCV genotypes are more closely related to each other than to other more distantly related genotypes, which should be reflected in a modified HCV nomenclature. It is suggested that the 11 genotypes can be regrouped into six HCV clades. The grouping of clades reflects phylogenetic relationships between the genotypes, where genotypes 1, 2, 4 and 5 all represent distinct clades, but where genotypes 3 and 10 are placed into a single lade 3, and genotypes 6, 7, 8, 9 and 11 are placed into a single lade 6 (Robertson et al., (1998) Arch. Virol., 143(12):2493-2503; Zein (2000) "Clinical Significance of Hepatitis C Virus Genotypes," Clinical Microbiol. Reviews 13(2):223-235).

Approximately 78 HCV subtypes encompassing all 11 genotypes are known worldwide. A summary of some of these subtypes is shown in FIG. 4. This table provides a listing of some (but not all) HCV types, especially those subtypes that appear to be frequent clinical isolates. The names of prototypical and/or representative isolates known in the art are provided.

Many HCV isolates have been sequenced in their entirety. FIG. 5 provides a table showing the consensus sequences of a 33 nucleotide domain in the 5'-UTR of some of the clinically relevant HCV isolates. Nucleotide positions that are identical to the HCV type 1a nucleotide sequence are shown with a dash. Nucleotide positions that differ from the HCV type 1a are shown with the nucleotide change.

All references to HCV genotypes, subtypes and quasispecies herein are in accordance with the system described by Simmonds et al., 1994, (Letter, Hepatology 19:1321-1324), and also described in, for example, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England.

Clinical Relevance of HCV Typing

The typing of an HCV infection in a patient remains an important prognosticator for the aggressiveness of the infection, as well as the potential for the infection to respond to various therapeutic regimens. HCV genotype 1 represents a more aggressive strain and one that is less likely to respond to alpha interferon (INF-α) treatment (and combination therapies with ribavirin) than HCV genotype 2 or 3 (Nolte, "Hepatitis C Virus Genotyping: Clinical Implications and Methods," Molecular Diagnosis 6(4):265-277 [2001]; Dufour, "Hepatitis C: Laboratory Tests for Diagnosis and Monitoring of Infection," Clinical Laboratory News, November 2002, p. 10-14; Pawlotsky "Use and Interpretation of Hepatitis C Virus Diagnostic Assays," *Clinics in Liver Disease*, Vol. 7, Number 1 [February 2003]). The goal in typing an HCV infection is frequently to identify patients infected with HCV genotype 1 as opposed to those infected with other HCV types. Furthermore, with the identification of an expanding list of known HCV subtypes, there is a need in the art for simple HCV typing methods that can distinguish the complexity of HCV phylogeny for both clinical and research purposes. There is also a need in the art for HCV typing methods that simultaneously provide HCV load information (e.g., copy number and viral genome quantitation).

Substantial regional differences exist in the distribution of the HCV types. HCV subtypes 1a and 1b are the most common subtypes in the United States and Europe. In Japan, subtype 1b is responsible for up to 73% of cases of HCV infection. Although HCV subtypes 2a and 2b are relatively common in North America, Europe, and Japan, subtype 2c is found commonly in northern Italy. HCV genotype 3a is particularly prevalent in intravenous drug abusers in Europe and the United States. HCV genotype 4 appears to be prevalent in North Africa and the Middle East, and genotypes 5 and 6 seem to be confined to South Africa and Hong Kong, respectively. HCV genotypes 7, 8, and 9 have been identified only in Vietnamese patients, and genotypes 10 and 11 were identified in patients from Indonesia. (see, Nolte, "Hepatitis C Virus Genotyping: Clinical Implications and Methods," Molecular Diagnosis 6(4):265-277 [2001]; Pawlotsky "Hepatitis C Virus Genetic Variability: Pathogenic and Clinical Implications," *Clinics in Liver Disease*, Vol. 7, Number 1 [February 2003]; Zein "Clinical Significance of Hepatitis C Virus Genotypes," Clinical Microbiol. Reviews 13(2):223-235 [2000]).

Because of the geographic clustering of distinct HCV genotypes and subtypes, HCV typing can also be a useful epidemiologic marker in tracing the source of an HCV outbreak in a given population. For example, HCV typing was used to trace the source of HCV infection in a group of Irish women to contaminated anti-D immunoglobulins (Power et al., (1995) "Molecular epidemiology of an outbreak of infection with hepatitis C virus in recipients of anti-D immunoglobulin," Lancet 345:1211-1213). Additional examples of using HCV typing as an epidemiological marker are also known (see, for example, Hohne et al., (1994) "Sequence variability in the env-coding region of hepatitis C virus isolated from patients infected during a single source outbreak," Arch. Virol., 137:25-34; and Bronowicki et al., (1997) "Patient-to-patient transmission of hepatitis C virus during colonoscopy," N. Engl. J. Med., 337:237-240).

HCV Typing Methodologies

The HCV isolate found in any given infection varies by differences in geographical strain distribution, disease outcome, and response to anti-HCV therapy. Reliable methods for determining HCV genotype are an important clinical test. Furthermore, with the identification of numerous and distinct HCV species, it is important that HCV typing methods have the ability to distinguish numerous HCV types (genotypes and subtypes). For example, it is useful for an HCV genotyping test to be able to distinguish among at least five or more genotypes. Alternatively, it is useful for an HCV typing test to be able to distinguish among at least six or more subtypes. Nucleic acid-based methods for HCV typing are summarized below.

Nucleotide Sequencing

The reference standard for HCV genotyping and subtyping is nucleotide sequencing of an amplicon derived from the HCV genome by RT-PCR of HCV genomic RNA (e.g., from a clinical specimen from a patient) followed by phylogenetic assignment. However, direct sequencing is impractical due to low throughput (even with the introduction of automated sequencing apparatus using non-radioactive reagents) and the requirement for specialized equipment. Furthermore, using sequencing methodologies for genotyping and subtyping in cases of mixed infections can result in ambiguous results.

PCR-Based HCV Genotyping

Some typing methods use PCR reamplification using type-specific PCR primers. Typing is achieved by a primary PCR amplification with universal consensus primers (i.e., primers that will generate an HCV genomic amplicon regardless of the HCV type) followed by a nested PCR with the type-specific primers, for example, type-specific primers within the core region. These assays require multiple sets of PCR primers to generate sufficient type-specific PCR amplicons to make a genotype/subtype assignment. These methods have the drawback that they require multiple sets of PCR primers to accomplish the HCV typing, and often lack sensitivity and specificity (Xavier and Bukh (1998) "Methods for determining the hepatitis C genotype," Viral Hepatitis Rev., 4:1-19; Zein (2000) "Clinical Significance of Hepatitis C Virus Genotypes," Clinical Microbiol. Reviews 13(2):223-235; Okamoto et al., (1992) "Typing hepatitis C virus by polymerase chain reaction with type-specific primers: application to clinical surveys and tracing infectious sources," J. Gen. Virol., 73:673-679; Widell et al. (1994) "Genotyping of hepatitis C virus isolates by a modified polymerase chain reaction assay using type specific primers: epidemiological applications," J. Med. Virol., 44:272-279).

Hybridization-Based HCV Genotyping

The typing of HCV isolates can be achieved by using multiple type-specific hybridization probes. This viral typing uses a primary PCR amplification using universal primers followed by hybridization with type-specific hybridization probes. This hybridization with the type-specific probes is done in fixed hybridization conditions, and the presence or absence of a hybridization complex(es) under the given hybridization conditions is scored. Any one probe in the assay is unable to definitively distinguish from among multiple genotypes/subtypes, thus necessitating the use of multiple probes to make a genotype/subtype assignment. This approach suffers from the drawback of requiring multiple probes for use in the HCV typing process.

One application of the HCV type-specific hybridization assay is the line-probe assay (LiPA), as described in various sources (Stuyver et al., (1993) "Typing of hepatitis C virus isolates and characterization of new subtypes using a line probe assay," J. Gen. Virol., 74:1093-1102; Stuyver et al., (1994) Proc. Natl. Acad. Sci. USA 91:10134-10138; Andonov and Chaudhary (1995) Jour. Clin. Microbiol., 33(1):254-256; Stuyver et al., (1996) Jour. Clin. Microbiol., 34(9):2259-2266; Stuyver et al., (2000) Jour. Clin. Microbiol., 38(2):702-707; and reviewed in, e.g., Maertens and Stuyver (1997) "Genotypes and genetic variation of hepatitis C virus," p. 182-233, In Harrison and Zuckerman (eds.), *The Molecular Medicine Of Viral Hepatitis*, John Wiley & Sons, Ltd., Chichester, England). A commercial kit incorporating this technology is produced by Innogenetics (Zwijnaarde, Belgium; see U.S. Pat. No. 6,548,244, issued Apr. 15, 2003 to Maertens et al., entitled "PROCESS FOR TYPING HCV ISOLATES"; Published PCT International Application No. WO96/13590, published May 9, 1996, by Maertens and Stuyver, entitled "NEW SEQUENCES OF HEPATITIS C VIRUS GENOTYPES AND THEIR USE AS PROPHYLACTIC, THERAPEUTIC AND DIAGNOSTIC AGENTS"; and Published PCT International Application No. WO94/25601, published Nov. 10, 1994, by Maertens and Stuyver, entitled "NEW SEQUENCES OF HEPATITIS C VIRUS GENOTYPES AND THEIR USE AS THERAPEUTIC AND DIAGNOSTIC AGENTS"). The line-probe assay uses multiple type-specific probes (as many as 21 probes) immobilized onto a substrate (a test strip) in a dot-blot or slot-blot type of assay. An HCV amplicon derived from the HCV 5'-UTR region generated from a clinical specimen is simultaneously hybridized to the various probes under static hybridization conditions, and the resulting pattern of hybridization complexes reveals the virus type.

This line-probe assay suffers from the drawback of requiring the use of multiple probes (indeed, as many as 21 probes) to determine the HCV genotype and/or subtype of an HCV in a sample, as any one probe in the assay is unable to make a genotypic assignment.

Some reports use HCV typing methods that utilize one probe (or a small number of probes) to classify an HCV infection into one of a few subtypes. The probes used in these reports are not "type-specific," in that they can hybridize to multiple genotypes/subtypes by manipulating the hybridization conditions. However, these types of probes reported in the art (see, e.g., Schroter et al., (2002) Jour. Clin. Microbiol., 40(6):2046-2050; Bullock et al., (2002) Clinical Chemistry 48(12):2147-2154) are limited in the number of genotypes/subtypes they can differentiate.

Endonuclease Cleavage (RFLP)-Based HCV Genotyping

Typing of HCV has also been attempted by a variation of the traditional restriction fragment length polymorphism (RFLP) assay. This HCV assay uses digestion of a universal PCR amplicon with restriction endonucleases that recognize genotype-specific cleavage sites (see, e.g., Nakao et al., (1991) "Typing of hepatitis C virus genomes by restriction fragment length polymorphism," J. Gen. Virol., 72:2105-2112; Murphy et al., (1994) Letter, J. Infect. Dis., 169:473-475). Type-specific restriction sites are known to occur in the NS5 and the 5'-UTR domains. The use of this assay for genotyping/subtyping is limited due to the limited number of polymorphic loci that result in changes in restriction sites.

HCV Typing Challenges

Determining an HCV virus type in a sample is an important clinical tool. One technique for making an HCV type determination is to characterize the melting temperatures of hybridization complexes formed with an HCV-specific probe using known HCV types and the experimental HCV sample. Ideally, an HCV typing probe in a complex with an HCV genomic sequence (or derivative of and/or portion of an HCV genomic sequence) will yield a unique $T_m$ value corresponding to a specific HCV type, and thus the assignment of a particular HCV type is made on the basis of the experimentally observed $T_m$ value.

However, as the numbers of known HCV types increases and more quasispecies are identified, the use of a single probe to make an HCV type determination becomes more challenging. This is illustrated in FIG. 8. In this figure, a hypothetical HCV Typing Probe A forms complexes with HCV genotypes 1 through 6. These complexes are each characterized by a range of $T_m$ values, as opposed to one absolute value. A number of variables contribute to this range in $T_m$ values, including but not limited to (i) HCV sequence variants such as quasispecies, (ii) the particular melting analysis reaction conditions (e.g., salt concentrations and the concentrations of the nucleic acids in the hybridization reactions), and (iii) the accuracy and precision of the melting analysis instrumentation, including the thermocycling device and the detector (e.g., the spectrophotometer). As shown in FIG. 8, it is possible that the $T_m$ value range for any one HCV/probe combination overlaps with or can not be distinguished from the $T_m$ values for another HCV type using that same probe. This situation makes a definitive determination of an HCV type impossible or ambiguous.

The present invention provides compositions and methods for HCV typing, and furthermore, provides compositions and methods for HCV typing that have advantages over other HCV typing methods known in the art. The compositions and methods for HCV typing described herein overcome the limitations in HCV typing as illustrated in FIG. 8. The invention provides methods for typing an HCV isolate, where the methods use a multidimensional analysis where combinations of HCV typing probes provide unique and complementary information on individual HCV types and are able to distinguish at least five HCV types (genotypes and/or subtypes). The process of multidimensional typing provides multiple datapoints to characterize each HCV type, increasing the accuracy and robustness of typing determination, while simultaneously providing a solution for discrepancies arising from intra-genotype variance. Furthermore, the invention provides methods that can simultaneously type an HCV in a sample as well as quantitate the HCV genomic material in the sample (e.g., determine the viral load or copy number). The compositions and methods taught by the present invention also provide other advantages, which will be apparent upon reading the description of the invention.

SUMMARY OF THE INVENTION

The present invention provides compositions and methods for HCV typing, e.g., genotyping and/or subtyping. More specifically, the invention provides compositions and methods for HCV typing that can be used to assign an HCV sample five or more HCV types (for example, selected from types 1, 2, 3, 4, 5 or 6), or from subtypes 1a/b/c, 2a/c, 2b, 3a, 4a, 5a or 6a). These methods integrate the hybridization data from a plurality of HCV typing probes in a multidimensional analysis to make an HCV type assignment for an HCV in an experimental sample. The invention also provides related compositions, including, for example, the HCV typing probes and HCV typing diagnostic kits.

In some embodiments, the invention provides methods for determining the type of a hepatitis C virus (HCV) in a sample. Generally, these methods comprise the steps: (a) amplifying a portion of the HCV genome from the sample, to produce at least one amplicon; (b) hybridizing the amplicon with at least a first and second HCV typing probe to form at least two target hybridization complexes, where: (i) each probe is complementary or partially complementary to nucleotide sequences within an HCV genome; (ii) the regions of hybridization complex complementarity or partial complementarity show sequence heterogeneity among at least two HCV types; (iii) hybridization complexes comprising the first probe have a distinguishing hybridization property that differentiates at least two HCV types; and, (iv) hybridization complexes comprising the second probe have a distinguishing hybridization property that differentiates at least two HCV types, wherein the at least two virus types differentiated by the first probe are different than the at least two HCV types differentiated by the second probe; (c) measuring the distinguishing hybridization property of the target hybridization complexes; and, (d) correlating the measured distinguishing hybridization property of the target hybridization complexes with one of at least five HCV types, where an assignment of an HCV type is made by considering the distinguishing hybridization property of the hybridization complexes comprising the first and second HCV typing probe. Using these methods, the HCV type can be selected from genotypes, e.g., 1, 2, 3, 4, 5 and 6, or alternatively, selected from any subtype of genotype 1, 2, 3, 4, 5 and 6, for example, subtype 1a, 1b, 1c, 2a, 2b, 2c, 3a, 3b, 4a, 5a or 6a. However, it is not intended that the invention be limited to the HCV types listed herein, since the compositions and methods of the invention are applicable to any HCV type. In some embodiments, the sample used comprises or was derived from human blood or human serum.

In some embodiments of these methods, the amplifying step is by reverse transcription (RT) coupled with polymerase chain reaction (PCR). Optionally, the PCR can use a primer pair comprising the nucleotide sequences of SEQ ID NOS: 58 and 59. The PCR primers used to generate an HCV amplicon can preferably generate an amplicon from a plurality of HCV types.

The multidimensional HCV typing analysis taught by the present disclosure is not limited to only two HCV typing probes. Indeed, three or more probes can be used in an analysis. For example, in some embodiments, the methods are modified where (a) the hybridizing step further comprises at least one additional HCV typing probe in addition to the first and second typing probes, to form a plurality of at least three target hybridization complexes; (b) the plurality of hybridization complexes have a distinguishing hybridization property; and (c) the assignment of an HCV type in the correlating step is made by considering the distinguishing hybridization property of the plurality of at least three hybridization complexes.

It is not intended that the HCV/probe hybridization complexes each occur in the same hybridization reaction. In some embodiments of these methods, the hybridizing step occurs in a single hybridization reaction, or alternatively, the hybridizing step can occur in more than one hybridization reaction. In other aspects, the HCV typing probes can be present or not present during the amplifying step. In the event that they are not present during the amplification, they can be added to the reaction mix after the amplifying step.

In some embodiments, the HCV typing probes optionally have nucleotide sequences that are complementary or partially complementary to nucleotide sequences within the 5'-UTR or the NS5 open reading frame of an HCV genome. For example, the HCV typing probes can have nucleotide sequences independently selected from the nucleotide sequences provided in SEQ ID NOs: 9 through 57. Optionally, the first and second HCV typing probes can comprise nucleotide sequences selected from, for example, SEQ ID NOs: 26 and 54, SEQ ID NOs: 10 and 53, and SEQ ID NOs: 57 and 52.

In some embodiments, at least one of the HCV typing probes can comprise a FRET donor moiety, a FRET quencher moiety, or both. Alternatively, at least one typing probe can comprise a FRET donor moiety and the hybridizing step comprises the use of a soluble FRET quencher, for example, a thiazine dye. In some embodiments, both the first and second HCV typing probes comprise FRET donor moieties, and the excitation and emission spectra of each FRET donor moiety is different. Where multiple labels are used, the measuring step can be accomplished by detecting emitted light at more than one wavelength. Optionally, where two different label systems are used simultaneously, at least one of the typing probes comprising a FRET donor moiety further comprises a FRET quencher moiety.

The chemical structure of the HCV typing probes is not particularly limited. One of skill in the art recognizes that a probe can have a variety of structures. For example, a nucleotide oligomer HCV typing probe can comprise naturally occurring nucleotides, modified nucleotides, nucleotide analogs, one or more unnatural bases, unnatural internucleotide linkages, unnatural nucleotide backbones, or any combination thereof.

In some embodiments of these methods, the distinguishing hybridization property of the hybridization complexes is a temperature-dependent hybridization property, for example, a melting temperature ($T_m$). Where the $T_m$ is used as the distinguishing hybridization property, the measuring step comprises detecting the target hybridization complexes at a range of temperatures, thereby determining a $T_m$ of the target hybridization complexes.

These methods for HCV typing incorporate a correlating step, where the distinguishing hybridization property of the target hybridization complexes are compared to the distinguishing hybridization property of hybridization complexes comprising each probe and a plurality of known HCV types.

In some embodiments, the methods for HCV typing further incorporate viral quantitation, where the viral load as well as the viral type are determined. In these embodiments, a viral quantitation probe is incorporated into the amplification reaction. That is to say, the methods for viral typing are modified to also provide HCV viral load information from the sample, wherein the amplifying step further comprises monitoring a rate of accumulation of the amplicon using reagents for real-time detection of amplicon accumulation and correlating the rate of amplicon accumulation with the viral load. In some aspects, the reagents for real-time detection of amplicon accumulation comprise an amplicon quantitation probe, for example, a probe comprising a nucleotide sequence of SEQ ID NO: 60. In some embodiments, the amplicon quantitation probe comprises a FRET donor moiety and a FRET quencher moiety, and the amplicon quantitation probe forms a quantitation hybridization complex with the amplicon under conditions where base-pairing occurs. In these quantitation/typing hybrid methods, the amplifying step can further comprise detecting the donor moiety from the quantitation probe during the amplification step.

The present disclosure also provides methods for determining an HCV type in a sample, but where the methods do not use an HCV amplification step. These methods use the steps: (a) hybridizing an unamplified HCV nucleic acid (or an unamplified nucleic acid corresponding to or derived from an HCV) with at least a first and second HCV typing probe, to form at least two target hybridization complexes, wherein (i) each probe is complementary or partially complementary to nucleotide sequences within an HCV genome; (ii) the regions of hybridization complex complementarity or partial complementarity show sequence heterogeneity among at least two HCV types; (iii) hybridization complexes comprising the first typing probe have a distinguishing hybridization property that differentiates at least two HCV types; and, (iv) hybridization complexes comprising the second typing probe have a distinguishing hybridization property that differentiates at least two HCV types, wherein the at least two virus types differentiated by the first probe are different than the at least two HCV types differentiated by the second probe; (b) measuring the distinguishing hybridization property of the target hybridization complexes; and (c) correlating the measured distinguishing hybridization property of the target hybridization complexes with one of at least five HCV types, where an assignment of an HCV type is made by considering the distinguishing hybridization property of the hybridization complexes comprising the first and second typing probes. Optionally, the first and second typing probes can comprise nucleotide sequences independently selected from the nucleotide sequences provided in SEQ ID NOs: 9 through 57. For example, typing probe pairs can incorporate nucleotide sequences selected from SEQ ID NOs: 26 and 54, SEQ ID NOs: 10 and 53, and SEQ ID NOs: 57 and 52.

The invention also provides a variety of compositions of matter. For example, the invention provides a plurality of probes, where (a) each probe comprises a nucleotide sequence that is complementary or partially complementary to a nucleotide sequence within a hepatitis C virus (HCV) genome; (b) the regions of complementarity or partial complementarity show sequence heterogeneity among at least two HCV types; (c) hybridization complexes comprising (i) any one probe from the plurality of probes, and (ii) nucleotide sequences from at least two HCV types have a distinguishing hybridization property that permits differentiation of the at least two HCV types; (d) the at least two HCV types differentiated by any one probe from the plurality of probes are different than the at least two HCV types differentiated by a second different probe from the plurality of probes; and, (e) the distinguishing hybridization property of each of the hybridization complexes comprising at least two probes from the plurality of probes correlates with one of at least five HCV types, wherein an assignment of an HCV type is made by considering the distinguishing hybridization property of the hybridization complexes. For example, the plurality of typing probes can comprise nucleotide sequences independently selected from the nucleotide sequences provided in SEQ ID NOs: 9 through 57. Optionally, the plurality of typing probe pairs can incorporate nucleotide sequences selected from SEQ ID NOs: 26 and 54, SEQ ID NOs: 10 and 53, and SEQ ID NOs: 57 and 52. In some embodiments, the distinguishing hybridization property of the plurality of hybridization complexes is a melting temperature ($T_m$).

Compositions of the invention that comprise a plurality of HCV typing probes can optionally further comprise a reverse transcriptase and a primer suitable for the initiation of reverse transcription of an HCV genome. The compositions comprising the plurality of typing probes can also optionally comprise a nucleic acid that is either (a) an HCV amplicon comprising a nucleotide sequence that is complementary or partially complementary to a nucleotide sequence in at least two typing probes in the plurality of probes; (b) an amplification primer capable of generating the HCV amplicon; or (c) an amplification primer pair capable of generating the HCV amplicon; wherein the primer and the primer pair are admixed with a thermostable DNA-dependent DNA polymerase, free deoxyribonucleotide triphosphates and a suitable DNA polymerase reaction buffer. In still other embodiments of the compositions of typing probes, optionally, at least one probe from the plurality of probes comprises a FRET donor moiety, and where the composition comprises a soluble FRET quencher that is capable of quenching the FRET donor moiety.

In other aspects, the invention also provides kits, for example, diagnostic kits for determining the type of a hepatitis C virus (HCV) in a sample, where these kits comprise a plurality of HCV typing probes as described herein. For example, in some embodiments, the diagnostic kits of the invention comprise: (a) a plurality of HCV typing probes, wherein (i) each typing probe comprises a nucleotide sequence that is complementary or partially complementary to a nucleotide sequence within an HCV genome; (ii) the regions of complementarity or partial complementarity show sequence heterogeneity among at least two HCV types; (iii) hybridization complexes comprising (i) any one probe from the plurality of probes and (ii) nucleotide sequences from at least two HCV types have a distinguishing hybridization property that permits differentiation of the at least two virus types; (iv) the at least two HCV types differentiated by one probe from the plurality of probes are different than the at least two HCV types differentiated by a second different probe from the plurality of probes; and, (v) the distinguishing hybridization property of each of the hybridization complexes comprising at least two probes from the plurality of probes correlates with one of at least five HCV types, wherein an assignment of an HCV type is made by considering the distinguishing hybridization property of the hybridization complexes; and, (b) instructions for measuring the distinguishing hybridization property of hybridization complexes comprising a target probe from the plurality of target probes. The diagnostic kits of the invention can be packaged in one or more containers.

Optionally, the plurality of typing probes in the diagnostic kits of the invention are independently selected from the nucleotide sequences provided in SEQ ID NOs: 9 through 57. For example, in some embodiments, where the plurality of typing probes comprises at least two typing probes, those probes can comprise nucleotide sequences selected from SEQ ID NOs: 26 and 54, SEQ ID NOs: 10 and 53, and SEQ ID NOs: 57 and 52. Optionally, the diagnostic kits can comprise an amplification primer pair for the amplification of an HCV nucleotide sequence, e.g., the primer pair comprising the nucleotide sequences of SEQ ID NOS: 58 and 59.

In some embodiments, the diagnostic kits are further useful for viral quantitation, i.e., determining a viral load of the HCV in the sample. In this case, the kits can optionally comprise reagents for the quantitation. For example, the dual-purpose quantitation/typing kit can comprise (c) an amplification primer pair capable of generating an HCV amplicon, where the amplicon comprises nucleotide sequences that are complementary or partially complementary to nucleotide sequences in at least two typing probes from the plurality of typing probes; and, (d) an amplicon quantitation probe for real-time detection of amplicon accumulation, wherein the amplicon quantitation probe forms a quantitation hybridization complex with the amplicon under conditions where base-pairing occurs.

In some embodiments, a diagnostic kit of the invention comprises label or detection reagents. For example, at least one typing probe in a diagnostic kit can comprise a FRET donor moiety, and further where the kit comprises at least one soluble FRET quencher comprising a thiazine dye that is capable of quenching the FRET donor moiety. Furthermore, in other embodiments, a diagnostic kit can comprise any number of additional components (alone or in combination), for example but not limited to, a reverse transcriptase, a thermostable DNA-dependent DNA polymerase, free deoxyribonucleotide triphosphates, standardization samples, positive control samples, negative control samples, buffers suitable for enzymatic reactions, sample collection tubes, amplification reaction tubes and multi-well plates.

In some embodiments, the invention provides systems that integrate the various aspects of the HCV typing methods of the invention and facilitate their use. In addition to the reagents required for performing the HCV hybridization analysis (for example, the plurality of HCV typing probes), the integrated systems of the invention can optionally comprise, for example, computer hardware, software, or other instrumentation for performing the HCV typing. For example, the invention provides systems that correlate detection of a plurality of signals with a hepatitis C virus (HCV) type, where the system comprises: (a) a detector for detecting the signals, where the signals correlates with a distinguishing hybridization property of hybridization complexes, and (b) a correlation module operably coupled to the detector, wherein the correlation module receives the signals detected by the detector and correlates the signals with an HCV type by correlating the detected signals with predicted or predetermined signals observed when detecting the distinguishing hybridization property of hybridization complexes comprising a plurality of known HCV types, wherein during operation of the system (i) the signals are generated from a plurality of hybridization complexes comprising an amplicon comprising an HCV nucleotide sequence and at least a first and second HCV typing probes; (ii) the first and second typing probe nucleotide sequences are complementary or partially complementary to nucleotide sequences within an HCV genome; (iii) the regions of hybridization complex complementarity or partial complementarity show sequence heterogeneity among at least two HCV types; (iv) hybridization complexes comprising the first typing probe have a distinguishing hybridization property that differentiates at least two HCV types; (v) hybridization complexes comprising the second typing probe have a distinguishing hybridization property that differentiates at least two HCV types, wherein the at least two virus types differentiated by the first probe are different than the at least two virus types differentiated by the second probe; and (vi) the distinguishing hybridization property of each of the hybridization complexes comprising each of the at least two probes correlates with one of at least five HCV types.

Optionally, in the systems of the invention, the distinguishing hybridization property is a melting temperature ($T_m$), and the correlation module comprises a dataset of predicted or experimentally determined $T_m$ values for hybridization complexes comprising the at least first and second typing probes and each HCV type in the plurality of known HCV types, where the dataset is in a computer readable format.

DEFINITIONS

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "a nucleic acid," also includes a plurality of nucleic acid molecules; use of the term "probe" includes, as a practical matter, many probe molecules, and the like.

Unless otherwise indicated, nucleic acids are written left to right in 5' to 3' orientation, and amino acid sequences are written left to right in amino (N-terminus) to carboxy (C-terminus) orientation. Numeric ranges recited within the specification are inclusive of the numbers defining the range and include each integer and any non-integer fraction within the defined range.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

As used herein, the term "base" refers to any nitrogen-containing heterocyclic moiety capable of forming Watson-Crick type hydrogen bonds in pairing with a complementary base or base analog. A large number of natural and synthetic (non-natural, or unnatural) bases, base analogs and base derivatives are known. Examples of bases include purines and pyrimidines, and modified forms thereof. The naturally occurring bases include, but are not limited to, adenine (A), guanine (G), cytosine (C), uracil (U) and thymine (T). As used herein, it is not intended that the invention be limited to naturally occurring bases, as a large number of unnatural (non-naturally occurring) bases and their respective unnatural nucleotides that find use with the invention are known to one of skill in the art. Example of such unnatural bases are given below.

The term "nucleoside" refers to a compound consisting of a base linked to the C-1' carbon of a sugar, for example, ribose or deoxyribose.

The term "nucleotide" refers to a phosphate ester of a nucleoside, as a monomer unit or within a polynucleotide. "Nucleotide 5'-triphosphate" refers to a nucleotide with a triphosphate ester group attached to the sugar 5'-carbon position, and are sometimes denoted as "NTP", or "dNTP" and "ddNTP." A modified nucleotide is any nucleotide (e.g., ATP, TTP, GTP or CTP) that has been chemically modified, typically by modification of the base moiety. Modified nucleotides include, for example but not limited to, methylcytosine, 6-mercaptopurine, 5-fluorouracil, 5-iodo-2'-deoxyuridine and 6-thioguanine. As used herein, the term "nucleotide analog" refers to any nucleotide that is non-naturally occurring.

The terms "polynucleotide," "nucleic acid," "oligonucleotide," "oligomer," "oligo" or equivalent terms, as used herein refer to a polymeric arrangement of monomers that can be corresponded to a sequence of nucleotide bases, e.g., a DNA, RNA, peptide nucleic acid, or the like. A polynucleotide can be single- or double-stranded, and can be complementary to the sense or antisense strand of a gene sequence, for example. A polynucleotide can hybridize with a complementary portion of a target polynucleotide to form a duplex, which can be a homoduplex or a heteroduplex. The length of a polynucleotide is not limited in any respect. Linkages between nucleotides can be internucleotide-type phosphodiester linkages, or any other type of linkage. A "polynucleotide sequence" refers to the sequence of nucleotide monomers along the polymer. A "polynucleotide" is not limited to any particular length or range of nucleotide sequence, as the term "polynucleotide" encompasses polymeric forms of nucleotides of any length. A polynucleotide can be produced by biological means (e.g., enzymatically), or synthesized using an enzyme-free system. A polynucleotide can be enzymatically extendable or enzymatically non-extendable.

Polynucleotides that are formed by 3'-5' phosphodiester linkages are said to have 5'-ends and 3'-ends because the nucleotide monomers that are reacted to make the polynucleotide are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right.

As used herein, it is not intended that the term "polynucleotides" be limited to naturally occurring polynucleotides sequences or polynucleotide structures, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention. Non-limiting examples of such unnatural structures include non-ribose sugar backbones, 3'-5' and 2'-5' phosphodiester linkages, internucleotide inverted linkages (e.g., 3'-3' and 5'-5'), and branched structures. Furthermore, unnatural structures also include unnatural internucleotide analogs, e.g., peptide nucleic acids (PNAs), locked nucleic acids (LNAs), $C_1$-$C_4$ alkylphosphonate linkages such as methylphosphonate, phosphoramidate, $C_1$-$C_6$ alkyl-phosphotriester, phosphorothioate and phosphorodithioate internucleotide linkages. Furthermore, a polynucleotide can be composed entirely of a single type of monomeric subunit and one type of linkage, or can be composed of mixtures or combinations of different types of subunits and different types of linkages (a polynucleotide can be a chimeric molecule). As used herein, a polynucleotide analog retains the essential nature of natural polynucleotides in that they hybridize to a single-stranded nucleic acid target in a manner similar to naturally occurring polynucleotides.

As used herein, the term "sequence of a polynucleotide," "nucleic acid sequence," "polynucleotide sequence", or equivalent and similar phrases refer to the order of nucleotides in the polynucleotide. In some cases, a "sequence" refers more specifically to the order and identity of the bases that are each attached to the nucleotides. A sequence is typically read (written) in the 5' to 3' direction. Unless otherwise indicated, a particular polynucleotide sequence of the invention optionally encompasses complementary sequences, in addition to the sequence explicitly indicated.

As used herein, the terms "amplification," "amplifying" or the like refer generally to any process that results in an increase in the copy number of a molecule or set of related molecules. As it applies to polynucleotide molecules, amplification means the production of multiple copies of a polynucleotide molecule, or a portion of a polynucleotide molecule, typically starting from a small amount of a polynucleotide (e.g., a viral genome), where the amplified material (e.g., a viral PCR amplicon) is typically detectable. Amplification of polynucleotides encompasses a variety of chemical and enzymatic processes. The generation of multiple DNA copies from one or a few copies of a template DNA molecule during a polymerase chain reaction (PCR), a strand displacement amplification (SDA) reaction, a transcription mediated amplification (TMA) reaction, a nucleic acid sequence-based amplification (NASBA) reaction, or a ligase chain reaction (LCR) are forms of amplification. Amplification is not limited to the strict duplication of the starting molecule. For example, the generation of multiple cDNA molecules from a limited amount of viral RNA in a sample using RT-PCR is a form of amplification. Furthermore, the generation of multiple RNA molecules from a single DNA molecule during the process of transcription is also a form of amplification.

In some embodiments, amplification is optionally followed by additional steps, for example, but not limited to, labeling, sequencing, purification, isolation, hybridization, size resolution, expression, detecting and/or cloning.

As used herein, the term "polymerase chain reaction" (PCR) refers to a method for amplification well known in the art for increasing the concentration of a segment of a target polynucleotide in a sample, where the sample can be a single polynucleotide species, or multiple polynucleotides. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers. Reverse transcriptase PCR (RT-PCR) is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Methods for a wide variety of PCR applications are widely known in the art, and described in many sources, for example, Ausubel et al. (eds.), Current Protocols in Molecular Biology, Section 15, John Wiley & Sons, Inc., New York (1994).

As used herein, the expression "asymmetric PCR" refers to the preferential PCR amplification of one strand of a DNA target by adjusting the molar concentration of the primers in a primer pair so that they are unequal. An asymmetric PCR reaction produces a predominantly single-stranded product and a smaller quantity of a double-stranded product as a result of the unequal primer concentrations. As asymmetric PCR proceeds, the lower concentration primer is quantitatively incorporated into a double-stranded DNA amplicon, but the higher concentration primer continues to prime DNA synthesis, resulting in continued accumulation of a single stranded product.

As used herein, the term "DNA-dependent DNA polymerase" refers to a DNA polymerase enzyme that uses deoxyribonucleic acid (DNA) as a template for the synthesis of a complementary and antiparallel DNA strand. Thermostable DNA-dependent DNA polymerases find use in PCR amplification reactions. Suitable reaction conditions (and reaction buffers) for DNA-dependent DNA polymerase enzymes, and indeed any polymerase enzyme, are widely known in the art, and are described in numerous sources (see, e.g., Ausubel et al. (eds.), Current Protocols in Molecular Biology, Vol. 1-4, John Wiley & Sons, Inc., New York [1994; supplemented through September 2004]). Reaction buffers for DNA-dependent DNA polymerase enzymes can comprise, for example, free deoxyribonucleoside triphosphates, salts and buffering agents.

As used herein, the term "DNA-dependent RNA polymerase" refers to an RNA polymerase enzyme that uses deoxyribonucleic acid (DNA) as a template for the synthesis of an RNA strand. The process mediated by a DNA-dependent RNA polymerase is commonly referred to as "transcription."

As used herein, the term "RNA-dependent DNA polymerase" refers to a DNA polymerase enzyme that uses ribonucleic acid (RNA) as a template for the synthesis of a complementary and antiparallel DNA strand. The process of generating a DNA copy of an RNA molecule is commonly termed "reverse transcription," or "RT," and the enzyme that accomplishes that is a "reverse transcriptase." Some naturally-occurring and mutated DNA polymerases also possess reverse transcription activity.

As used herein, the term "thermostable," as applied to an enzyme, refers to an enzyme that retains its biological activity at elevated temperatures (e.g., at 55° C. or higher), or retains its biological activity following repeated cycles of heating and cooling. Thermostable DNA polymerases find particular use in PCR amplification reactions.

As used herein, the term "primer" refers to an enzymatically extendable oligonucleotide, generally with a defined sequence that is designed to hybridize in an antiparallel manner with a complementary, primer-specific portion of a target sequence. Further, a primer can initiate the polymerization of nucleotides in a template-dependent manner to yield a polynucleotide that is complementary to the target polynucleotide. The extension of a primer annealed to a target uses a suitable DNA or RNA polymerase in suitable reaction conditions. One of skill in the art knows well that polymerization reaction conditions and reagents are well established in the art, and are described in a variety of sources.

A primer nucleic acid does not need to have 100% complementarity with its template subsequence for primer elongation to occur; primers with less than 100% complementarity can be sufficient for hybridization and polymerase elongation to occur. Optionally, a primer nucleic acid can be labeled, if desired. The label used on a primer can be any suitable label, and can be detected by, for example, by spectroscopic, photochemical, biochemical, immunochemical, chemical, or other detection means.

As used herein, the expression "amplification primer" refers to a primer that is generally in molar excess relative to its target polynucleotide sequence, and primes template-dependent enzymatic DNA synthesis and amplification of the target sequence (and sequence downstream from the site of hybridization) to yield a single-stranded amplicon.

As used herein, the expression "amplifilcation primer pair" refers to a set of two primers that are generally in molar excess relative to their target polynucleotide sequence, and together prime template-dependent enzymatic DNA synthesis and amplification of the target sequence to yield a double-stranded amplicon.

As used herein, the term "amplicon" refers to a polynucleotide molecule (or collectively the plurality of molecules) produced following the amplification of a particular target nucleic acid. The amplification method used to generate the amplicon can be any suitable method, most typically, for example, by using a PCR methodology. An amplicon is typically, but not exclusively, a DNA amplicon. An amplicon can be single-stranded or double-stranded, or in a mixture thereof in any concentration ratio.

As used herein, the expression "real-time detection of amplicon accumulation" refers to the detection of, and typically the quantitation thereof, of a specific amplicon or amplicons, as the amplicon(s) is/are being produced (typically by PCR) without the need for a detection or quantitation step following the completion of the amplification. The terms "real-time PCR" or "kinetic PCR" refer to real-time detection and/or quantitation of amplicon generated in a PCR.

A common method for real-time detection of amplicon accumulation is by a 5'-nuclease assay, also termed a fluorogenic 5'-nuclease assay, e.g., a TaqMan analysis; see, Holland et al., Proc. Natl. Acad. Sci. USA 88:7276-7280 (1991); and Heid et al., Genome Research 6:986-994 (1996). In the TaqMan PCR procedure, two oligonucleotide primers are used to generate an amplicon specific to the PCR reaction. A third oligonucleotide (the TaqMan probe) is designed to hybridize with a nucleotide sequence in the amplicon located between the two PCR primers. The probe may have a structural feature that renders it non-extendable by the DNA polymerase used in the PCR reaction, and is typically (but not necessarily) colabeled with a fluorescent reporter dye and a quencher moiety in close proximity to one another. The emission from the reporter dye is quenched by the quenching moiety when the fluor and quencher are in close proximity, as they are on the probe. In some cases, the probe may be labeled with only a fluorescent reporter dye or another detectable moiety.

The TaqMan PCR reaction uses a thermostable DNA-dependent DNA polymerase that possesses a 5'-3' nuclease activity. During the PCR amplification reaction, the 5'-3' nuclease activity of the DNA polymerase cleaves the labeled probe that is hybridized to the amplicon in a template-dependent manner. The resultant probe fragments dissociate from the primer/template complex, and the reporter dye is then free from the quenching effect of the quencher moiety. Approximately one molecule of reporter dye is liberated for each new amplicon molecule synthesized, and detection of the unquenched reporter dye provides the basis for quantitative interpretation of the data, such that the amount of released fluorescent reporter dye is directly proportional to the amount of amplicon template.

One measure of the TaqMan assay data is typically expressed as the threshold cycle ($C_T$). Fluorescence levels are recorded during each PCR cycle and are proportional to the amount of product amplified to that point in the amplification reaction. The PCR cycle when the fluorescence signal is first recorded as statistically significant, or where the fluorescence signal is above some other arbitrary level (e.g., the arbitrary fluorescence level, or AFL), is the threshold cycle ($C_T$).

Protocols and reagents for 5'-nuclease assays are well known to one of skill in the art, and are described in various sources. For example, 5'-nuclease reactions and probes are described in U.S. Pat. No. 6,214,979, entitled "HOMOGENEOUS ASSAY SYSTEM," issued Apr. 10, 2001 to Gelfand et al.; U.S. Pat. No. 5,804,375, entitled "REACTION MIXTURES FOR DETECTION OF TARGET NUCLEIC ACIDS," issued Sep. 8, 1998 to Gelfand et al.; U.S. Pat. No. 5,487,972, entitled "NUCLEIC ACID DETECTION BY THE 5'-3' EXONUCLEASE ACTIVITY OF POLYMERASES ACTING ON ADJACENTLY HYBRIDIZED OLIGONUCLEOTIDES," issued Jan. 30, 1996 to Gelfand et al.; and U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., all of which are incorporated by reference.

Variations in methodologies for real-time amplicon detection are also known, and in particular, where the 5'-nuclease probe is replaced by double-stranded DNA intercalating dye resulting in fluorescence that is dependent on the amount of double-stranded amplicon that is present in the amplification reaction. See, for example, U.S. Pat. No. 6,171,785, entitled "METHODS AND DEVICES FOR HOMOGENOUS NUCLEIC ACID AMPLIFICATION AND DETECTION," issued Jan. 9, 2001 to Higuchi; and U.S. Pat. No. 5,994,056, entitled "HOMOGENEOUS METHODS FOR NUCLEIC ACID AMPLIFICATION AND DETECTION," issued Nov. 30, 1999 to Higuchi, each of which are incorporated by reference.

TaqMan® PCR can be performed using commercially available kits and equipment, such as, for example, ABI PRISM® 7700 Sequence Detection System (Applied Biosystems, Foster City, Calif.), or LightCycler® (Roche Applied Sciences, Mannheim, Germany). In a preferred embodiment, the 5' nuclease assay procedure is run on a real-time quantitative PCR device such as the ABI PRISM® 7700 Sequence Detection System. The system consists of a thermocycler, laser, charge-coupled device (CCD), camera and computer. The system amplifies samples in a 96-well microtiter plate format on a thermocycler. During amplification, laser-induced fluorescent signal is collected in real-time through fiber optics cables for all 96 wells, and detected at the CCD camera. The system includes software for running the instrument and for analyzing the data. This ABI PRISM® system has the added benefit of temperature control down to temperatures as low as 20° C., thereby permitting melting curve analysis.

Devices that are able to excite and detect emissions on two different channels from the same reaction vessel also find use with the invention. For example, the EXAMPLES described below utilize the COBAS™ TaqMan® 48 Analyzer from Roche Molecular Diagnostics (Roche Molecular Systems, Inc, Pleasanton, Calif.). It is not intended that the invention be limited to the use of an particular apparatus.

As used herein, the terms "hybridization" and "annealing" and the like are used interchangeably and refer to the base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotide molecules is typically base specific, e.g., A/T and G/C, by Watson/Crick and/or Hoogsteen-type hydrogen bonding. It is not a requirement that two polynucleotides have 100% complementarity over their full length to achieve hybridization. In some aspects, a hybridization complex can form from intermolecular interactions, or alternatively, can form from intramolecular interactions.

As used herein, the phrases "specifically hybridize," "specific hybridization" and the like refer to hybridization resulting in a complex where the annealing pair show complementarity, and preferentially bind to each other to the exclusion of other potential binding partners in the hybridization reaction. It is noted that the term "specifically hybridize" does not require that a resulting hybridization complex have 100% complementarity; hybridization complexes that have mismatches can also specifically hybridize and form a hybridization complex. The degree of specificity of the hybridization can be measured using a distinguishing hybridization property, e.g., the melting temperature of the hybridization complex ($T_m$).

As used herein, the phrase "conditions wherein base-pairing occurs" refers to any hybridization conditions that permit complementary polynucleotides or partially complementary polynucleotides to form a stable hybridization complex.

As used herein, the terms "stringent," "stringent conditions," "high stringency" and the like denote hybridization conditions of generally low ionic strength and high temperature, as is well known in the art. See, e.g., Sambrook et al., *Molecular Cloning: A Laboratory Manual*, 3$^{rd}$ Ed., Cold Spring Harbor Laboratory Press, Cold Spring Harbor, N.Y. (2001); *Current Protocols in Molecular Biology* (Ausubel et al., ed., J. Wiley & Sons Inc., New York, 1997), which are incorporated herein by reference. Generally, stringent conditions are selected to be about 5-30° C. lower than the thermal melting point ($T_m$) for the hybridization complex comprising the specified sequence at a defined ionic strength and pH. Alternatively, stringent conditions are selected to be about 5-15° C. lower than the $T_m$ for the specified sequence at a defined ionic strength and pH. The $T_m$ is the temperature (under defined ionic strength, pH and nucleic acid concentration) at which 50% of the hybridization complexes comprising complementary (or partially complementary) polynucleotides become dissociated.

As used herein, the expression "low stringency" denotes hybridization conditions of generally high ionic strength and lower temperature. Under low stringency hybridization conditions, polynucleotides with imperfect complementarity can more readily form hybridization complexes.

As used herein, the terms "complementary" or "complementarity" are used in reference to antiparallel strands of polynucleotides related by the Watson-Crick and Hoogsteen-type base-pairing rules. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands (no mismatches in the polynucleotide duplex). However, complementarity need not be perfect; stable duplexes, for example, may contain mismatched base pairs or unmatched bases. The terms "partial complementarity," "partially complementary," "incomplete complementarity" or "incompletely complementary" and the like refer to any alignment of bases between antiparallel polynucleotide strands that is less than 100% perfect (e.g., there exists at least one mismatch or unmatched base in the polynucleotide duplex). For example, the alignment of bases between the antiparallel polynucleotide strands can be at least 99%, 95%, 90%, 85%, 80%, 75%, 70%, 65%, 60%, 55%, or 50%, or any value between.

Furthermore, a "complement" of a target polynucleotide refers to a polynucleotide that can combine (e.g., hybridize) in an antiparallel association with at least a portion of the target polynucleotide. The antiparallel association can be intramolecular, e.g., in the form of a hairpin loop within a nucleic acid molecule, or intermolecular, such as when two or more single-stranded nucleic acid molecules hybridize with one another.

As used herein, "target", "target polynucleotide", and "target sequence" and the like refer to a specific polynucleotide sequence that is the subject of hybridization with a complementary polynucleotide, e.g., a labelled probe or a DNA polymerase primer. The hybridization complex formed as a result of the annealing of a polynucleotide with its target is termed a "target hybridization complex." The hybridization complex can form in solution (and is therefore soluble), or one or more component of the hybridization complex can be affixed to a solid phase (e.g., to a dot blot, affixed to a bead system to facilitate removal or isolation of target hybridization complexes, or in a microarray). The structure of the target sequence is not limited, and can be composed of DNA, RNA, analogs thereof, or combinations thereof, and can be single-stranded or double-stranded. A target polynucleotide can be derived from any source, including, for example, any living or once living organism, including but not limited to prokaryote, eukaryote, plant, animal, and virus, as well as synthetic and/or recombinant target sequences. For example, as described herein, a PCR amplicon derived from viral genomic sequence can serve as a target.

In some aspects, the target polynucleotide in a hybridization complex serves as a "template," where an extendable polynucleotide primer binds to the template and initiates nucleotide polymerization using the base sequence of the template as a pattern for the synthesis of a complementary polynucleotide.

As used herein, the term "probe" refers typically to a polynucleotide that is capable of hybridizing to a target nucleic acid of interest. Typically, but not exclusively, a probe is associated with a suitable label or reporter moiety so that the probe (and therefore its target) can be detected, visualized, measured and/or quantitated. Detection systems for labelled probes include, but are not limited to, the detection of fluorescence, fluorescence quenching (e.g., when using a FRET pair detection system), enzymatic activity, absorbance, molecular mass, radioactivity, luminescence or binding properties that permit specific binding of the reporter (e.g., where the reporter is an antibody). In some embodiments, a probe can be an antibody, rather than a polynucleotide, that has binding specificity for a nucleic acid nucleotide sequence of interest. It is not intended that the present invention be limited to any particular probe label or probe detection system. The source of the polynucleotide used in the probe is not limited, and can be produced synthetically in a non-enzymatic system, or can be a polynucleotide (or a portion of a polynucleotide) that is produced using a biological (e.g., enzymatic) system (e.g., in a bacterial cell).

Typically, a probe is sufficiently complementary to a specific target sequence contained in a nucleic acid to form a stable hybridization complex with the target sequence under a selected hybridization condition, such as, but not limited to, a stringent hybridization condition. A hybridization assay carried out using the probe under sufficiently stringent hybridization conditions permits the selective detection of a specific target sequence.

As used herein, the terms "label" or "reporter," in their broadest sense, refer to any moiety or property that is detectable, or allows the detection of, that which is associated with it. For example, a polynucleotide that comprises a label is detectable (and in some aspects is referred to as a probe). Ideally, a labeled polynucleotide permits the detection of a hybridization complex that comprises the polynucleotide. In some aspects, e.g., a label is attached (covalently or non-covalently) to a polynucleotide. In various aspects, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels vary widely in their structures and their mechanisms of action.

Examples of labels include, but are not limited to, fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg.). Dyes of the cyanine family include, e.g., Cy2, Cy3, Cy5, Cy 5.5 and Cy7, and are commercially available from, e.g., Amersham Biosciences Corp. (Piscataway, N.J., USA).

As used herein, the term "FRET" (fluorescent resonance energy transfer) and equivalent terms refers generally to a dynamic distance-dependent interaction between electron states of two dye molecules in which energy is transferred from a donor molecule to an acceptor molecule without emission of a photon from the donor molecule. The efficiency of FRET is dependent on the inverse of the intermolecular separation between the dyes, making it useful over distances comparable with the dimensions of biological macromolecules. Generally, FRET allows the imaging, kinetic analysis and/or quantitation of colocalizing molecules or conformational changes in a single molecule with spatial resolution beyond the limits of conventional optical microscopy. In general, FRET requires, (a) the donor and acceptor molecules must be in close proximity (typically, e.g., 10-100 Å), (b) the absorption spectrum of the acceptor must overlap the fluorescence emission spectrum of the donor, and (c) the donor and acceptor transition dipole orientations must be approximately parallel.

In most FRET applications, the donor and acceptor dyes are different, in which case FRET can be detected by the appearance of sensitized fluorescence of the acceptor or by quenching of donor fluorescence. In some cases, the donor and acceptor are the same, and FRET can be detected by the resulting fluorescence depolarization. Use of a single donor/acceptor molecule in a FRET system is described, for example, in Published US Patent Application No. 2004/0096926, by Packard and Komoriya, published May 20, 2004, entitled "COMPOSITIONS FOR THE DETECTION OF ENZYME ACTIVITY IN BIOLOGICAL SAMPLES AND METHODS OF USE THEREOF," which is hereby incorporated by reference.

FRET has become an important technique for investigating a variety of biological phenomena that are characterized by changes in molecular proximity. FRET techniques are now pervasive in many biological laboratories, and have been adapted for use in a variety of biological systems, including but not limited to, detection of nucleic acid hybridization, real-time PCR assays and SNP detection, structure and conformation of proteins, spatial distribution and assembly of protein complexes, receptor/ligand interactions, immunoassays, probing interactions of single molecules, structure and conformation of nucleic acids, primer-extension assays for detecting mutations, automated DNA sequencing, distribution and transport of lipids, membrane fusion assays (lipid-mixing assays of membrane fusion), membrane potential sensing, fluorogenic protease substrates, and indicators for cyclic AMP and zinc.

As used herein, the term "FRET donor" refers typically to a moiety that produces a detectable emission of radiation, e.g., fluorescent or luminescent radiation, that can be transferred to a suitable FRET acceptor in sufficient proximity. The expression "FRET donor" can be used interchangeably with "FRET label" or "FRET label moiety."

As used herein, the terms "quencher," "quencher moiety," "acceptor," "acceptor moiety" and "light emission modifier" and similar and equivalent terms refer generally to a moiety that reduces and/or is capable of reducing the detectable emission of radiation, for example but not limited to, fluorescent or luminescent radiation, from a source that would otherwise have emitted this radiation. Generally, a quencher refers to any moiety that is capable of reducing light emission. The degree of quenching is not limited, per se, except that a quenching effect should minimally be detectable by whatever detection instrumentation is used. In some aspects, a quencher reduces the detectable radiation emitted by the source by at least 50%, alternatively by at least 80%, and alternatively and most preferably by at least 90%.

In some embodiments, the quencher results in a reduction in the fluorescence emission from a donor, and thus the donor/quencher forms a FRET pair, and the quencher is termed a "FRET quencher," or "FRET acceptor," and the donor is a "FRET donor."

It is not intended that that the term "quencher" be limited to FRET quenchers. For example, quenching can involve any type of energy transfer, including but not limited to, photo-electron transfer, proton coupled electron transfer, dimer formation between closely situated fluorophores, transient excited state interactions, collisional quenching, or formation of non-fluorescent ground state species. In some embodiments, a quencher refers to a molecule that is capable of reducing light emission. There is no requirement for a spectral overlap between the fluorophore and the quencher. As used herein, "quenching" includes any type of quenching, including dynamic (Förster-Dexter energy transfer, etc.), and static (ground state complex). Alternatively still, a quencher can dissipate the energy absorbed from a fluorescent dye in a form other than light, e.g., as heat.

In some embodiments, some quenchers can re-emit the energy absorbed from a FRET donor at a wavelength or using a signal type that is distinguishable from the FRET donor emission, and at a wavelength or signal type that is characteristic for that quencher, and thus, in this respect, a quencher can also be a "label."

For general discussion on the use of fluorescence probe systems, see, for example, *Principles of Fluorescence Spectroscopy*, by Joseph R. Lakowicz, Plenum Publishing Corporation, 2nd edition (Jul. 1, 1999) and *Handbook of Fluorescent Probes and Research Chemicals*, by Richard P. Haugland, published by Molecular Probes, 6th edition (1996).

As used herein, the expressions "soluble acceptor," "soluble quencher," "soluble light emission modifier" or the like refer to an acceptor moiety that is not attached to any other molecule, and is largely soluble or otherwise not bound to any other molecule or solid phase. For example, some thiazine dyes e.g., new methylene blue, can be used as soluble quenchers. In some embodiments, the soluble quencher is a soluble FRET quencher, where the soluble FRET quencher is part of a functional FRET pair, also comprising a FRET donor.

As used herein, the terms "thiazine dye" and "thiazin dye" (these terms are synonymous and are used interchangeably in the art) refer to any of a class of organic chemical compounds containing a ring composed of one sulfur atom, one nitrogen atom, and four carbon atoms. Examples of thiazine dyes that can be used as soluble quenchers include, e.g., methylene blue ($C_{16}H_{18}ClN_3S$), methylene green ($C_{16}H_{17}ClN_4O_2S$), thionin ($C_{12}H_{10}ClN_3S$), sym-dimethylthionin, toluidine blue O ($C_{15}H_{16}N_3SCl$), new methylene blue ($C_{18}H_{22}ClN_3S$), methylene violet bernthsen, azure A ($C_{14}H_{14}ClN_3S$), azure B ($C_{15}H_{16}ClN_3S$), azure C, 1,9-dimethylmethylene blue, toluidine blue O, and methylene violet bernthsen. The structures of some of these compounds are shown in FIG. 7.

Further detailed description of soluble light emission modifiers and the uses thereof is found in cofiled U.S. patent application Ser. No. 11/474,062, filed on Jun. 23, 2006, entitled "LIGHT EMISSION MODIFIERS AND THEIR USES IN NUCLEIC ACID DETECTION, AMPLIFICATION AND ANALYSIS," by Gupta and Will, the entire content of which is hereby incorporated by reference in its entirety for all purposes.

As used herein, the expression "FRET pair" and similar and equivalent terms refers to the pairing of a FRET donor moiety and a FRET acceptor moiety, such that FRET is observed when the donor and the acceptor are within suitable proximity to each other. Generally, but not exclusively, the donor moiety and the acceptor moiety are attached to various molecules of interest (e.g., polynucleotide probes).

A wide variety of dyes, fluors, quenchers, and fluorescent proteins, along with other reagents and detection/imaging instrumentation have been developed for use in FRET analysis and are widely commercially available. One of skill in the art recognizes appropriate FRET protocols, reagents and instrumentation to use for any particular analysis.

Molecules commonly used in FRET include, for example but not limited to, fluorescein, FAM, JOE, rhodamine, R6G, TAMRA, ROX, DABCYL, and EDANS. Whether a fluorescent dye is a label or a quencher is defined by its excitation and emission spectra, and also by the fluorescent dye with which it is paired. For example, FAM is most efficiently excited by light with a wavelength of 488 nm, and emits light with a spectrum of 500 to 650 nm, and an emission maximum of 525 nm. FAM is a suitable donor label for use with, e.g., TAMRA as a quencher, which has at its excitation maximum 514 nm. Examples of non-fluorescent or dark quenchers that dissipate energy absorbed from a fluorescent dye include the Black Hole Quenchers™ marketed by Biosearch Technologies, Inc. (Novato, Calif., USA). The Black Hole Quenchers™ are structures comprising at least three radicals selected from substituted or unsubstituted aryl or heteroaryl compounds, or combinations thereof, wherein at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Examples of quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

As used herein, a "moiety" or "group" refers to a portion or a constituent part of a larger molecule or complex. For example, an oligonucleotide probe can comprise a label moiety.

As used herein, a "distinguishing hybridization property" refers to any property of a hybridization complex that can be used to distinguish one complex from another complex or any number of other complexes. One single-stranded nucleic acid molecule can participate in a large number of hybridization complexes with various target molecules, where the number, positions and types of nucleotide base mismatches (if any) vary. Many methods can be employed for distinguishing between these complexes, for example but not limited to, melting analysis (e.g., $T_m$ analysis), HMA (heteroduplex mobility analysis; White et al., J Clin Microbiol (2000) 38:477-482), DHPLC (denaturing HPLC), CFLP (cleavase fragment length polymorphism; Marshall et al., J Clin Microbiol (1997) 35:3156-3162), TGCE (thermal gradient capillary electrophoresis); SURVEYOR™ nuclease mutation detection kits, SSCP (single strand conformation polymorphism), etc.

As used herein, a "temperature-dependent hybridization property" refers to any quantitative temperature-dependent characteristic of a hybridization complex. For example, the melting temperature ($T_m$) is a temperature-dependent distinguishing hybridization property. However, a temperature-dependent hybridization property is not limited to $T_m$. For example, the temperature at which 25% of a population of double-stranded polynucleotides or nucleobase oligomers (e.g., hybridization complexes), in homoduplexes or heteroduplexes, become dissociated into single strands ($T_{25}$) is also a defining characteristic of the hybridization complex. Similarly, the temperature at which 75% of a population of double-stranded polynucleotides or nucleobase oligomers (e.g., hybridization complexes), in homoduplexes or heteroduplexes, become dissociated into single strands ($T_{75}$) is also a defining property of the hybridization complex. Alternatively, the percentage of dissociation of a hybridization complex at any defined temperature is a quantitative temperature dependent hybridization property. Alternatively still, an "annealing curve" (as opposed to a melting curve) can be used to characterize a hybridization complex. In the annealing curve analysis, the behavior of the target and the probe polynucleotide strands is observed with decreasing temperature (as opposed to increasing temperature as used in a melting curve analysis). Methods for measuring the extent of dissociation or annealing of a hybridization complex are well known to one of skill in the art.

As used herein, the term "$T_m$" is used in reference to the "melting temperature." The melting temperature is the temperature at which one half of a population of double-stranded polynucleotides or nucleobase oligomers (e.g., hybridization complexes), in homoduplexes or heteroduplexes, become dissociated into single strands. The prediction of a $T_m$ of a duplex polynucleotide takes into account the base sequence as well as other factors including structural and sequence characteristics and nature of the oligomeric linkages. Methods for predicting and experimentally determining $T_m$ are known in the art. For example, a $T_m$ is traditionally determined by a melting curve, wherein a duplex nucleic acid molecule is heated in a controlled temperature program, and the state of association/dissociation of the two single strands in the duplex is monitored and plotted until reaching a temperature where the two strands are completely dissociated. The $T_m$ is read from this melting curve. Alternatively, a $T_m$ can be determined by an annealing curve, wherein a duplex nucleic acid molecule is heated to a temperature where the two strands are completely dissociated. The temperature is then lowered in a controlled temperature program, and the state of association/dissociation of the two single strands in the duplex is monitored and plotted until reaching a temperature where the two strands are completely annealed. The $T_m$ is read from this annealing curve.

As used herein, the term "sample" is used in its broadest sense, and refers to any material subject to analysis. The term "sample" refers typically to any type of material of biological origin, for example, any type of material obtained from animals or plants. A sample can be, for example, any fluid or tissue such as blood or serum, and furthermore, can be human blood or human serum. A sample can be cultured cells or tissues, cultures of microorganisms (prokaryotic or eukaryotic), or any fraction or products produced from or derived from biological materials (living or once living). Optionally, a sample can be purified, partially purified, unpurified, enriched or amplified. Where a sample is purified or enriched, the sample can comprise principally one component, e.g., nucleic acid. More specifically, for example, a purified or amplified sample can comprise total cellular RNA, total cellular MRNA, cDNA, cRNA, or an amplified product derived there from.

The sample used in the methods of the invention can be from any source, and is not limited. Such sample can be an amount of tissue or fluid isolated from an individual or individuals, including, but not limited to, for example, skin, plasma, serum, whole blood, blood products, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc.

As used herein, the term "genome" refers to the total genetic information or hereditary material possessed by an organism (including viruses), i.e., the entire genetic complement of an organism or virus. The size of a genome is generally given as its total number of nucleotides or bases (when describing single-stranded genomes) or basepairs (when describing double-stranded genomes). A genome can comprise RNA or DNA. A genome can be linear, circular, and/or reside on discrete units such as chromosomes.

As used herein, the expression "sequence heterogeneity" refers to base sequence divergence between two or more homologous nucleotide sequences derived from different sources. Sequence divergence can be reflected in base pair incongruity (mismatches), gaps, insertions and/or genomic rearrangements. As used herein, one HCV genome, or a portion of the genome, can be aligned with a second (or more) HCV genome (or portion thereof) and analyzed for sequence heterogeneity. For example, a collection of viral genomes show sequence heterogeneity if they collectively show sequence divergence in a particular domain, e.g., in the 5'-UTR, or in a portion of the 5'-UTR.

As used herein, the expression "hepatitis C virus type" refers to the categorization of a hepatitis C virus (HCV) based on its genomic organization (e.g., phylogenetic analysis). The categorization of an HCV isolate into a particular type category reflects its genomic relatedness to other HCV isolates and its relatively lesser relatedness to other HCV isolates. As used herein, HCV typing nomenclature is consistent with the widely adopted nomenclature proposed by Simmonds et al (1994) Letter, Hepatology 19:1321-1324. See, also, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England.). The system of Simmonds et al (1994) places the known HCV isolates into one of eleven (11) HCV genotypes, namely genotypes 1 through 11. Each genotype is further subdivided into groupings termed subtypes that reflect relatedness among strains of the same genotype. An HCV subtype is written by a lowercase roman letter following the genotype, e.g., subtype 1a, subtype 1c, subtype 6a, etc. Genetic variants found within an individual isolate are termed quasispecies. Approximately 78 HCV subtypes encompassing all 11 genotypes are known worldwide; the number of subtypes is not static; as more HCV isolates are studied and sequenced, it is likely that additional subtypes (and possibly genotypes) may be recognized.

As used herein, the term "virus types" can refer to either genotypes or subtypes. It is noted that as used herein, the term "HCV type" can mean HCV genotype or HCV subtype. As used herein, the term "HCV typing" means assigning the experimental (e.g., unknown type) HCV to a known genotype (e.g., 1, 2, 3, 4, 5 or 6, or a subset thereof) or assigning the experimental HCV to a known subtype (e.g., 1a, 1b, 1c, 2a, 2b, 2c, etc., or a subset thereof). In contrast, it is also noted that as commonly used in the art, the term "HCV genotyping" most frequently refers to assigning an HCV to one of any subtype of HCV, e.g., most typically, 1a, 1b, 1c, 2a, 2b, 2c, etc. However, as used herein, the term "genotyping" refers to assignment only to 1, 2, 3, 4, 5 or 6.

Some reports (see, e.g., Robertson et al., (1998) Arch. Virol., 143(12):2493-2503) suggest that viral genomic organization is best represented by the creation of viral clades, reflecting the observation that some HCV genotypes are more closely related to each other than to other HCV genotypes. In this system, clades 1, 2, 4 and 5 correspond to genotypes 1, 2, 4 and 5, while clade 3 comprises genotypes 3 and 10, and clade 6 comprises genotypes 6, 7, 8, 9 and 11. The description of the present invention herein does not use the clade nomenclature.

As used herein, the expression "derived from" refers to a component that is isolated from or made using a specified sample, molecule, organism or information from the specified molecule or organism. For example, a nucleic acid molecule that is derived from a hepatitis C virus can be a molecule of the HCV genome, or alternatively, a transcript from the HCV genome.

As used herein, the expression "viral load," "viral burden," "viral copy number" and equivalent or similar expressions refer to the quantitative evaluation of a virus genome in a sample. A viral load can be expressed as the number of viral particles (e.g., virion) per unit of sample volume. Alternatively, a viral load can be expressed as the number of viral genome particles in a sample per unit of volume. For example, the viral load of an HCV in a sample can be expressed as the number of RNA genome molecules per unit of sample volume.

As used herein, the terms "subsequence," "fragment," "portion" and the like refer to any portion of a larger sequence (e.g., a polynucleotide or polypeptide sequence), up to and including the complete sequence. The minimum length of a subsequence is generally not limited, except that a minimum length may be useful in view of its intended function. For example, a polynucleotide portion can be amplified from a viral genome to produce an amplicon, which in turn can be used in a hybridization reaction that includes a polynucleotide probe. Thus, in this case, the amplified portion should be long enough to specifically hybridize to a polynucleotide probe. Portions of polynucleotides can be any length, for example, at least 5, 10, 15, 20, 25, 30, 40, 50, 75, 100, 150 or 200 nucleotides or more in length.

As used herein, the term "monitor" refers to periodic or continuous surveillance, testing, data collecting and/or quantitation. Monitoring can be automated, and the information (e.g., a dataset) gathered during the monitoring can be printed or can be compiled as a computer readable and/or computer storable format.

As used herein, the term "correlate" refers to making a relationship between two or more variables, values or entities. If two variables correlate, the identification of one of those variables can be used to determine the value of the remaining variable.

As used herein, the term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, as well as any other components. In some embodiments, the present invention provides kits for "closed-tube" HCV typing employing RT-PCR. These kits can include, for example but not limited to, reagents for sample collection (e.g., the collection of a blood sample), reagents for the collection and purification of RNA from blood, a reverse transcriptase, primers suitable for reverse transcription and first strand and second strand cDNA synthesis to produce an HCV amplicon, a thermostable DNA-dependent DNA polymerase and free deoxyribonucleotide triphosphates. In some embodiments, the enzyme comprising reverse transcriptase activity and thermostable DNA-dependent DNA polymerase activity are the same enzyme, e.g., *Thermus* sp. ZO5 polymerase or *Thermus thermophilus* polymerase.

BRIEF DESCRIPTION OF THE FIGURES

FIG. 2 provides a table describing HCV typing nomenclature.

FIG. 3 provides a table showing the percentages of nucleotide sequence identity between various HCV subtypes in a 222-nucleotide segment derived from the NS5 region at positions 7975 to 8196 of the prototype HCV viral genome.

FIG. 4 provides a table listing various HCV subtypes and examples of known isolates.

FIG. 5 provides a table listing various HCV types, and the consensus nucleotide sequences of a 33 nucleotide domain in the 5'-UTR region of each of the respective subtypes.

FIG. 6 provides a table listing examples of HCV typing probes, their length (in nucleotides), and their respective base sequences. A legend describing the symbols used to denote non-standard nucleotides and labels is shown at bottom.

FIG. 25 provides a side-by-side comparison of the second derivative plots of FIGS. 22 and 24, read using the FAM channel and HEX channel, respectively. The $T_m$ values for each probe and each HCV type combination are indicated on the graphs.

DETAILED DESCRIPTION

The typing of an HCV isolate (for example, in a sample from a patient) is a valuable clinical tool in determining an appropriate course of therapy. Knowing the type (genotype and/or subtype) of the HCV in an infection also has other benefits, including epidemiological analysis (e.g., determining the source and/or spread of a particular HCV outbreak).

Current methods for HCV typing face various limitations, as discussed above. For the purpose of providing improved methods for HCV typing to overcome present limitations in the art and fulfill currently unmet needs, the present application provides novel compositions and novel methods for HCV typing analysis, where the methods described herein use combinations of probes to make an HCV type assignment, where the technique is able to differentiate at least five HCV types (genotypes or subtypes). The combinations of probes can be used simultaneously in a single typing analysis. The compositions and methods of the present invention can discriminate large numbers of HCV types, and further, can be readily adapted in the future when new HCV types and quasispecies are identified. In addition, the HCV typing method can be used simultaneously in conjunction with HCV quantitative analysis to assess viral copy number, where the reagents for the quantitative analysis are incorporated into the same reaction as the HCV typing analysis.

HCV Typing Using Multidimensional Probe Analysis

This present invention provides compositions and methods for HCV typing, where the methods use a plurality of HCV typing probes, and use complementary information from the plurality of probes to make an HCV genotype or subtype assignment. The compositions and methods of the invention can be used to differentiate at least five HCV types (for example, selected from genotypes 1, 2, 3, 4, 5 or 6; or subtypes 1a/b/c, 2a/c, 2b, 3a, 4a, 5a or 6a). The methods of the invention can also be used in cases of mixed HCV infection, with each HCV species present in the sample is assigned to an HCV type (genotype or subtype).

Figure 8:
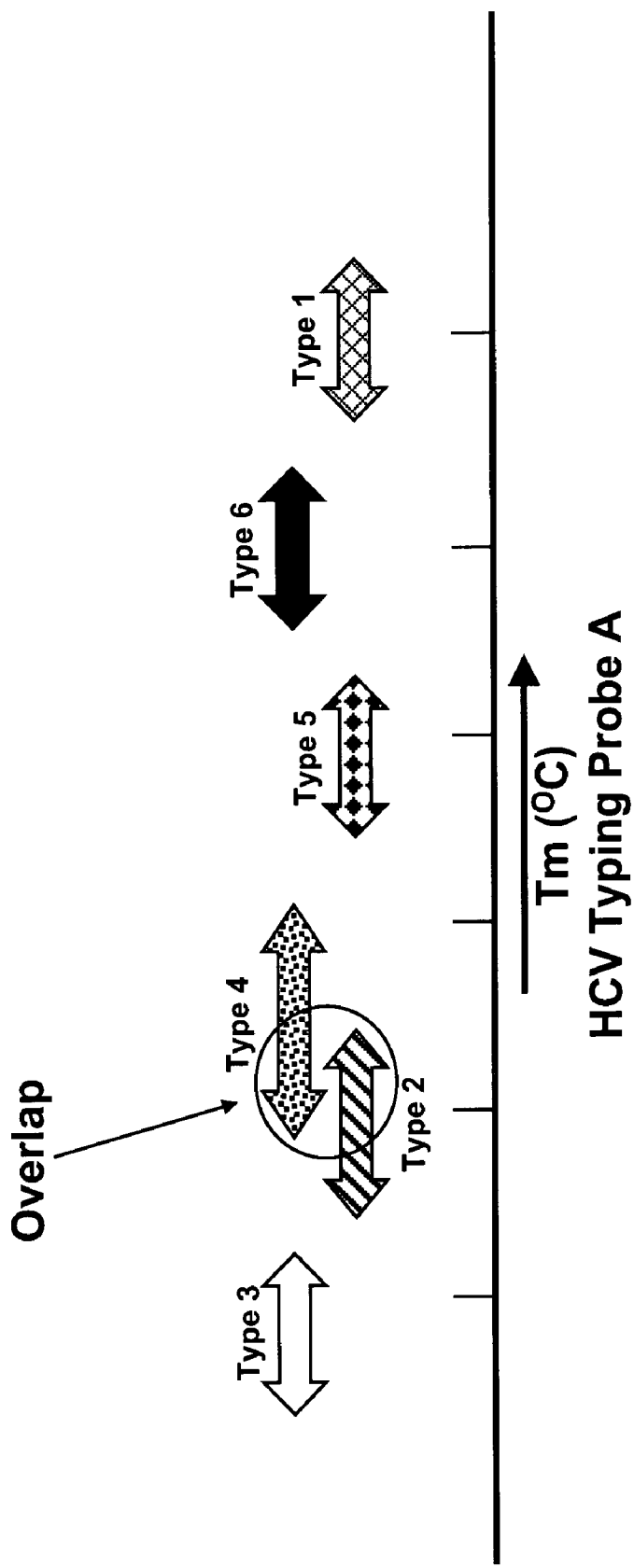
FIG. 8 provides a drawing showing a hypothetical intragenotype $T_m$ variance and type assignment ambiguity using a single hypothetical HCV typing probe, Probe A.
Figure 9:
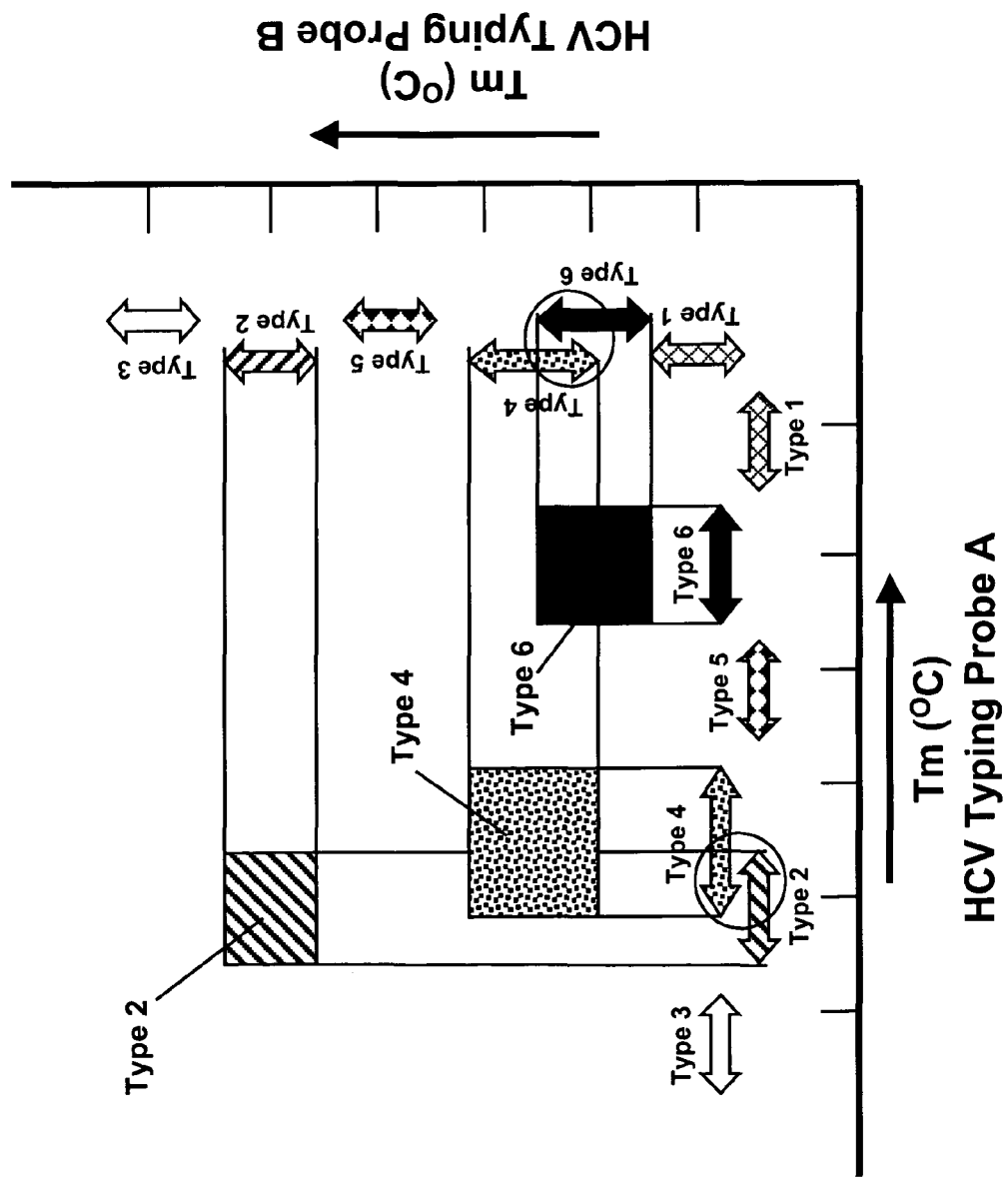
FIG. 9 provides a drawing showing a hypothetical HCV typing assignment using a two dimensional $T_m$ analysis with two hypothetical HCV typing probes, Probe A and Probe B.

As shown in FIG. 8, the assignment of an HCV type can be made difficult by very similar or overlapping $T_m$ values for different HCV types. In fact, $T_m$ characterization for any one HCV type is often a range of $T_m$ values due to genetic variability and/or limitations in instrumentation resolution. The present invention solves this problem, as illustrated in FIG. 9. As shown in FIG. 9, any one probe (e.g., probe A or probe B) give different patterns of $T_m$ values for any collection of HCV types (in this case, hypothetical Types 1 through 6). As can be seen in the figure, relying on either probe A or probe B alone to make a type determination is problematic. Probe A is able to distinguish Types 1, 3, 5 and 6, but is unable to distinguish Type 2 from Type 4. Similarly, probe B is able to distinguish Types 1, 2, 3 and 5, but is unable to distinguish Types 4 and 6. However, if the data from probe A and probe B are considered simultaneously in a two-dimensional dataspace, Type 2 can be resolved from Type 4, and Type 4 can be resolved from Type 6. In the two-dimensional dataspace, the $T_m$ values for Types 2, 4 and 6 each occupy a unique position in the dataspace that does not overlap the dataspace of any other HCV type.

FIG. 9 illustrates a two-dimensional analysis that uses $T_m$ as the quantitative trait to characterize the various hybridization complexes. However, it is not intended that the invention be limited to the use of $T_m$ to characterize the various complexes, as other distinguishing hybridization properties can also be measured and used, as described below.

As shown in FIG. 9, the ability of either hypothetical probe A by itself or probe B by itself to distinguish between a multitude of HCV types is not a requirement, except that probe A and probe B much each by themselves be able to distinguish at least two HCV types. It is not a requirement of the invention that any one probe used in a multidimensional analysis be able to distinguish any more than two HCV types, although in some embodiments, a probe used in the multidimensional analysis (e.g., probe A and/or probe B) will be able to distinguish between three, four, five, six or more HCV types.

Even though a probe that is used in a multidimensional analysis has the ability to distinguish a plurality of HCV types, the use of multidimensional analysis provides advantages over using a single probe to make an HCV type assignment. The multidimensional analysis makes the typing assignment more robust and less susceptible to false typing when dealing with a large number of clinical specimens with intragenotype variance. The compiled layers of information collected during a multidimensional HCV typing analysis also makes a typing assignment less susceptible to small fluctuations in reproducibility due to viral copy number variability. Data stored in a database representing a large number of isolates can be used to compare the multidimensional pattern to make an accurate HCV type assignment. Each genotype/subtype determination is made by a combination of results from multiple probes, providing a unique signature for each HCV genotype/subtype, greatly increasing the confidence level for each determination.

The diagram in FIG. 9 illustrates the situation for two probes and a two-dimensional dataspace. However, it is not intended that the technique be limited to analyses that use only two HCV typing probes. The dataspace can be multidimensional, for example, incorporating the data from three probes in a three dimensional dataspace, or using four probes in a four-dimensional dataspace, etc. Indeed, as the landscape of HCV typing becomes increasingly complex in the scientific literature, the need for multidimensional analysis with an increasing number of typing probes also increases.

In certain embodiments, the closed tube RT-PCR and melting analysis system can be placed in a suitable thermocycler, and the progression of the RT-PCR, hybridization and $T_m$ melting curve analysis is controlled simply by controlling the temperature of the reaction vessel, without the need to move the reaction vessel for different stages of the reactions and analysis. In some embodiments, the thermocycler can be coupled with a suitable fluorescence spectrophotometer in a single instrument.

One advantage of the invention is that the methods described herein can optionally be used in closed-tube systems. Closed-tube systems of the invention do not require the addition of any further reagents following the initiation of the reaction (e.g., initiation of the RT-PCR and melting analysis), and all required reagents are present from the outset of the analysis. For example, when a closed tube system is used, all reagents necessary for the RT-PCR and melting analysis are included in the reaction vessel, including the HCV RNA sample, universal RT-PCR primers, the DNA polymerase (preferably with RT activity) and deoxyribonucleotides.

Furthermore, each HCV typing probe used in the multidimensional analysis can be included in a closed-tube reaction. In the case where the plurality of typing probes are included in the closed-tube reaction, each probe can be tagged with different labels that each have distinct emission spectra, for example FRET labels FAM and HEX, so that fluorescence can be read on two different channels. Although the plurality of typing probes can optionally be used in a closed-tube system that uses multi-channel emission monitoring, it is not a requirement that the probes be used in a closed-tube system. For example, each typing probe, whether using the same or different labels, can be run in separate independent reactions, and the data (e.g., melting analysis data) can be later compiled into the multidimensional dataspace for analysis.

It is frequently advantageous to have HCV genome quantitation data as well as HCV typing information. In another aspect of the invention, the closed-tube system can also optionally incorporate reagents for HCV quantitation, e.g., a TaqMan-type probe to monitor the accumulation of HCV amplicon during the RT-PCR amplification step.

Generally, in one aspect, the multidimensional HCV typing methods of the invention comprise the steps outlined below:

(A) Optionally, Amplifying a Portion of the HCV Genome from a Sample.

In some embodiments, a sample comprising a hepatitis C virus of unknown type is used directly in the typing analysis (without the need for an amplification step). In this case, HCV genomic material, or alternatively HCV transcripts, can optionally be isolated from the sample, for example, using any suitable nucleic acid isolation technique. That isolated material can be used in the subsequent analysis. Techniques for the analysis of nucleic acids with very low copy number are known in the art (e.g., fluorescence detection) and find use with the invention. See, for example, Mirkin et al., "PCR-Less detection of genomic DNA with nanoparticle probes," Abstracts of Papers, 222nd ACS National Meeting, Chicago, Ill., United States (Aug. 26-30, 2001).

In some embodiments, an HCV amplification step is optionally employed prior to the typing analysis. This amplification is typically by an asymmetric RT-PCR reaction, where the region amplified encompasses a domain of sufficient variability between at least two HCV types (genotypes or subtypes) such that there exists unique nucleotide sequences corresponding to the two HCV types relative to other HCV types. The region that is amplified is not particularly limited, and can be from any suitable part of the viral genome. The amplified region can reside in a highly conserved region (e.g., the 5'-UTR region) or a hypervariable region (e.g., the NS5B region that encodes the HCV polymerase) Alternatively, the core or E1 regions can also be used. In some embodiments, the PCR primers used to generate the HCV amplicon are "universal primers," where the primers will generate an amplicon regardless of the HCV genotype or subtype. Universal type HCV primers (and HCV-specific PCR kits) suitable for generating universal HCV amplicons are widely known, and are also commercially available (see, e.g., Roche COBAS AMPLICOR™ HCV MONITOR test kit (Roche Molecular Systems, Inc, Pleasanton, Calif.). In other embodiments, two or more sets of primers can be used.

The DNA polymerase used in the PCR reactions is not particularly limited. As the PCR amplicon is generated from HCV RNA genomic material, the PCR reaction can be a one step reverse transcription (RT) PCR reaction using a thermostable polymerase that also has RT activity (e.g., *Thermus* sp. strain ZO5, Roche Molecular Systems). Alternatively, the RT-PCR can be a stepwise reaction using two different enzymes, one for the reverse transcription step to generate a cDNA, and the other for the amplification step. In certain embodiments, one of the PCR amplification primers also serves to prime the RT activity to create an HCV cDNA first strand. PCR and RT-PCR reagents and methods are routine widely known in the art.

The RT-PCR reaction can optionally contain dUTP in place of dTTP, and in a higher molar concentration than the other deoxyribonucleotides. This can be used for the generation of dUTP-containing amplicons, useful for preventing cross contamination of PCRs with exogenous DNA. In systems utilizing dUTP-containing amplicons, a uracil N-glycosylase (UNG) nuclease digest followed by UNG inactivation prior to HCV reverse transcription and amplification can eliminate cross-contamination from other dUTP-containing polynucleotides. Such systems are commonly used in the art, and are available from various sources (see, e.g., Roche Diagnostics AmpErase®).

In one aspect, the sample is a blood or blood product (e.g. plasma) sample from a patient, where the patient is proven to have an HCV infection, or is suspected of having an HCV infection. Typically, but not a requirement, a sample is at least partially purified for the purpose of enriching the RNA component of the sample, which will contain the HCV genomic material. Any suitable RNA purification method can be used, and can be either total RNA purification or polyA RNA purification. Preferably, the method used to enrich the RNA is a rapid method that can be applied in a manner suitable for use in high-throughput methodologies or robotic systems. For example, the QIAamp® Viral RNA Mini Kit (QIAGEN N.V. Venlo, the Netherlands) and the High Pure RNA Isolation Kit (Roche Applied Sciences, Indianapolis, Ind.).

(B) Hybridizing the HCV Material with a Plurality of HCV Typing Probes to Form Target Hybridization Complexes.

The HCV material (e.g., sample material or an HCV amplicon generated from an RT-PCR amplification) is then used in a hybridization reaction with a plurality of HCV typing probes to form hybridization complexes. The HCV typing probes are designed with various considerations, including (i) the probe sequences are at least partially complementary to nucleotide sequence within the HCV amplicon, where there is sufficient complementarity to allow hybridization under at least non-stringent conditions; (ii) the region(s) of hybridization complex complementarity show sequence heterogeneity among at least two HCV types (genotypes or subtypes); (iii) hybridization complexes comprising each typing probe and the at least two HCV types have a distinguishing hybridization property that differentiates each from the remaining types. The nucleotide sequences of the plurality of typing probes that are used are not identical; however, the plurality of probes can have overlapping nucleotide sequences or modifications of the same nucleotide sequence that hybridize to the same region of the HCV genome. The hybridization reactions with the plurality of typing probes can occur in a single reaction mix, or in separate, independent reaction mixes.

As used in the invention, it is not intended that the term hybridization be limited to soluble-phase hybridizations. One of skill in the art recognizes that a variety of alternative hybridization methodologies find use with the invention. For example, solid phase hybridization techniques may be performed on a variety of surfaces, including membranes, filter papers, beads, gels, and the like. The hybridization probes may be covalently or non-covalently attached to the surface of the solid phase. Alternatively, a capture oligonucleotide may hybridize to a portion of the hybridization probe not involved in formation of the HCV hybridization complex, or a capture antibody specific for such a portion of the hybridization probe may be attached to the solid phase.

When the probes form hybridization complexes with a particular HCV genotype or subtype, the resulting hybridization complexes have a unique property or properties that are characteristic of that particular genotype or subtype, and are different from the property/properties of hybridization complexes it can form with other genotypes or subtypes.

In some embodiments, the distinguishing hybridization property is a melting temperature ($T_m$). Methods for the in silico prediction and experimental determination of $T_m$'s are well known to one of skill in the art. However, it is not intended that the invention be limited to the use of $T_m$ as the only distinguishing hybridization property. Other techniques can also be used for distinguishing differences between hybridization complexes. For example, the distinguishing hybridization property can be $T_{25}$ or $T_{75}$. In other embodiments, different hybridization complexes comprising an HCV typing probe can be differentiated from each other by using heteroduplex mobility analysis (HMA), denaturing HPLC (DHPLC), cleavase fragment length polymorphism (CFLP) or thermal gradient capillary electrophoresis (TGCE). In addition, different distinguishing hybridization properties can be combined to enhance resolution of the hybridization complex.

Examples of HCV typing probes that can be used with the invention are provided in FIG. 6. The choice of which combinations of probes to use in a multidimensional typing analysis is dictated by which combinations of probes provide complementary information to the multidimensional dataspace (see, FIG. 9). For example, if one probe is able to distinguish HCV types 1, 2, 3 and 4, but not types 5 or 6, a suitable complementary probe will be any probe that can distinguish types 5 and/or 6 from types 1, 2, 3 and 4. Examples of effective probe pair combinations for multidimensional analysis include probes AG0307M (SEQ ID NO: 26) and AG0308K (SEQ ID NO: 54); probes AG0203A-FAM (SEQ ID NO: 10) and AG0308J (SEQ ID NO: 53); and probes AG0308AA (SEQ ID NO: 57) and AG0308H (SEQ ID NO: 52).

In a similar manner, combinations of three or more typing probes can similarly be used in a multidimensional analysis. For example, one probe that can distinguish only HCV types 1, 2 and 3, another probe that distinguishes only types 3 and 4, and another probe that can distinguish only types 5 and 6 make an effective combination in a three-probe multidimensional analysis.

In some aspects, other considerations for the choice of probes used in a multidimensional HCV typing analysis influence the user's selection of probes. These considerations are not necessary mutually exclusive of the other approaches to probe selection described herein; indeed; in some aspects, multiple factors are simultaneously considered. For example, a combination of probes can be selected where each probe provides a data point that is distinct from the data point provided by each of the other probes in the combination for at least one HCV viral type. In this approach, the focus is on the simultaneous interrogation of the HCV sequence with multiple probes of varying affinity. The final composite result can be described as a sequence sensing strategy in which a data pattern (for example, based on melting temperatures) defines an HCV type (e.g., an HCV genotype), which can be distinguished readily from other HCV types, each having it's own distinct signature, made possible by the choice of probes in the combination. As discussed above, a benefit to this approach is that any one probe used in the combination of probes does not need to resolve all the HCV types in question (e.g., five or more HCV genotypes).

It is not intended that the HCV typing probes that find use with the invention be limited to those probes listed in FIG. 6. Upon reading the description of the invention, it will be apparent to one of skill in the art how to derive additional probes that also find use with the invention. Also, as noted in FIG. 6 and EXAMPLE 6, probe sequences are provided that indicate various fluorescent labels as part of the sequences. For example, character "F" in FIG. 6 indicates the label "FAM" and the symbol "H" indicates HEX. However, it is not intended that the base sequences of these probes be limited to the particular labels FAM or HEX. One of skill recognizes that any of a variety of labels known in the art finds use with the base sequences of these probes.

As described herein, the hybridization reactions of the invention incorporate at least two HCV typing probes for the multidimensional HCV typing analysis. In some embodiments, each of these typing probes (or a subset of the typing probes) are optionally contained in a single hybridization reaction, and further where each of the typing probes has a polynucleotide sequence that targets the probe to the same target region in the HCV genome (e.g., in the HCV amplicon generated by an RT-PCR reaction). Fortuitously, it was observed that the presence of a plurality of probes designed to probe the same target region, but with different thermodynamic stabilities in a single hybridization reaction did not result in any competition or any type of binding interference with each other. In other words, each probe in the reaction yielded a binding profile and melting curve that was unaffected by the presence of the other HCV typing probes in the reaction, even though the probes had the same target specificity. Each probe in the multiprobe reaction behaved as if it were the only probe in the reaction. For example, this was observed when the AG0203A-FAM and the AF0308J(HEX) probes were alternatively used in a multidimensional HCV typing analysis, where the probes were first used independently in separate melting curve hybridization reactions, and then used in combination in the same hybridization reaction.

(C) Measuring the Hybridization Property of the Hybridization Complexes.

Once the hybridization complexes between the HCV material and the HCV typing probes are formed, the distinguishing hybridization property is measured. In one aspect, as discussed above, the hybridization property is a $T_m$, and a $T_m$ melting curve analysis is conducted. However, it is not intended that the invention be limited to the use of $T_m$ as a distinguishing property. Indeed, the use (i.e., measurement) of other properties, either alone or in combination, can be advantageous, especially for high throughput applications.

In some embodiments (when, e.g., $T_m$ is used as a distinguishing property), the RT-PCR reaction, the probe/target hybridization reaction and the measurement of the $T_m$ is done in a single "closed tube" system without the need for addition of any further reagents after the initiation of the RT-PCR reaction. In the closed tube system, all reagents necessary for each step are present in the tube from the outset of the analysis. For example, in some embodiments, the closed tube RT-PCR and $T_m$ system will contain the HCV RNA sample, universal RT-PCR primers, the DNA polymerase (preferably with RT activity), deoxyribonucleotides, suitable HCV typing probes (optionally where the probes are labeled with one or more suitable FRET components) and optionally a soluble FRET quencher. In certain embodiments, the closed tube RT-PCR and $T_m$ system can be placed in a suitable thermocycler, and the progression of the RT-PCR, hybridization and $T_m$ melting curve analysis is controlled simply by controlling the temperature of the reaction vessel, without the need to move the reaction vessel for different stages of the reactions and analysis. Similarly, in some embodiments, the thermocycler is coupled with a suitable fluorescence spectrophotometer so that a melting curve fluorescence monitoring can be done without moving the reaction vessel.

It is not intended that the invention be limited to any particular method for the determination of $T_m$. Diverse methods for the experimental determination of $T_m$ are widely known in the art and are described in a variety of sources, e.g., Liew et al., "Genotyping of Single-Nucleotide Polymorphism by High-Resolution Melting of Small Amplicons," Clinical Chemistry 50(7): 1156-1164 (2004); Reed and Wittwer "Sensitivity and Specificity of Single-Nucleotide Polymorphism Scanning by High-Resolution Melting Analysis," Clinical Chemistry 50(10):1748-1754 (2004); Zhou et al., "Closed-Tube Genotyping with Unlabeled Oligonucleotide Probes and a Saturating DNA Dye," Clinical Chemistry 50(8):1328-1335 (2004); and Zhou et al., "High-resolution DNA melting curve analysis to establish HLA genotypic identity," Tissue Antigens 64:156-164 (2004). Melting curve analysis instrumentation is commercially available from a variety of manufacturers. It is recognized that different melting curve instrumentation can have different sensitivities. For example, one instrument may be able to resolve $T_m$ to ±0.5° C., whereas a different apparatus may be able to resolve $T_m$ to ±0.1° C. Thus, one HCV typing probe that is able to theoretically yield $T_m$ values of each HCV type with a separation of 0.2° C. can be used effectively on one make and model of $T_m$ instrumentation, but not on another HCV instrumentation that does not have the required sensitivity.

(D) Correlating the Measured Hybridization Property (e.g. $T_m$) with an HCV Type.

Once the hybridization property has been measured using the plurality of probes as described in (C), that information is used to assign an HCV type to the HCV in the sample, based on the values of the hybridization property that were measured. For example, when $T_m$ is the measured distinguishing property, tables of standardized $T_m$ values using known HCV type isolates is assembled for two or more typing probes prior to analysis of the experimental sample. The standardized $T_m$ tables will consist of $T_m$ values predetermined for each typing probe and for each HCV genotype or subtype under the same hybridization conditions used in the analysis of the experimental sample. Once the $T_m$ values for the experimental sample are measured, those values are compared to the standardized tables of $T_m$ values, and an analysis analogous to that described in FIG. 9 is completed. Identical or near identical values for the standardized and experimental samples indicates a correspondence between the known type and the experimental type.

Alternatively, standardized samples of each HCV genotype or subtype can be analyzed in parallel with the experimental sample, and an HCV type assignment can be made based on comparing the experimental values with the standard values (e.g., the $T_m$ values) measured at the time of the assay.

In some embodiments, the methods for HCV typing are coupled to methods for determining HCV viral load. The combination of qualitative (typing) and quantitative (viral concentration) HCV analyses in the same assay is a great benefit to the clinician who is treating a patient. Methods for HCV quantitation are well known in the art, e.g., COBAS AMPLICOR™ HCV MONITOR Kit (Roche Molecular Systems, Inc., Pleasanton, Calif.). These commercial systems typically use a TaqMan-type probe in a PCR reaction to monitor the real-time accumulation of a universal HCV amplicon in an RT-PCR reaction.

The rate of PCR amplicon accumulation, as monitored by TaqMan probe fluorescence, is directly proportional to the amount of RNA genome starting material in a sample. By inclusion of appropriate HCV concentration standards in a TaqMan PCR reaction, it can be determined how many HCV genome molecules were present in the starting reaction. With that knowledge, the concentration of HCV genome particles in the experimental sample can be extrapolated.

In some embodiments of the invention, a TaqMan-type probe is included in the RT-PCR reaction mix, and the real-time accumulation of PCR amplicon is monitored. From that information, the concentration of HCV genome in the sample is calculated. In certain embodiments, the HCV quantitation is coupled with the HCV genotyping in a closed-tube system, where the TaqMan-type probe is included in the reaction mix that contains all the reagents for RT-PCR amplification and hybridization characterization (e.g., $T_m$ melting curve analysis). When the quantitative HCV analysis is coupled with the HCV typing, an asymmetric PCR reaction is typically used in the RT-PCR amplification reaction. In that case, the TaqMan-type detection probe is designed to be complementary to the limiting amplicon strand, and the HCV typing probes are designed to be complementary to the abundant excess amplicon strand. Furthermore, the TaqMan quantitation probe is designed to hybridize to a conserved region of the HCV amplicon so that the probe will hybridize to the genome of any HCV type. In certain embodiments, the quantitation probe will hybridize to all HCV type amplicon sequences with equal affinity. Viral load calculations can be made using fluorescence derivative plots (e.g., first derivative and second derivative plots).

Design of HCV Typing Probes of the Invention

Generally, HCV typing probes of the invention are designed using the following guidelines:

1) Identify Sequences in the HCV Genome Showing Heterogeneity Among at Least Two HCV Types (Genotypes or Subtypes).

The sequences in the HCV genome targeted for hybridization are not particularly limited. The probe can hybridize to relatively conserved domains that have sufficient heterogeneity (e.g., the 5'-UTR) or reside within more variable domains in the HCV genome. When a suitable probe target is identified, the use of proper universal amplification primers is also considered, where the HCV amplicon that will be generated must contain the typing probe target sequence, but also, sequences that flank the probe target sequence must be sufficiently conserved to allow the use of universal PCR primers that will generate an HCV amplicon regardless of the HCV type. A candidate HCV typing probe is designed that will hybridize to the region of heterogeneity.

Various commercial programs are widely available for the design of hybridization probes. Examples of such commercially available programs include Visual OMP (DNA Software, Inc., Ann Arbor, Mich.), and the $T_m$ utility tool from Idaho Technology, Inc. (Salt Lake City, Utah). It is not intended that the invention be limited to the use of any particular software for designing probe sequences.

It is not a requirement that an HCV typing probe of the invention have a nucleotide sequence that is identical (100% complementary) to any one HCV type. An HCV typing probe of the invention can have a nucleotide sequence that is intentionally less than 100% complementary to each HCV genome type. That case may be desirable for the purpose of giving that probe desired hybridization properties that will allow the probe to distinguish between a plurality of HCV types. For example, mismatches can be intentionally designed into a probe for the purpose of changing the $T_m$ of the resulting hybridization complex. Examples of HCV typing probes are provided in FIG. 6.

2) Test Candidate Typing Probe Sequences In Silico.

Once a candidate probe sequence is identified, that sequence is optionally tested in silico for its ability to display a differentiating property when hybridized to each of the known HCV type sequences. For example, when a candidate probe sequence is identified, in silico modeling can be used to predict the $T_m$ of the hypothetical hybridization complexes with that probe and the complementary target in each of the known HCV types. An effective probe candidate must display a sufficiently distinguishing property (e.g., $T_m$) with each of the HCV types to be effective.

Various commercial programs are widely available for the prediction of $T_m$ of a particular hybridization complex. For example, Visual OMP (DNA Software, Inc., Ann Arbor, Mich.), and the $T_m$ utility tool from Idaho Technology, Inc. (Salt Lake City, Utah). It is not intended that the invention be limited to the use of any particular software for predicting $T_m$.

The optional in silico testing of the candidate HCV typing probes is for initial guidance in identifying effective versus ineffective probes. The in silico screening is not strictly required before proceeding to the step of experimental testing and measuring the hybridization properties of the HCV typing probes. Furthermore, it is understood that in silico prediction of $T_m$ values is only an approximation, and experimental observation and confirmation is required.

3) Test Candidate Probes In Vitro.

As a final step in probe design, the typing probe is tested in vitro for its ability to distinguish each HCV type using at least one testing method. This testing step is necessary to confirm the results of the in silico prediction, which does not have 100% accuracy in predicting probe behavior. Two testing methods are suggested herein, however, other equivalent testing techniques can be employed.

A. Chemically Synthesized HCV Targets

In some embodiments where $T_m$ values are determined, the probe is used in melting curve analyses with artificial synthetic HCV targets (chemically synthesized) that have nucleotide sequences corresponding to each HCV type (as provided in FIG. 5). The $T_m$ for each hybridization complex comprising the typing probe and each HCV synthetic template is determined experimentally. The RT-PCR reaction to generate an HCV amplicon is not required in these assays. A successful probe is a probe that yields a different and distinguishable $T_m$ value for at least two HCV types (genotypes or subtypes).

B. Enzymatically Synthesized HCV Transcripts

Alternatively, or in addition to chemically synthesized targets, $T_m$ melting curve verification can be done using synthetic HCV transcripts (enzymatically synthesized, e.g., by in vitro transcription). Transcripts generated by in vitro transcription from plasmids carrying HCV inserts of known genotype and subtype can be used in this verification testing (see, EXAMPLE 2).

Probe and Primer Synthesis

The invention also provides a number of probes and primers, for example, HCV typing probes, HCV quantitation (TaqMan®-type) probes and HCV amplification primers (for use in RT-PCR). It is not intended that the methods used to produce these probes and primers be in any way limited. One of skill in the art is well familiar with the wide variety of chemical synthesis strategies and reagents for producing probes and primers.

Also, it is not intended that the HCV typing probes and primers of the invention be limited to naturally occurring nucleotide structures or naturally occurring bases (e.g., adenine, guanine, thymine, cytosine, and uracil). In addition to the naturally occurring heterocyclic bases that are typically found in nucleic acids, non-natural nucleic acid analogs also find use with the invention. Non-natural analogs include those having non-naturally occurring heterocyclic or other modified bases. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d] pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 7-deazaadenine, 2-methyladenine, 2-methylguanine, 3-methylcytosine, 5-methylcytosine, N6-methyladenine, 7-methylguanine, 7-deazaguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine, and the like. To further illustrate, other examples of modified oligonucleotides include those having one or more locked nucleid acid (LNA™) monomers (oligonucleotides comprising LNA™ monomers available from, e.g., Link Technologies, Ltd., Lanarkshire, Scotland; under license from Exiqon A/S, Vedbæk, Denmark). Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

Oligonucleotide probes and primers can be prepared using any technique known in the art. In certain embodiments, for example, the oligonucleotide probes and primers are synthesized chemically using any nucleic acid synthesis method, including, e.g., according to the solid phase phosphoramidite method described by Beaucage and Caruthers (1981) *Tetrahedron Letts.* 22(20):1859-1862, which is incorporated by reference. To further illustrate, oligonucleotides can also be synthesized using a triester method (see, e.g., Capaldi et al. (2000) "Highly efficient solid phase synthesis of oligonucleotide analogs containing phosphorodithioate linkages" *Nucleic Acids Res.* 28(9):e40 and Eldrup et al. (1994) "Preparation of oligodeoxyribonucleoside phosphorodithioates by a triester method" *Nucleic Acids Res.* 22(10):1797-1804, which are both incorporated by reference). Other synthesis techniques known in the art can also be utilized, including, e.g., using an automated synthesizer, as described in Needham-VanDevanter et al. (1984) *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED NUCLEIC ACID AMPLIFICATION PRIMERS," issued Dec. 14, 1999 to Will, which is incorporated by reference. Primers and probes can also be synthesized with various other modifications as described herein or as otherwise known in the art.

Probes utilized in the reaction mixtures, methods, and other aspects of the invention are typically labeled to permit detection of probe-target hybridization duplexes. Labels can be attached to oligonucleotides directly or indirectly by a variety of techniques known in the art. To illustrate, depending on the type of label used, the label can be attached to a terminal (5' or 3' end of an oligonucleotide primer and/or probe) or a non-terminal nucleotide, and can be attached indirectly through linkers or spacer arms of various sizes and compositions. Using commercially available phosphoramidite reagents, one can produce oligonucleotides containing functional groups (e.g., thiols or primary amines) at either the 5' or 3' terminus via an appropriately protected phosphoramidite, and can label such oligonucleotides using protocols described in, e.g., Innis et al. (Eds.) *PCR Protocols: A Guide to Methods and Applications*, Elsevier Science & Technology Books (1990) (Innis), which is incorporated by reference.

Essentially any nucleic acid (standard or non-standard, labeled or non-labeled) can be custom or standard ordered from any of a variety of commercial sources, such as The Midland Certified Reagent Company (Midland, Tex.), Operon Technologies Inc. (Huntsville, Ala.), Proligo LLC (Boulder, Colo.), and many others.

Labels

The invention also provides a number of probes to be used in conjunction with the invention, for example, HCV typing probes and HCV quantitation (TaqMan-type) probes. As probes, these molecules typically comprise a suitable label. It is not intended that the label, label detection system or instrumentation for label detection and quantitation be limited in any way. One of skill in the art is well familiar with the wide variety of labeling strategies and reagents for producing suitably labeled polynucleotides.

Labels can, alternatively or in combination: (i) provide a detectable signal; (ii) interact with a second label to modify the detectable signal provided by the second label, e.g., FRET; (iii) stabilize hybridization, i.e., duplex formation; (iv) confer a capture function, i.e., hydrophobic affinity, antibody/antigen, ionic complexation, or (v) change a physical property, such as electrophoretic mobility, hydrophobicity, hydrophilicity, solubility, or chromatographic behavior. Labeling can be accomplished using any one of a large number of known techniques employing known labels, linkages, linking groups, reagents, reaction conditions, and analysis and purification methods. Labels include light-emitting or light-absorbing compounds which generate or quench a detectable fluorescent, chemiluminescent, or bioluminescent signal (Kricka, L. in Nonisotopic DNA Probe Techniques (1992), Academic Press, San Diego, pp. 3-28).

Essentially any labeling moiety is optionally utilized to label a probe and/or primer by techniques well known in the art. In some embodiments, for example, labels comprise a fluorescent dye (e.g., a rhodamine dye, e.g., R6G, R110, TAMRA, ROX, etc., see U.S. Pat. Nos. 5,366,860; 5,847,162; 5,936,087; 6,051,719; 6,191,278), a fluorescein dye (e.g., JOE, VIC, TET, HEX, FAM, etc.; 6-carboxyfluorescein; 2',4', 1,4, -tetrachlorofluorescein; and 2',4',5',7',1,4-hexachlorofluorescein; see U.S. Pat. Nos. 5,188,934; 6,008,379; 6,020, 481), benzophenoxazines (U.S. Pat. No. 6,140,500), a halofluorescein dye, a cyanine dye (e.g., CY3, CY3.5, CY5, CY5.5, CY7, etc., see Published International Application No. WO 97/45539 by Kubista), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc.

FRET labeling techniques are commonly used in both real-time amplicon quantitation and for monitoring nucleic acid probe hybridization. In some preferred embodiments, FRET label systems are used with the probes of the invention. It is not intended that the invention be limited to any particular FRET pair system. One of skill in the art recognizes the wide range of FRET labels that can be used with the probes of the invention. Fluorescent energy-transfer dye pairs of donors and acceptors include, e.g., U.S. Pat. Nos. 5,863,727; 5,800, 996; 5,945,526, as well as any other fluorescent label capable of generating a detectable signal.

Whether a fluorescent dye is a label or a quencher is generally defined by its excitation and emission spectra, and the fluorescent dye with which it is paired. Fluorescent molecules commonly used as quencher moieties in probes and primers include, e.g., fluorescein, FAM, JOE, rhodamine, R6G, TAMRA, ROX, DABCYL, and EDANS. Many of these compounds are available from the commercial suppliers referred to above. Examples of non-fluorescent or dark quenchers that dissipate energy absorbed from a fluorescent dye include the Black Hole Quenchers™ or BHQ™, which are commercially available from Biosearch Technologies, Inc. (Novato, Calif., USA). Other quenchers include Iowa Black quenchers (e.g., Iowa Black FQ™ and Iowa Black RQ™) and Eclipse® Dark Quenchers (Epoch Biosciences, Inc, Bothell, Wash.).

The EXAMPLES provided herein describe HCV typing probes that are labeled with FRET donor moieties, and are used in conjunction with a soluble quencher. However, it is not intended that the invention be limited to those types of probe configurations. For example, an HCV typing probe of the invention can be a molecular beacon type of probe, where the probe comprises both the donor and the quencher moieties, as known in the art. Alternatively, an HCV typing probe of the invention can be a TaqMan type probe, also where the probe comprises both donor and quencher moieties (but does not necessarily have an intervening stem structure and does not get cleaved by a polymerase with exonuclease activity).

Alternatively, the donor-labeled HCV typing probes of the invention can be used in conjunction with a quencher-labeled anchor probe in place of a soluble quencher. In this scenario, an anchor probe is designed to hybridize to a conserved HCV region immediately adjacent to the HCV typing probe, and where the anchor probe is labeled with a suitable quencher moiety. When both probes are hybridized to their respective targets, FRET donor quenching occurs. During conditions during the melting curve analysis, the HCV typing probe will eventually dissociate from its target sequence, leaving only the anchor probe bound to the HCV amplicon, resulting in an increase in donor fluorescence. Anchor probe FRET systems are known in the art, and are described, for example, in Schroter et al., (2002) Jour. Clin. Microbiol., 40(6):2046-2050.

Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, calorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6): 1725), and an alpha-methyl-PEG labeling reagent as described in, e.g., U.S. patent application Ser. No. 10/719,257, filed on Nov. 21, 2003, which references are each incorporated by reference.

Another class of labels are hybridization-stabilizing moieties which serve to enhance, stabilize, or influence hybridization of duplexes, e.g., intercalators, minor-groove binders, and cross-linking functional groups (Blackburn, G. and Gait, M. Eds. "DNA and RNA structure" in Nucleic Acids in Chemistry and Biology, 2.sup.nd Edition, (1996) Oxford University Press, pp. 15-81).

Yet another class of labels effect the separation or immobilization of a molecule by specific or non-specific capture, for example biotin, digoxigenin, and other haptens (Andrus, "Chemical methods for 5' non-isotopic labelling of PCR probes and primers" (1995) in PCR 2: A Practical Approach, Oxford University Press, Oxford, pp. 39-54).

Non-radioactive labelling methods, techniques, and reagents are reviewed in: Non-Radioactive Labelling, A Practical Introduction, Garman, A. J. (1997) Academic Press, San Diego.

In some embodiments, the two types of probes that are used in the invention, namely the HCV typing probe and the HCV quantitation probe, use the same label, for example, a fluorescein label. This provides various advantages, as the HCV quantitation assay and the HCV typing assay can be read in the same detector, e.g., a fluorescence spectrophotometer. However, it is not intended that the invention be limited to that type of configuration. For example, the two different probes can use two different fluorescent labels that have non-identical emission spectra (or even different labelling systems, such as fluorescent and non-fluorescent label systems).

Use of Soluble Quencher Technology

In some embodiments, FRET label systems are used with the probes of the invention, e.g., TaqMan-type probes and HCV quantitation probes. However, it is not intended that the invention be limited to the use of FRET donor/quencher systems. Indeed, FRET systems are merely a subset of possible energy transfer systems that find use with the invention (e.g., non-fluorescent energy transfer systems are known in the art), nor is the invention limited to any particular FRET pair system. In some embodiments, a FRET system that uses a soluble quencher is utilized.

As used herein, the expressions "soluble acceptor" or "soluble quencher" or the like refer to an acceptor moiety that is not attached to any other molecule, and is largely soluble or otherwise not bound to any other molecule or solid phase. In some embodiments, a soluble quencher can be part of a FRET pair, where the soluble quencher is a FRET quencher and can interact with a FRET donor in a functional FRET pair. For example, ethidium bromide and some thiazine dyes e.g., methylene blue, Azure A, Azure B, Azure C, thionin, and new methylene blue, can be used as soluble quenchers.

A thiazine dye soluble quencher acts by binding to double-stranded nucleic acid, but has reduced affinity for single-stranded nucleic acid. Without being bound to any particular theory, it is believed that the predominant binding mode is through intercalation, but minor and major groove binding is also possible depending on the sequence context and hybridization conditions (see, Rohs et al. (2000) J. Am. Chem. Soc., 122:2860-2866; and Tuite et al. (1994) J. Am. Chem. Soc., 116:7548-7556). Thus, the fluorescence donor label attached to a probe that forms a hybridization complex with a target polynucleotide is subject to a quenching effect by the intercalating soluble quencher that has an affinity for double-stranded nucleic acid due to the close proximity of the quencher to the donor moiety on the probe. If the solution containing the hybridization complex is heated (as in a melting curve analysis and $T_m$ determination), the probe eventually dissociates from the target polynucleotide, thereby reducing the affinity of the quencher for the nucleic acid, resulting in reduced proximity of the soluble quencher to the probe donor and an increase in fluorescence from the donor. Thus, the formation/dissociation of hybridization complexes in a reaction can be monitored by the use of a FRET system having a soluble FRET quencher.

The concentration of the soluble quencher used in a particular HCV typing reaction is not limited, and ranges of effective concentrations will be apparent to one of skill in the art. For example, when using thiazine dye soluble quenchers, in some embodiments, a range defined by and including of 5 µg/mL and 100 µg/mL is contemplated. In some embodiments, a preferred range is 10-50 µg/mL, or alternatively, 10-25 µg/mL. Alternatively still, a concentration of 25 µg/mL of the thiazine dye soluble quencher is used.

Further detailed description of soluble light emission modifiers (e.g., soluble FRET quenchers) and the uses thereof is found in cofiled U.S. patent application Ser. No. 11/474,062, filed on Jun. 23, 2006, entitled "LIGHT EMISSION MODIFIERS AND THEIR USES IN NUCLEIC ACID DETECTION, AMPLIFICATION AND ANALYSIS," by Gupta and Will, the entire content of which is hereby incorporated by reference in its entirety for all purposes.

Closed System VS. Open System Typing Assays

The invention provides methods for HCV typing, and also provides methods for concurrent HCV typing and HCV quantitation. In certain embodiments, the reactions for HCV typing and HCV typing/quantitation are "closed-tube" systems (see, EXAMPLE 2).

In the closed tube system, all reagents necessary for each step are present in the tube from the outset of the analysis. In contrast, an "open-tube" system requires the addition of a reagent(s) or additional component(s) after the start of the HCV typing analysis. Closed-tube systems have certain advantages over open-tube systems, since closed-tube systems reduce need for operator intervention and allow for highly parallel rapid throughput. Closed tube systems are also far preferable for commercial applications such as "kits," since the instructions provided to a kit user are simpler, contain fewer steps and the method has fewer possible opportunities where user-errors or contamination can be introduced. In some circumstances, open-tube systems can be advantageous, e.g., to enable use of incompatible reagents.

For example, in some embodiments of the invention, the HCV typing and HCV quantitation concurrent analysis is run as a closed-tube system. In such a system, the reaction tube (or reaction well or chamber) will comprise from the outset, for example, the RNA sample, universal RT-PCR primers to generate the HCV amplicon, a DNA polymerase having RT activity, deoxyribonucleotides, a TaqMan®-type probe for HCV amplicon quantitation, suitable HCV typing probes (optionally where the probes are labeled with suitable FRET donors), and a soluble FRET quencher. With these reagents in the tube, the reaction has all the components necessary for HCV amplicon production, real-time monitoring of HCV amplicon accumulation and the HCV melting curve $T_m$ analysis for the HCV type identification.

Kits and Articles of Manufacture

The present invention provides articles of manufacture, for example, kits, and in particular, diagnostic kits and kits for HCV genotyping. These kits provide the materials necessary for typing HCV infections, using the methods described herein. These kits find use for the clinician, who can use the HCV typing information in the clinic to predict responsiveness of a particular HCV infection to various treatments based on the virus type (e.g., the genotype or the subtype). The invention provides kits to facilitate the methods of the present invention, e.g., methods for typing the HCV in a sample. Materials and reagents to carry out these methods can be provided in kits to facilitate execution of the methods.

In some embodiments, the kits are diagnostic kits, where the information obtained from performing the methods enabled by the kits is used to identify the type of HCV infection in a sample taken from a patient.

In certain embodiments, the invention provides kits suitable for "closed-tube" HCV genotyping employing RT-PCR, as described herein. In other embodiments, the invention provides kits suitable for closed-tube HCV typing employing RT-PCR with HCV quantitation.

The kits of the invention can provide any or all of the synthetic oligonucleotides used in methods described herein. For example, the kits can provide oligonucleotide primer(s) suitable for priming reverse transcription from an HCV RNA molecule to produce an HCV cDNA. The kits can provide amplification primers suitable for amplification of any suitable portion of the HCV genome, e.g., sequences in the 5'-UTR domain. The invention provides suitable HCV amplification primers that can be included in kits of the invention. It is understood that the invention is not limited to the primers recited herein, as any other suitable amplification primers also find use with the invention.

The kits of the invention can include oligonucleotide probes suitable for the HCV typing melting curve analysis. The invention provides a number of suitable probes, e.g., the probes provided in FIG. 6. It is understood, however, that the kits of the invention are not limited to the probes provided in FIG. 6, as the invention also provides guidance for the identification and synthesis of additional probes. The probes provided in kits of the invention can be labeled or unlabeled. Optionally, HCV typing probes provided with the kits of the invention can be labeled with suitable FRET donor moieties, as known in the art. Optionally, an HCV typing probe provided with the kits of the invention can be a TaqMan-type probe, comprising both a donor and a quencher moiety (in this case, a soluble quencher will not be necessary). Optionally, kits of the invention can include a suitable soluble quencher, e.g., a thiazine dye such as new methylene blue. Optionally, any suitable FRET pair system can be provided in kits of the invention.

In some embodiments, the kits of the invention can include oligonucleotide probes suitable for HCV amplicon quantitation, e.g., TaqMan-type probes specific for HCV base sequences located within the HCV amplicon. For example, the invention provides the HCV quantitation probe of SEQ ID NO: 60. It is understood, however, that the kits of the invention are not limited to this one quantitation probe, as one of skill in the art will recognize that the invention (and kits of the invention) can comprise any suitable quantitation probe.

In addition, kits of the present invention can also include, for example but not limited to, apparatus and reagents for sample collection and/or sample purification (e.g., isolation of RNA from a blood sample), sample tubes, holders, trays, racks, dishes, plates, instructions to the kit user, solutions, buffers or other chemical reagents, suitable samples to be used for standardization, normalization, and/or control samples (e.g., positive controls, negative controls or calibration controls). Kits of the present invention can also be packaged for convenient storage and shipping, for example, in a container having a lid. The components of the kits may be provided in one or more containers within the kit, and the components may be packaged in separate containers or may be combined in any fashion. In some embodiments, kits of the invention can provide materials to facilitate high-throughput analysis of multiple samples, such as multiwell plates that can be read in a suitable fluorescence spectrophotometer.

Detection/Correlation Systems of the Invention

In some embodiments, the invention provides integrated systems for correlating the detection of a signal with a hepatitis C virus type. The system can include instrumentation and means for interpreting and analyzing collected data, especially where the means for deriving the HCV type comprises algorithms and/or electronically stored information (e.g., collected fluorescence data, predetermined HCV type correlations, etc). Each part of an integrated system is functionally interconnected, and in some cases, physically connected. In some embodiments, the integrated system is automated, where there is no requirement for any manipulation of the sample or instrumentation by an operator following initiation of the HCV typing analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure hybridization of the HCV typing probe with the HCV target amplicon (during the melting curve analysis when $T_m$ is being measured), and optionally, to measure accumulation of the HCV amplicon during HCV quantitation (e.g., with a TaqMan-type probe). A detector can be in the form of a multiwell plate reader to facilitate the high-throughput capacity of an HCV typing assay. In some embodiments, the fluorescence spectrophotometer is a multi-channel spectrophotometer that allows excitation and emission detection in two or more channels.

In some embodiments, the integrated system includes a thermal cycling device, or thermocycler, for the purpose of controlling the temperature of a reaction, e.g., during the phases of an RT-PCR reaction, or during melting analysis when $T_m$ is to be determined. In some embodiments, the thermal cycling device and the detector are an integrated instrument, where the thermal cycling and emission detection (e.g., fluorescence detection) are done in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the HCV type of the sample is determined (electronically). In some embodiments, the correlation module comprises a computer program that calculates the Tm based on the fluorescence readings from the detector and furthermore derives the HCV type of the unknown sample based on the fluorescence and Tm data. In some embodiments, the correlation module compares the hybridization property (e.g., $T_m$) of the unknown sample with a database (or table) of values for known HCV types to make a correlation between the hybridization property of the unknown sample and the HCV type of the unknown sample.

In some embodiments, the correlation module in the system determines the type of an HCV, where the type is selected from one of five genotypes, or one of six subtypes. A correlation module can comprise, among other features, experimentally predetermined values for hybridization properties of hybridization complexes that contain known HCV types, or the correlation module can comprise predicted values for hybridization properties of hybridization complexes that contain known HCV types. Alternatively, the correlation module can rely on experimentally determined values for hybridization properties of hybridization complexes that contain known HCV types that are obtained at the same time as the experimental sample with the HCV of unknown type.

With a suitable correlation module and a suitable probe, a system of the invention can assign a type to an HCV in a sample, where the type is selected from more than five genotypes, and preferably, from as many as 11 or more genotypes. For example, depending on the instrumentation used, the Tm of a particular hybridization complex can be determined with a variable degree of accuracy. For example, some Tm apparatus (a combined thermal cycling apparatus and coupled fluorescence spectrophotometer) from one manufacturer can have an accuracy of ±1.0° C., while a second apparatus from a different manufacturer can have an accuracy of ±0.1° C. Use of the more sensitive apparatus will allow the differentiation of a greater number of HCV types if the Tm values are closely clustered together. Similarly, using suitably sensitive apparatus, there is the potential to be able to determine the type of an HCV in a sample, where the type can be assigned to far more than six subtypes, as there are as many as 78 or more known HCV subtypes.

A system of the invention is not limited to the use of $T_m$ as the sole distinguishing hybridization property of a hybridization complex. For example, HMA (heteroduplex mobility analysis), DHPLC (denaturing HPLC), CFLP (cleavase fragment length polymorphism), TGCE (thermal gradient capillary electrophoresis); SURVEYORT™ nuclease mutation detection kits, and SSCP (single strand conformation polymorphism), can all be used to distinguish hybridization complexes with different properties, and therefore, can be used to assign one or more type designation to an HCV sample.

A typical system of the invention can include two or more HCV typing probes (see, e.g., the probes provided in FIG. 6), one or more HCV quantitation probe (e.g., the quantitation probe of SEQ ID NO: 60), primers suitable for HCV amplification (for example, the primer pair provided in SEQ ID NOS: 58 and 59), a suitable detector (with or without an integrated thermal cycling instrument), a computer with a correlation module, and instruction (electronic or printed) for the system user. Typically, the system includes a detector that is configured to detect one or more signal outputs from the set of HCV typing probes and/or the HCV quantitation probes. In some embodiments, the HCV typing probe and the HCV quantitation probe have the same signal output (and therefore can use the same detector). In some embodiments, the system can further contain reagents used in the HCV typing or HCV typing/quantitation analysis. These can include but are not limited to one or more of a DNA polymerase with RT activity, suitable buffers, contamination control reagents (e.g., dUTP and/or UNG nuclease), stabilizing agents, dNTPs, soluble quenchers, etc. Kits can be supplied to operate in conjunction with one or more systems of the invention.

A wide variety of signal detection apparatus is available, including photo multiplier tubes, spectrophotometers, CCD arrays, scanning detectors, phototubes and photodiodes, microscope stations, galvo-scans, microfluidic nucleic acid amplification detection appliances and the like. The precise configuration of the detector will depend, in part, on the type of label used with the HCV typing and/or quantitation probes. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is commonly used for detection of amplified nucleic acids (however, upstream and/or downstream operations can also be performed on amplicons, which can involve other detection methods). In general, the detector detects one or more label (e.g., light) emission from a probe label.

The detector(s) optionally monitors one or a plurality of signals from an amplification reaction. For example, the detector can monitor optical signals which correspond to "real time" amplification assay results, as with the HCV quantitation (TaqMan-type) probe.

System instructions that correlate a detected signal with an HCV type (e.g., a genotype or a subtype) are also a feature of the invention. For example, the instructions can include at least one look-up table that includes a correlation between the detected signal and the HCV type. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the detected signal and the HCV type. The instructions also typically include instructions providing a user interface with the system, e.g., to permit a user to view results of a sample analysis and to input parameters into the system.

The system typically includes components for storing or transmitting computer readable data detected by the methods of the present invention, e.g., in an automated system. The computer readable media can include cache, main, and storage memory and/or other electronic data storage components (hard drives, floppy drives, storage drives, etc.) for storage of computer code. Data representing HCV types by the method of the present invention can also be electronically, optically or magnetically transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a blood or blood products from a patient. The material comprising the sample can be isolated or partially purified or purified. In some aspects, the sample material comprises RNA, polyA RNA, cRNA, total RNA, cDNA, amplified cDNA, or the like.

The phrase "system that correlates" in the context of this invention refers to a system in which data entering a computer corresponds to physical objects or processes or properties external to the computer, e.g., a hepatitis C virus, and a process that, within a computer, causes a transformation of the input signals to different output signals. In other words, the input data, e.g., the fluorescence readings from a melting curve, is transformed to output data, e.g., the HCV type such as a genotype or a subtype. The process within the computer is a set of instructions, or "program," by which positive amplification or hybridization signals are recognized by the integrated system and attributed to individual samples as an HCV type. Additional programs correlate the identity of individual samples with phenotypic values, e.g., statistical methods. In addition there are numerous programs for computing, e.g., C/C++, Delphi and/or Java programs for GUI interfaces, and productivity tools (e.g., Microsoft Excel and/or SigmaPlot) for charting or creating look up tables of relevant HCV typing or HCV quantitation correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as Visual Basic are also suitably employed in the integrated systems of the invention.

For example, HCV typing probe $T_m$ values assigned to a particular HCV type can be recorded in a computer readable medium, thereby establishing a database corresponding $T_m$ with unique HCV type (or a subset of HCV types). Any file or folder, whether custom-made or commercially available (e.g., from Oracle or Sybase) suitable for recording data in a computer readable medium can be acceptable as a database in the context of the invention. Data regarding HCV type analysis as described herein can similarly be recorded in a computer accessible database. Optionally, HCV typing data can be obtained using an integrated system that automates one or more aspects of the assay (or assays) used to determine the HCV type. In such a system, input data corresponding to HCV types can be relayed from a detector, e.g., an array, a scanner, a CCD, or other detection device directly to files in a computer readable medium accessible to the central processing unit. A set of system instructions (typically embodied in one or more programs) encoding the correlations between $T_m$ and the HCV types can be then executed by the computational device to identify correlations between $T_m$ and HCV type.

Typically, the system also includes a user input device, such as a keyboard, a mouse, a touchscreen, or the like, for, e.g., selecting files, retrieving data, reviewing tables of $T_m$ values, etc., and an output device (e.g., a monitor, a printer, etc.) for viewing or recovering the product of the statistical analysis.

Thus, in one aspect, the invention provides an integrated system comprising a computer or computer readable medium comprising set of files and/or a database with at least one data set that corresponds to predetermined or experimental $T_m$ values. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as. Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., samples) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support can be a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent Technologies (Palo Alto, Calif.).

Systems for HCV typing of the present invention can, thus, include a digital computer with one or more of high-throughput liquid control software, thermocycler control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes. The image scanner interfaces with the image analysis software to provide a measurement of, e.g., nucleic acid probe label intensity during HCV amplification or during HCV melting curve analysis, where the probe label intensity measurement is interpreted by the data interpretation software to show whether, and to what degree, the labeled probe hybridizes to a target. The data so derived is then correlated with sample identity, to determine the HCV type in a particular sample, and optionally, determine the load (e.g., concentration) of an HCV in a sample.

EXAMPLES

The following examples are offered to illustrate, but not to limit the claimed invention. One of skill will recognize a variety of non-critical parameters that may be altered and alternative reagents that can be utilized without departing from the scope of the claimed invention.

Example 1

HCV Typing Probes for Use in Multiprobe, Dual Channel HCV Typing Analysis

A collection of HCV typing probes were designed and synthesized. The probes were chemically synthesized. These probes are listed in FIG. 6. Each of these probes hybridizes to a domain within the 5'-UTR of the HCV genome showing sequence heterogeneity among at least two different HCV types (see, FIG. 5). Each of the probes listed in FIG. 6 satisfies the criteria that the probe by itself is able to differentiate at least two HCV types based on a distinguishing hybridization property of hybridization complexes comprising the probe. In this case, at least two HCV types can be distinguished using each of these probes in FIG. 6 based on $T_m$ values of hybridization complexes using the probes.

Some of the probes listed in FIG. 6 comprise labels, for example 6-carboxy-fluorescein (FAM), 2',4,4',5',7,7'-hexachlorofluorescein (HEX), or the rhodamine derivative JA270 (see, U.S. Pat. No. 6,184,379, issued Feb. 6, 2001, to Josel et al.). In some embodiments, probe combinations that have two different labels characterized by distinct excitation and emission spectra can be used in combination in a multi-dimensional HCV typing analysis. For example, in some embodiments, a FAM-labelled probe can be used in conjunction with a HEX-labelled probe in the same closed-tube reaction, and the two different probes can be sequentially excited and their emissions detected on a device that can detect emissions on two different wavelengths. For a FAM fluorescence measurement, an excitation filter at 485 nm with a 20 nm bandwidth, and an emission filter at 520 nm with a 10 nm bandwidth are used. For a HEX fluorescence measurements, an excitation filter at 540 nm with a 10 nm bandwidth, and an emission filter at 575 nm with a 25 nm bandwidth are used.

Some of the probes in FIG. 6 do not have any covalently attached label, e.g., AG0303A (SEQ ID NO: 14). In this case, the unlabelled probe can be used in conjunction with a suitable nucleic acid dye, e.g., the fluorescent dye SYBR® Green (AG0303A-SYBR; SEQ ID NO: 24) or ethidium bromide. Also note that in some embodiments as shown in FIG. 6, the same probe sequence can be used in different configuration (e.g., with or without different covalently attached labels, or with or without a 3'-terminal phosphate). For example, probe AG0203A has a variety of different configurations (SEQ ID NOS: 9-13), including variations in the covalently attached label and the presence or absence of the terminal phosphate. Also, for example, the probe AG0303A (SEQ ID NO: 14) has the same sequence as probe AG0303A-SYBR (SEQ ID NO: 24), except where it is intended that the probe described in SEQ ID NO: 24 be used in conjunction with SYBR® Green.

The probe sequences provided in FIG. 6 have been designed to provide modulated relative melting behavior (and as a result the $T_m$ values) by changing sequence length or adding modified bases (e.g., 5-propynyl-dU, 5-Me-dC or 2'-O-methyl bases), as well as by shifting or modifying the probe sequence.

Example 2

HCV Typing Using Multidimensional Tm Analysis with Probes AG0307M and AG0308K in a Single Reaction System The present example describes a dual-probe, dual-channel, closed-tube melting curve analysis ($T_m$ determination) using two HCV typing probes contained in a single RT-PCR and $T_m$ analysis reaction. This system is a "closed-tube" system, as the reaction mixture does not require any manipulation following the initiation of the RT-PCR reaction other than changing the external thermocycling conditions. Each HCV type analyzed is distinguishable from all of the other HCV types analyzed based on the combination of melting curve ($T_m$) analysis data for the two probes. This example illustrates the effectiveness of a multiprobe (i.e., multidimensional) analysis to differentiate at least five, and indeed more, HCV types.

Template RNA for generating HCV amplicons by RT-PCR was derived by in vitro transcription from plasmids carrying HCV genomic material inserts corresponding to types 1a, 2a, 3a, 4a, 5a and 6a. The sequences of these inserts correspond to the consensus sequences of each of the respective types as described in FIG. 5, except for type 2a. The HCV type 2a cloned insert is a type 2a quasispecies variant having a one nucleotide variation in the 5'-UTR domain targeted by the HCV typing probes. The relevant portion of the 5'-UTR sequence of this type 2a variant is also provided in FIG. 5, and in SEQ ID NO: 8. The material used to isolate the HCV genomic sequences was patient samples. Following the in vitro transcription, the RNA was purified by oligo-dT-sepharose chromatography and quantitated. The genotype/subtype of each plasmid HCV insert was previously confirmed using other assays, including sequencing.

Six different HCV RNA targets (corresponding to six different HCV types) were alternatively used in six RT-PCR/$T_m$ analysis reactions. The RT-PCR and the melting curve analyses were conducted in a single reaction mix without the need for any additional reagents, e.g., it was not necessary to add the HCV typing probes following the RT-PCR amplification.

Two HCV typing probes were used in this multi-probe analysis. These were the AG0307M probe (SEQ ID NO: 26; labelled with FAM), and AG0308K (SEQ ID NO: 54; labelled with HEX). Each of the six RT-PCR and Tm analysis reactions included both of these probes. These reactions were established as follows:

| Component | Concentration |
|---|---|
| poly rA carrier | 9 µg/mL |
| Glycerol | 6.2% |
| DMSO | 7.5% |
| Tricine, pH 8.3 | 50 mM |
| KOAc | 100 mM |
| dATP | 300 µM each |
| dCTP | |
| dGTP | |
| dUTP | 550 µM |
| ST280ATBUA1 amplification primer SEQ ID NO: 58 | 0.1 µM (10 pmol/rx) |
| ST778AATBA1 amplification primer SEQ ID NO: 59 | 0.5 µM (50 pmol/rx) |
| AG0307M-FAM HCV Typing Probe SEQ ID NO: 26 | 0.15 µM (15 pmol/rx) |
| AG0308K-HEX HCV Typing Probe SEQ ID NO: 54 | 0.15 µM (15 pmol/rx) |
| UNG (Uracil-N-Glycosylase) | 10 U/reaction |
| ZO5 polymerase | 40 U/reaction |
| Mn(OAc)$_2$ | 3 mM |
| New Methylene Blue | 10-25 µg/mL |
| HCV TARGET RNA | 10$^6$ copies per reaction |

| Amplification primer | Sequence | SEQ ID NO |
|---|---|---|
| ST280ATBUA1 | GCAGAAAGCGTCTAGCCATGGCGTTZ | 58 |
| ST778AATBA1 | GCAAGCACCCTATCAGGCAGTACCACAZ | 59 |

Z = N6-t-butylbenzyl-dA

Figure 10:
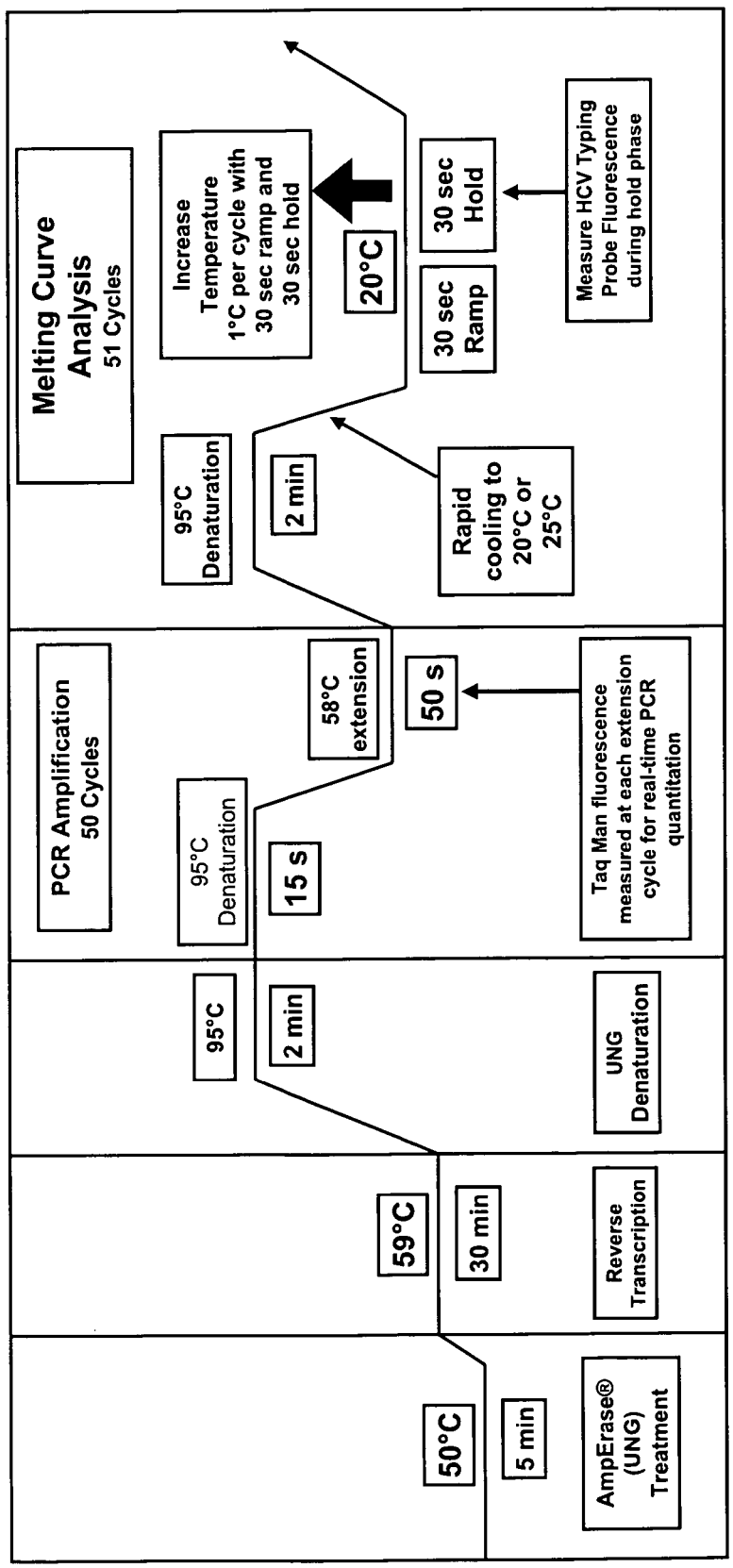
FIG. 10 provides a diagram detailing the thermocycling conditions used in a closed-tube RT-PCR and HCV genotyping (melting curve) experimental reaction. The optional use of TaqMan reagents for real-time PCR quantitation is also indicated.

Six separate asymmetric RT-PCR reactions were run using six different HCV targets, and using the above reaction mix with the thermal cycling conditions shown in FIG. 10. This thermal cycling program resulted in the RT-PCR amplification of the HCV transcript to generate the HCV amplicon. The reaction is initiated with an UNG decontamination step at 50° C. to eliminate any carry-over contamination by dU-containing polynucleotides. The reverse transcriptase reaction is then carried out at 59° C., where one of the PCR amplification primers also primes the reverse transcription. The RT-PCR reaction was an asymmetric reaction where one of the amplification primers was in 5-fold excess over the opposite primer, resulting in an overabundance of amplification of the HCV genomic strand that will hybridize to the HCV typing probe. The amplification with the indicated primers produced an approximately 200 base amplicon.

Following generation of the PCR amplicon, the thermal cycling program proceeded directly to a melting curve analysis. For the melting analysis, the various hybridization mixtures were heated to 95° C. for 2 min, followed by cooling to 20 or 25° C. to allow annealing and the formation of hybridization complexes. The reaction mix containing the hybridization complexes is then heated in approximately 50 one minute cycles where each cycle increases the temperature 1° C. (each one minute cycle consisted of a 30 second temperature ramp and a 30 second hold step).

Figure 1:
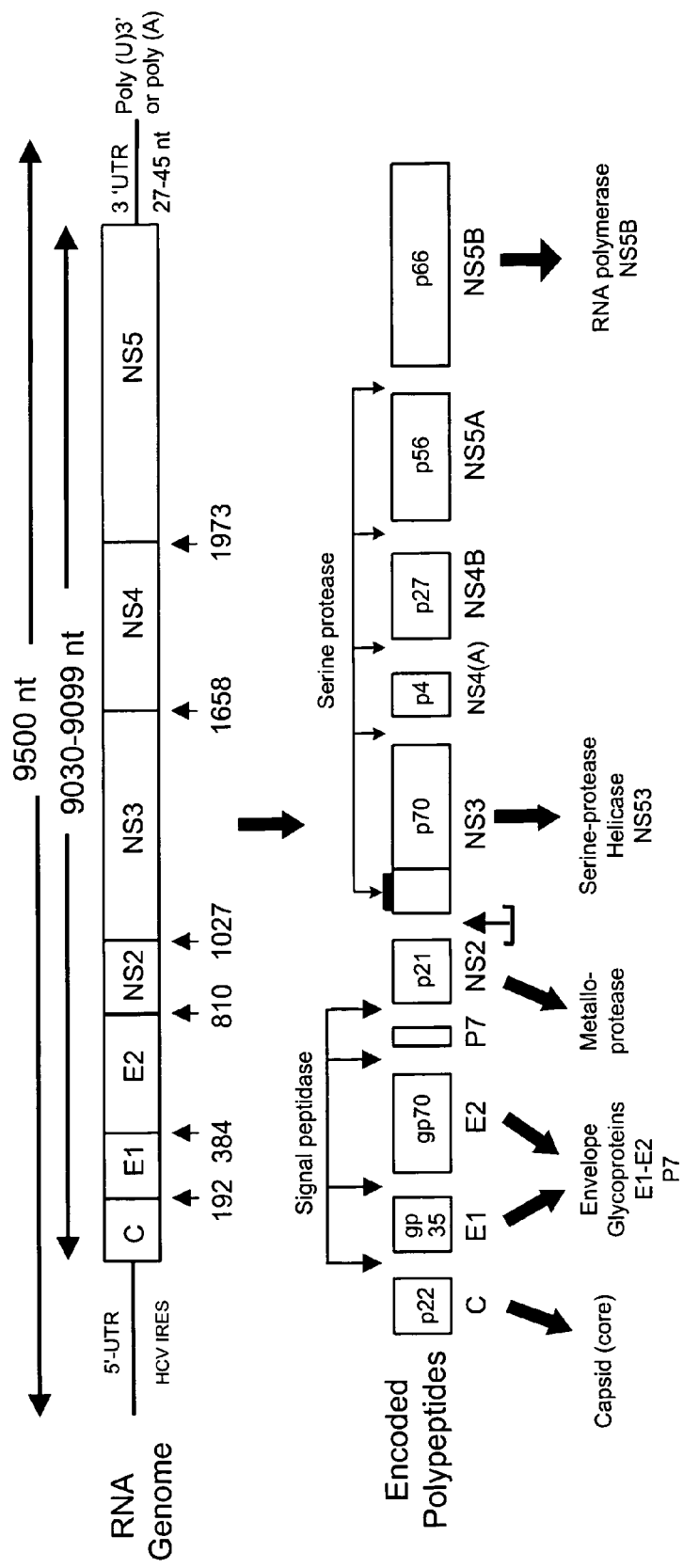
FIG. 1 provides a schematic representation of the HCV genome and the corresponding encoded polypeptides. Approximate lengths of the full length genome and the open reading frame are given. Polyprotein cleavage sites are also indicated. Exact sizes of the various genomic domains will vary depending on the HCV genotype and subtype.
Figure 7:
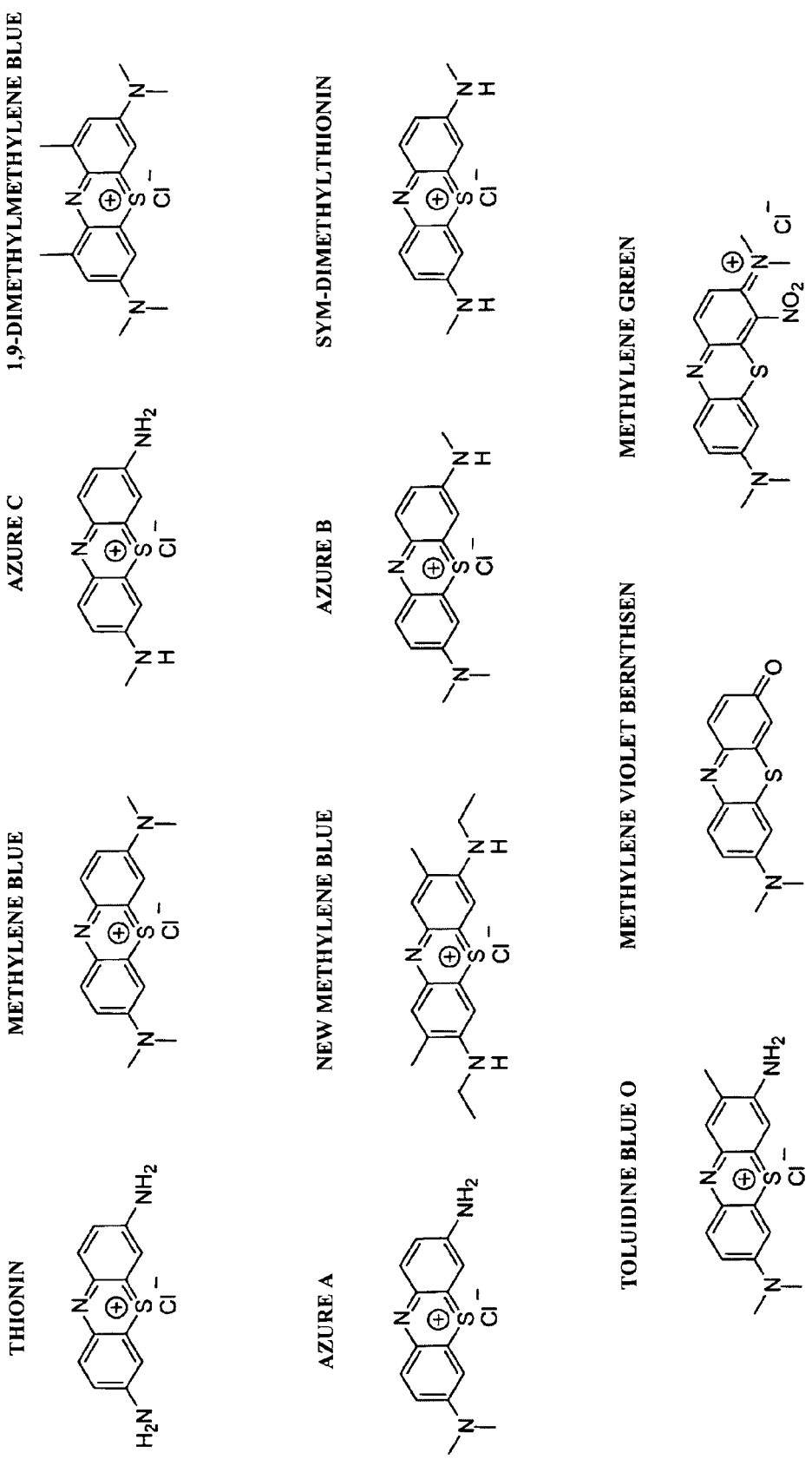
FIG. 7 provides examples of structures of thiazine dye soluble quenchers.

The formation/dissociation of hybridization complexes in the mix during the $T_m$ analysis was monitored by the use of a soluble quencher energy transfer system. The FAM and HEX labels covalently attached to their respective probes provided donor emissions. The quenching action was provided by the soluble quencher new methylene blue (see, FIG. 7). New methylene blue is a member of a family of soluble quenchers based on thiazine dye structures. The new methylene blue quencher has a binding affinity for double-stranded DNA, and thereby results in a quenching effect due to its close proximity to the fluorescent label on the probe when the probe is in a duplex structure with the target. However, the soluble quencher has reduced affinity for single-stranded DNA. Thus, when the solution containing the hybridization complex comprising the probe is heated and eventually dissociates, the affinity of the quencher for the nucleic acid is reduced, resulting in an increase in fluorescence. The new methylene blue soluble quencher was used at various concentrations generally ranging from 10-25 µg/mL. The optimal concentration of soluble quencher was determined empirically. Significantly, it was observed that the resolution of $T_m$ values (i.e., greater separation between $T_m$ values between the various HCV types) can be improved with some HCV typing probes by varying the soluble quencher concentration.

During the melting analysis, the FAM and HEX fluorescence levels were measured on two different channels for 50 milliseconds at the end of each 30 second hold step. The melting reactions were run in 96 well microtiter plates, and fluorescence on the two channels was monitored using a COBAS™ TaqMan™ 48 Analyzer from Roche Molecular Diagnostics (Roche Molecular Systems, Inc, Pleasanton, Calif.). Fluorescence in the FAM channel was measured using an excitation filter at 485 nm with a 20 nm bandwidth, and an emission filter at 520 nm with a 10 nm bandwidth. The HEX fluorescence channel was monitored using an excitation filter at 540 nm with a 10 nm bandwidth, and an emission filter at 575 nm with a 25 nm bandwidth.

The FAM and HEX fluorescence data were plotted separately. The collected FAM data, corresponding to the AG0307M probe, is shown graphically in FIG. 11 in a plot of raw fluorescence as a function of temperature. The results of six separate analyses (corresponding to each HCV type) were overlaid on the same plot in order to demonstrate the type-specific melting profiles. A set of representative data is shown.

Figure 11:
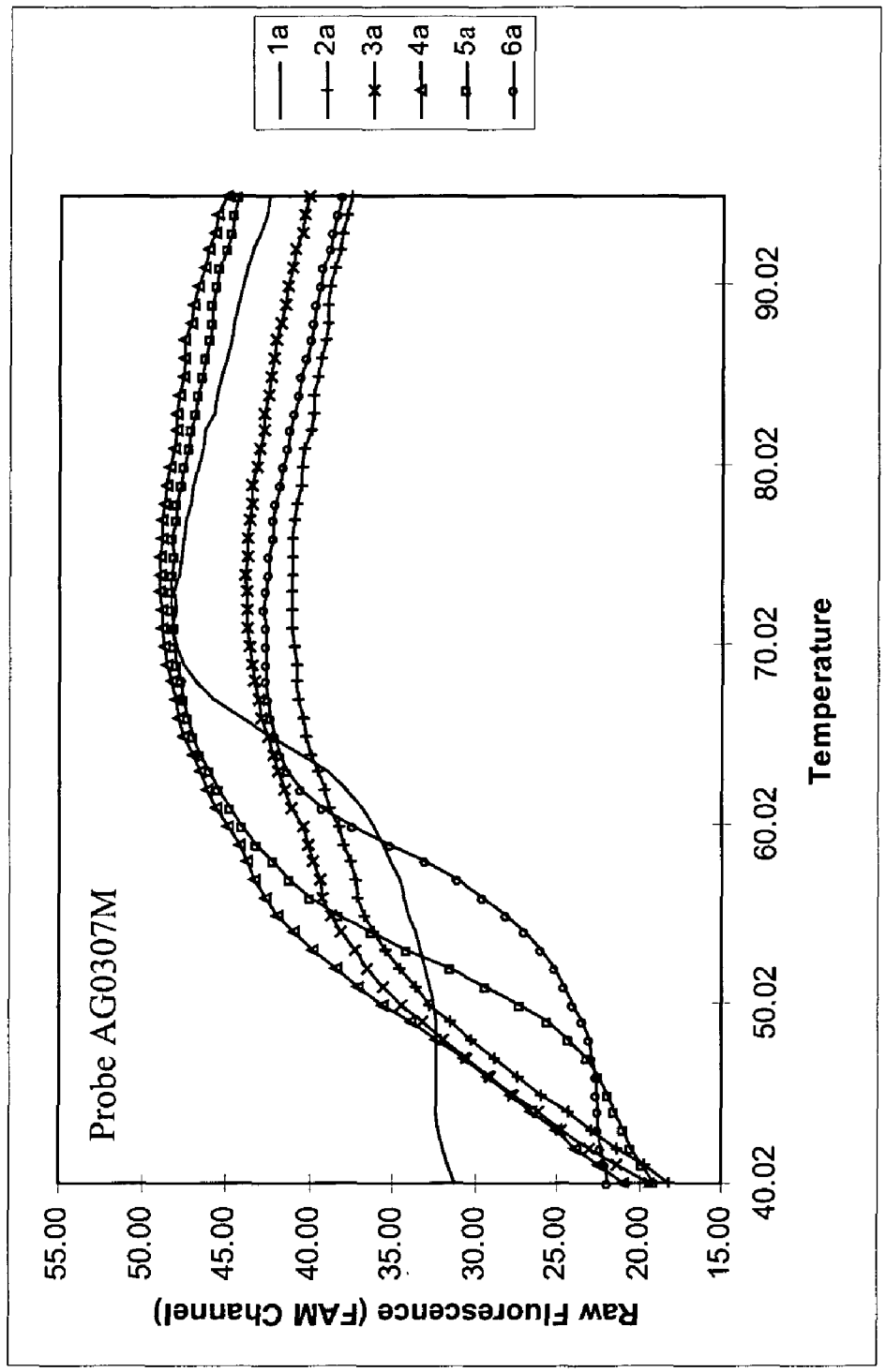
FIG. 11 provides a graph with the results of a closed-tube, dual-probe, dual-channel RT-PCR and HCV typing melting curve analysis, where the graph plots the melting curve raw fluorescence data as a function of temperature. The RT-PCR reaction generated 5'-UTR amplicons from each of the genotypes indicated. The reaction mix for the analysis comprised both the AG0307M probe with a FAM label, and the AG0308K probe with a HEX label. The two fluorescence emission readings were measured on two different channels. The data is this figure is from the FAM channel, corresponding to the AG0307M probe. The results of six separate experiments corresponding to six HCV types are overlaid on the same graph. A set of representative data is shown.
Figure 12:
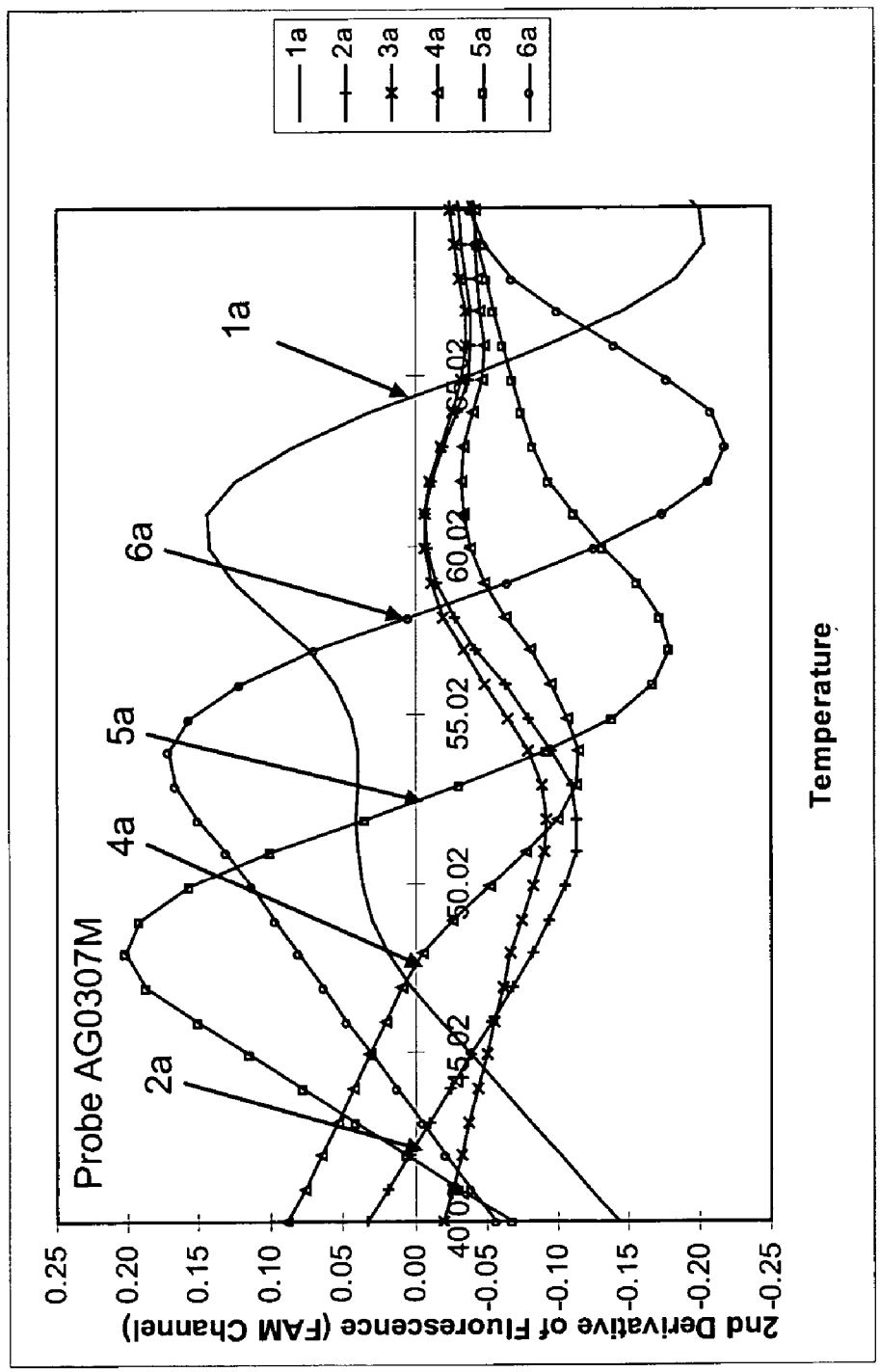
FIG. 12 provides a graph with the results of the closed-tube RT-PCR and HCV typing (melting curve) dual-probe analysis described in FIG. 11 on the FAM channel, using a second derivative plot.

The data in FIG. 11 can be more readily interpreted (and quantitated) by using a second derivative plot of the same data. FIG. 12 shows the data in FIG. 11 as a second derivative plot. The intersection of each curve with the zero value on the Y-axis represents the $T_m$ of the hybridization complex at those particular hybridization conditions. As can be seen using the AG0307M probe, the $T_m$ for HCV types 1a, 2a, 4a, 5a and 6a can be easily distinguished on the graph. However, in this case, the $T_m$ for type 3a can not be observed because it is below the 40° C. detection capability of the equipment being used.

Figure 13:
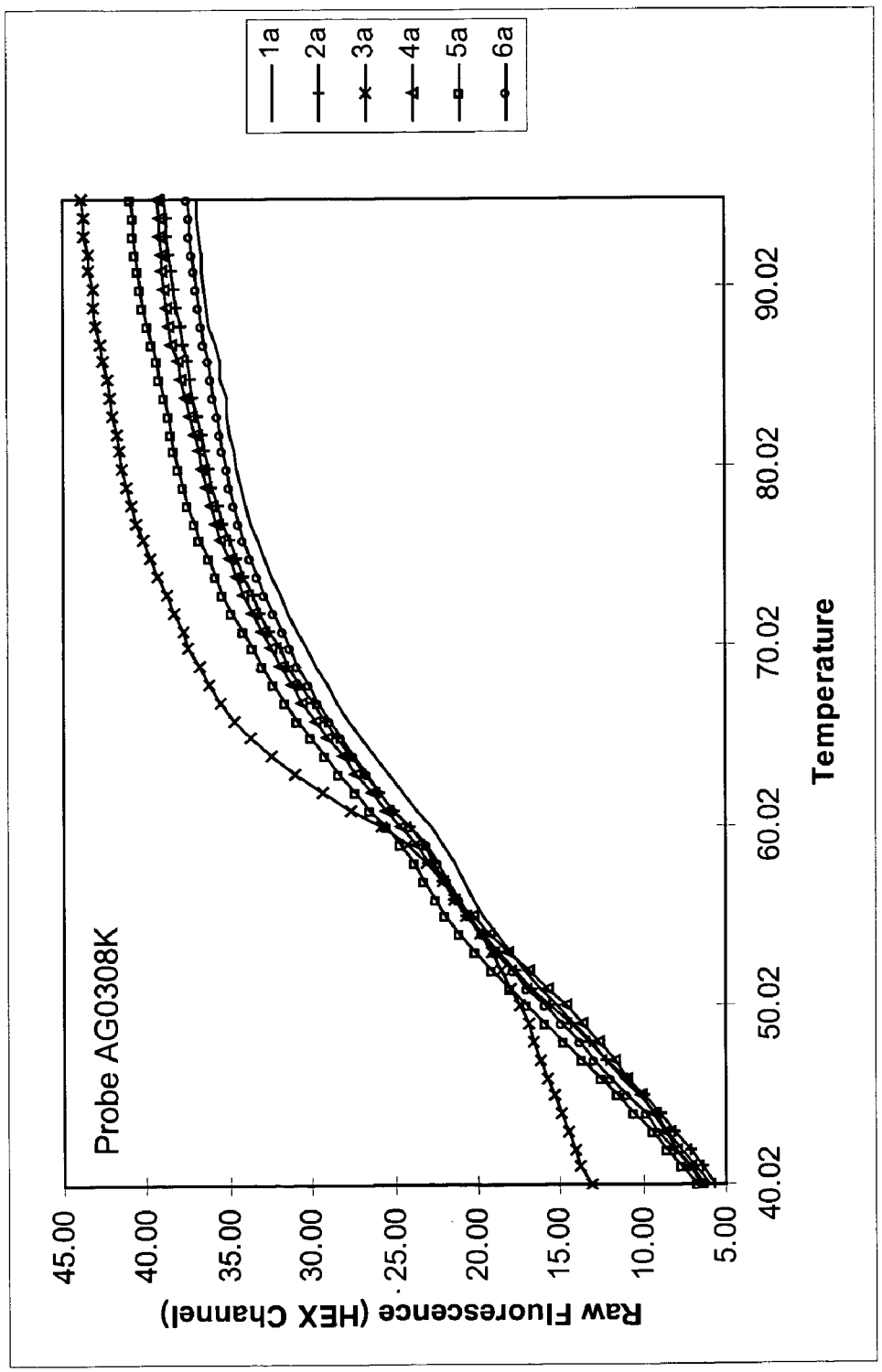
FIG. 13 provides a graph with the results of the closed-tube, dual-probe, dual-channel RT-PCR and HCV typing melting curve analysis in FIG. 11, except where the fluorescence is measured on the HEX channel, corresponding to the AG0308K probe. The plot shows the melting curve raw fluorescence data as a function of temperature. The results of six separate experiments corresponding to six HCV types are overlaid on the same graph. A set of representative data is shown.

Similarly, the fluorescence on the HEX channel, corresponding to probe AG0308K, is shown graphically in FIG. 13 in a plot of raw fluorescence as a function of temperature. The results of six separate analyses (corresponding to each HCV type) were overlaid on the same plot. A set of representative data is shown.

Figure 14:
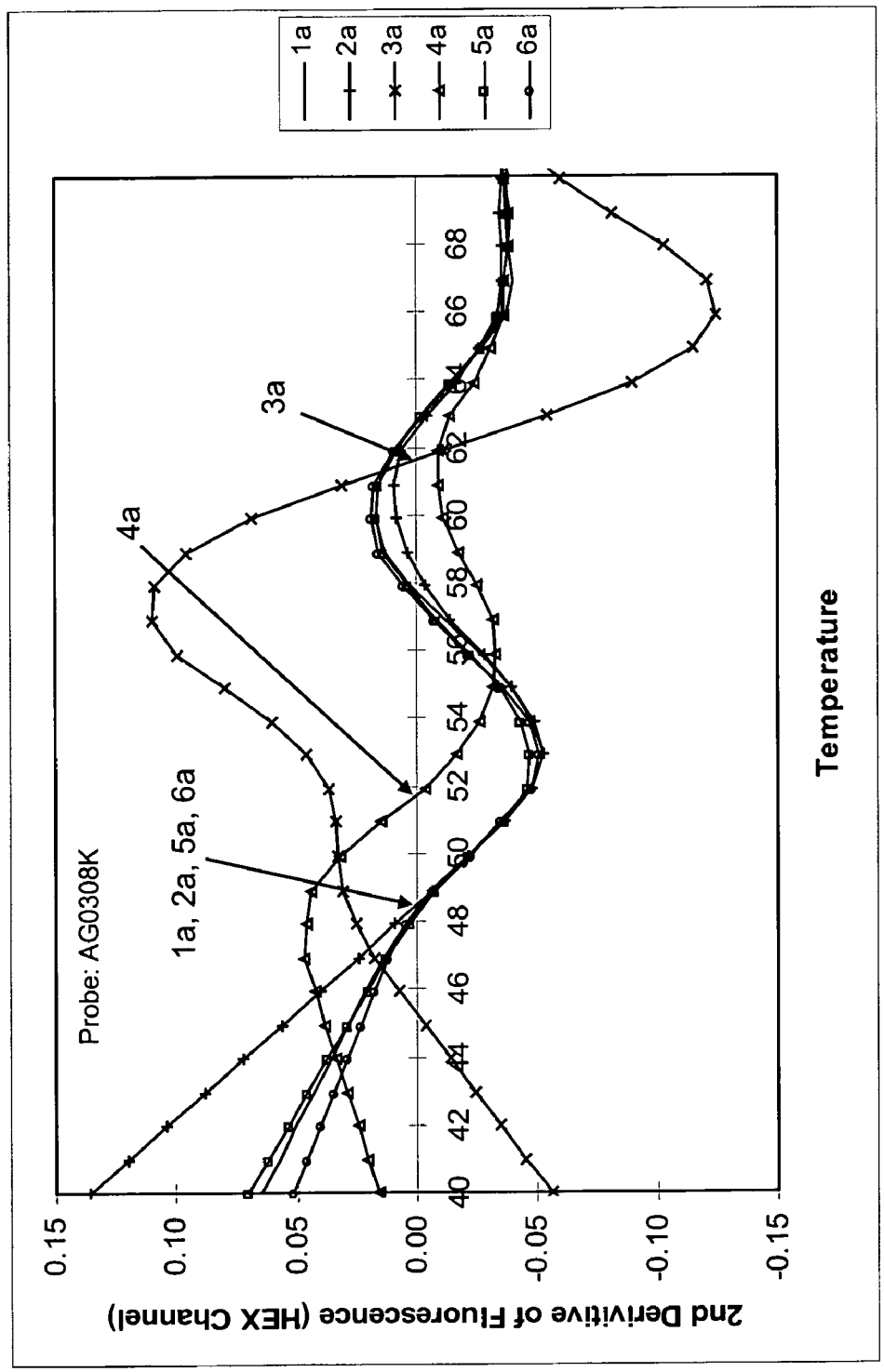
FIG. 14 provides a graph with the results of the closed-tube RT-PCR and HCV typing (melting curve) dual-probe analysis described in FIG. 13, using a second derivative plot.

The data in FIG. 13 is also plotted as a second derivative plot, as shown in FIG. 14. The intersection of each curve with the zero value on the Y-axis represents the $T_m$ of the hybridization complex at those particular hybridization conditions. As can be seen using the AG0308K probe, the $T_m$ for HCV type 3a can be distinguished from type 4a as well as the other remaining genotypes.

Figure 15:
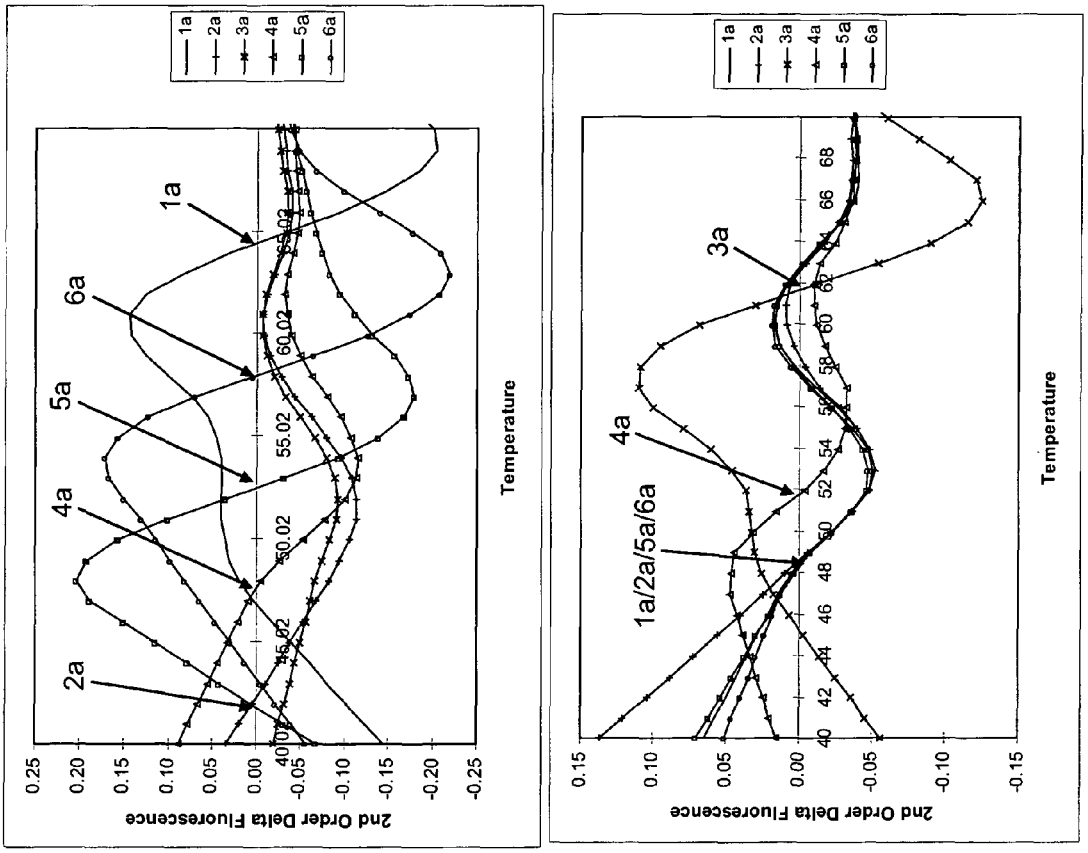
FIG. 15 provides a side-by-side comparison of the second derivative plots of FIGS. 12 and 14, read using the FAM channel and HEX channel, respectively. The $T_m$ values for each probe and each HCV type combination are indicated on the graphs.

FIG. 15 illustrates how the data from FIGS. 12 and 14 can be used in a complimentary fashion to make a definitive genotyping assignment. Although the assignment of type 3a remained ambiguous using probe AG0307M (in the FAM channel), that information can be obtained from probe AG0308K in the HEX channel. Probe AG0308K is able to make a definitive assignment to types 3a and 4a. Thus, these two data sets are complementary and provide enough information to make an HCV type assignment to types 1a, 2a, 3a, 4a, 5a or 6a. Using this technique, the number of HCV types that can be resolved using the combined datasets from the two probes is larger than the number of HCV types that can be definitively identified using either probe alone.

Example 3

HCV Typing Using Multidimensional $T_m$ Analysis with Probes AG0203A and AG0308J in a Single Reaction System Additional probe pairs were tested as described in EXAMPLE 2 above for their ability to provide mutually complementary datasets for HCV typing. These probe pairs were all tested in closed-tube, dual-channel systems where each probe pair is labelled with the FAM and HEX fluors. Separate $T_m$ determinations are made for each probe using the two emission channels. These examples further demonstrate the effectiveness of a multidimensional analysis to differentiate at least five or more HCV types.

The template RNA for generating HCV amplicons by RT-PCR was derived by in vitro transcription from plasmids carrying HCV genomic material inserts corresponding to types 1a, 2a, 3a, 4a, 5a and 6a, as described in EXAMPLE 2. Following the in vitro transcription, the HCV RNA was used in the RT-PCR/$T_m$ reactions. The RT-PCR and the melting curve analyses were conducted in a single reaction mix without the need for any additional reagents. The present EXAMPLE used HCV typing probes AG0203A-FAM (SEQ ID NO: 10; labelled with FAM), and AG0308J (SEQ ID NO: 53; labelled with HEX). The RT-PCR and $T_m$ analysis reactions were established as described in EXAMPLE 2. The RT-PCR and melting curve analysis used the thermal cycling conditions shown in FIG. 10.

During the melting analysis, the FAM and HEX fluorescence levels were measured on two different channels, and the FAM and HEX fluorescence data were plotted separately. The collected FAM data, corresponding to the AG0203A probe, is shown graphically in FIG. 16 in a plot of raw fluorescence as a function of temperature. The results of six separate analyses (corresponding to each HCV type) were overlaid on the same plot. A set of representative data is shown.

Figure 16:
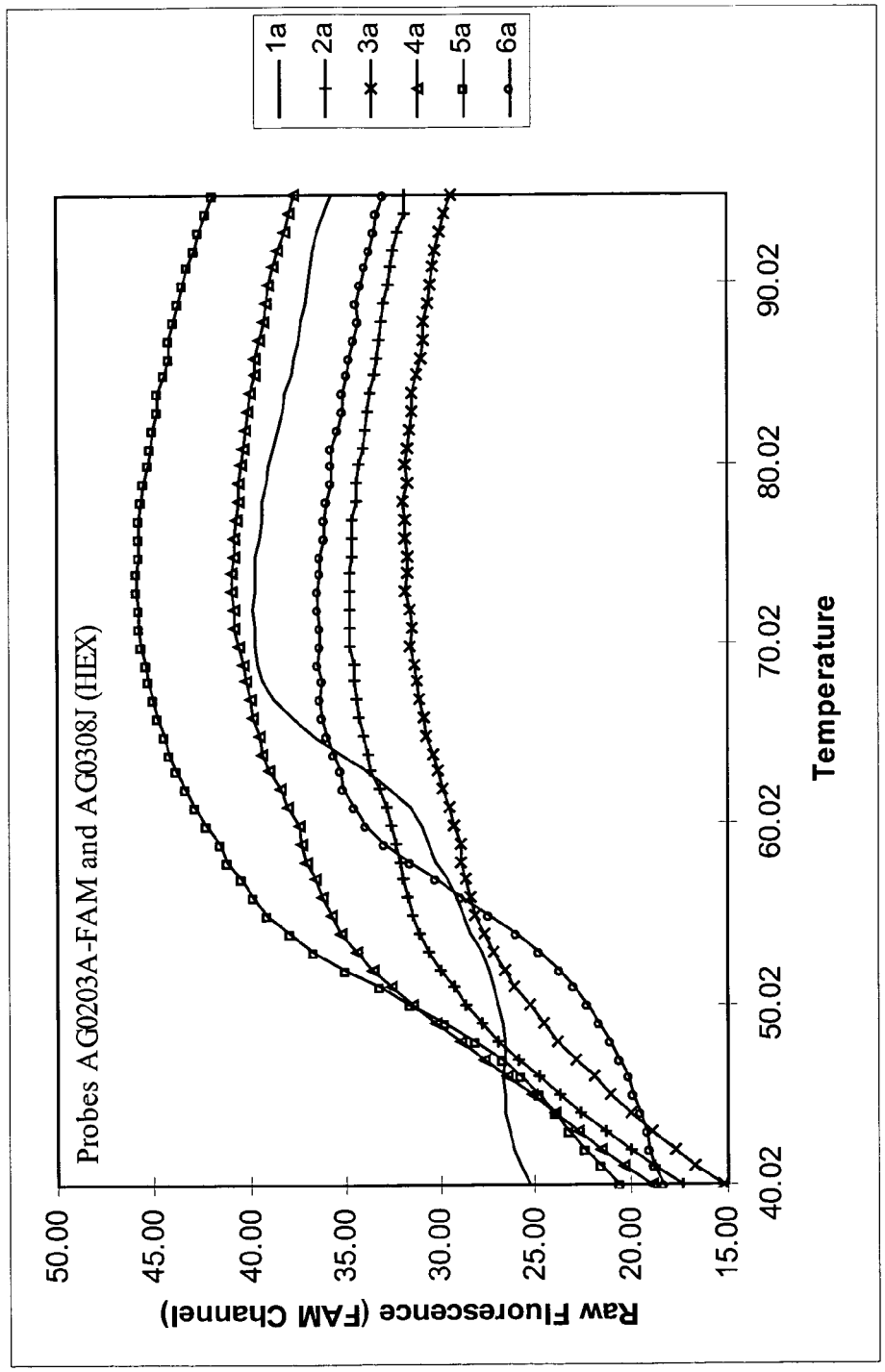
FIG. 16 provides a graph with the results of a closed-tube, dual-probe, dual-channel RT-PCR and HCV typing melting curve analysis, where the graph plots the melting curve raw fluorescence data as a function of temperature. The RT-PCR reaction generated 5'-UTR amplicons from each of the genotypes indicated. The reaction mix for the analysis comprised both the AG0203A probe with a FAM label, and the AG0308J probe with a HEX label. The two fluorescence emission readings were measured on two different channels. The data is this figure is from the FAM channel alone, corresponding to the AG0203A probe. The results of six separate experiments corresponding to six HCV types are overlaid on the same graph. A set of representative data is shown.
Figure 17:
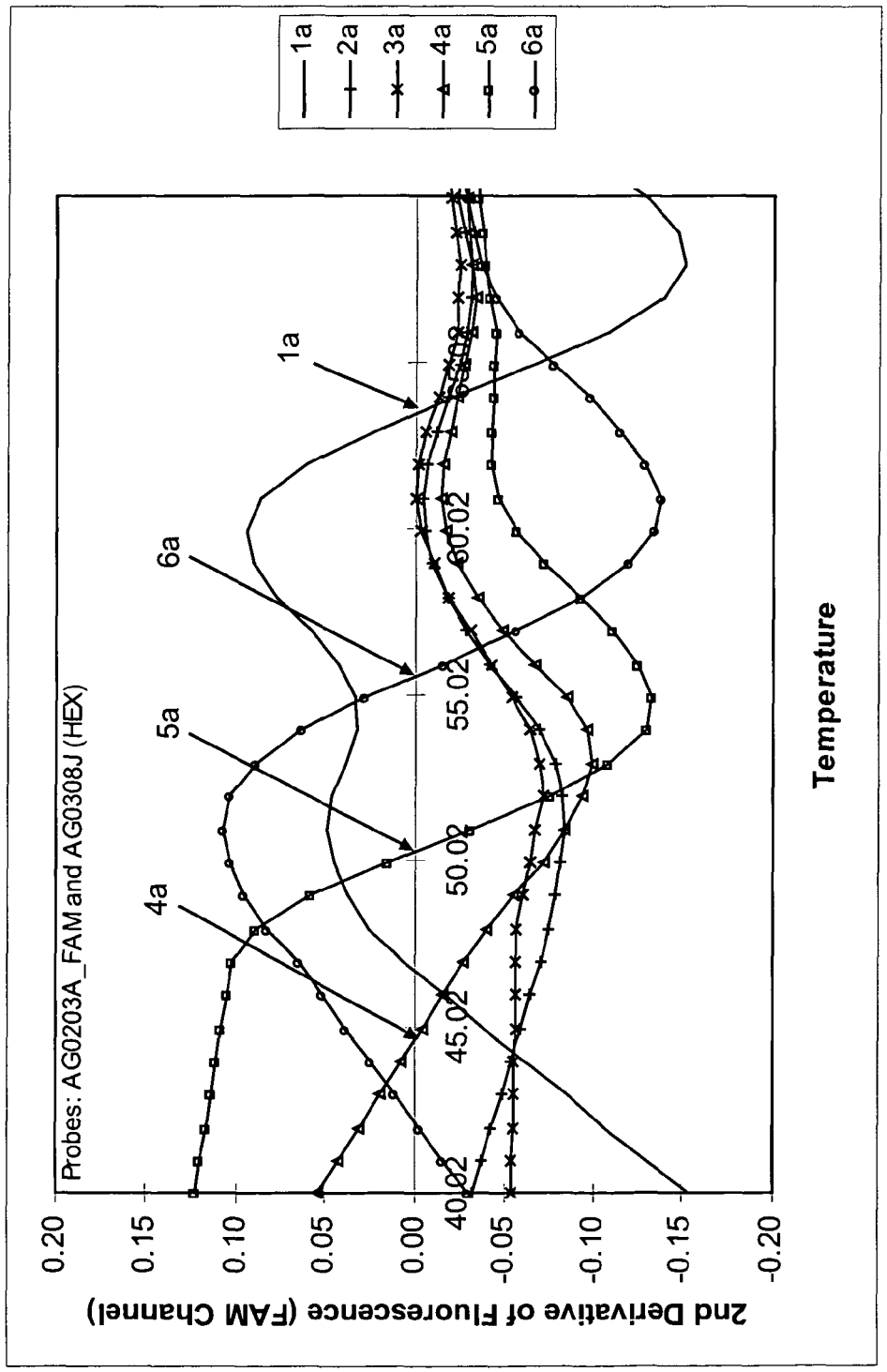
FIG. 17 provides a graph with the results of the closed-tube RT-PCR and HCV typing (melting curve) dual-probe analysis described in FIG. 16, using a second derivative plot.

The data in FIG. 16 can be more readily interpreted by using a second derivative plot of the same data. FIG. 17 shows the data in FIG. 16 as a second derivative plot. The intersection of each curve with the zero value on the Y-axis represents the $T_m$ of the hybridization complex at those particular hybridization conditions. As can be seen using the AG0203A probe, the $T_m$ for HCV types 1a, 6a, 5a and 4a can be easily distinguished on the graph. However, types 2a and 3a are not reported by this probe because melting points below 40° C. are below the practical detection limit for the particular instrumentation in this case.

Figure 18:
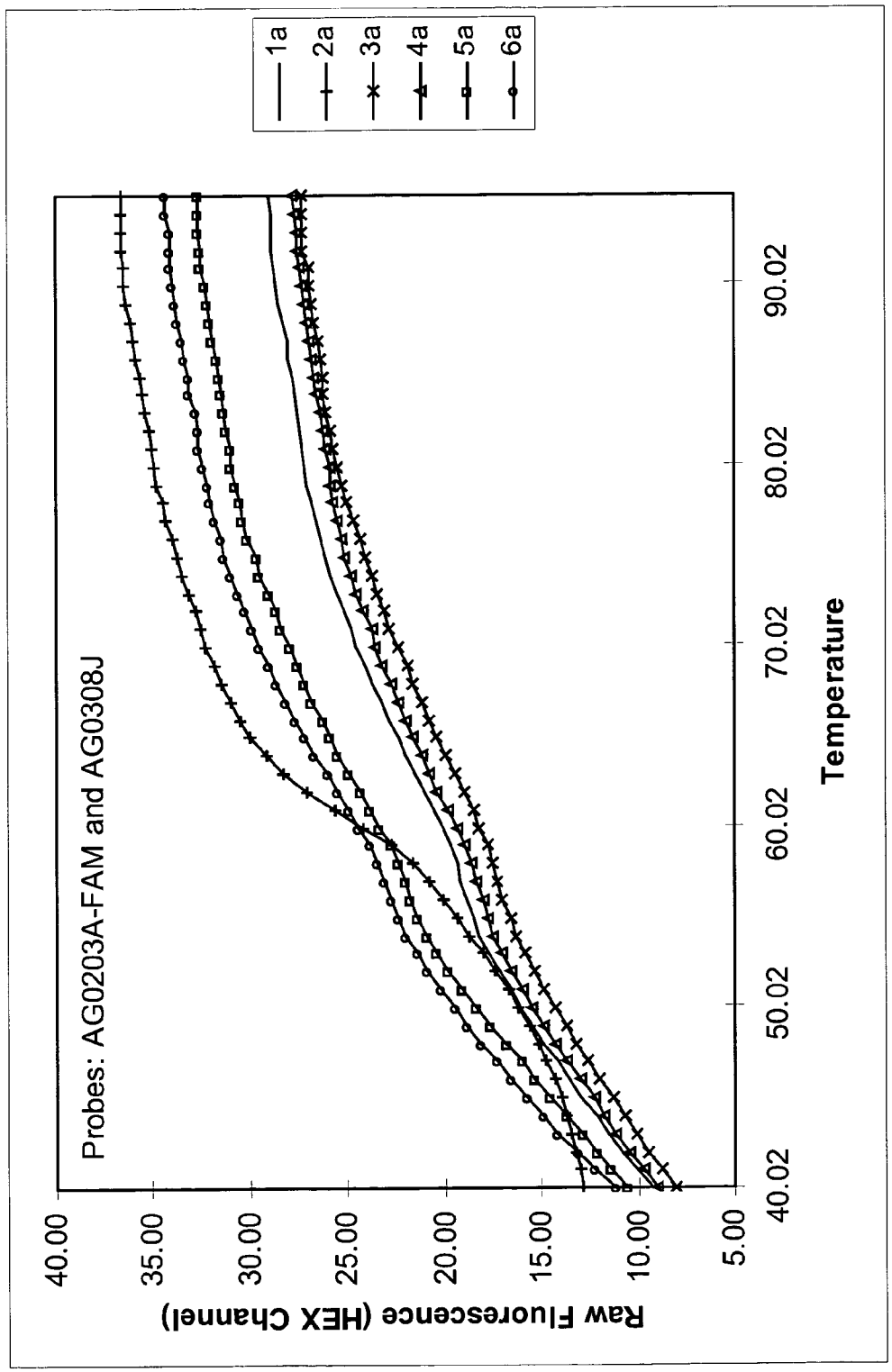
FIG. 18 provides a graph with the results of the closed-tube, dual-probe, dual-channel RT-PCR and HCV typing melting curve analysis in FIG. 16, except where the raw fluorescence is measured on the HEX channel alone, corresponding to the AG0308J probe. The results of six separate experiments corresponding to six HCV types are overlaid on the same graph. A set of representative data is shown.

Similarly, the fluorescence on the HEX channel, corresponding to probe AG0308J, is shown graphically in FIG. 18 in a plot of raw fluorescence as a function of temperature. The results of six separate analyses (corresponding to each HCV type) were overlaid on the same plot. A set of representative data is shown.

Figure 19:
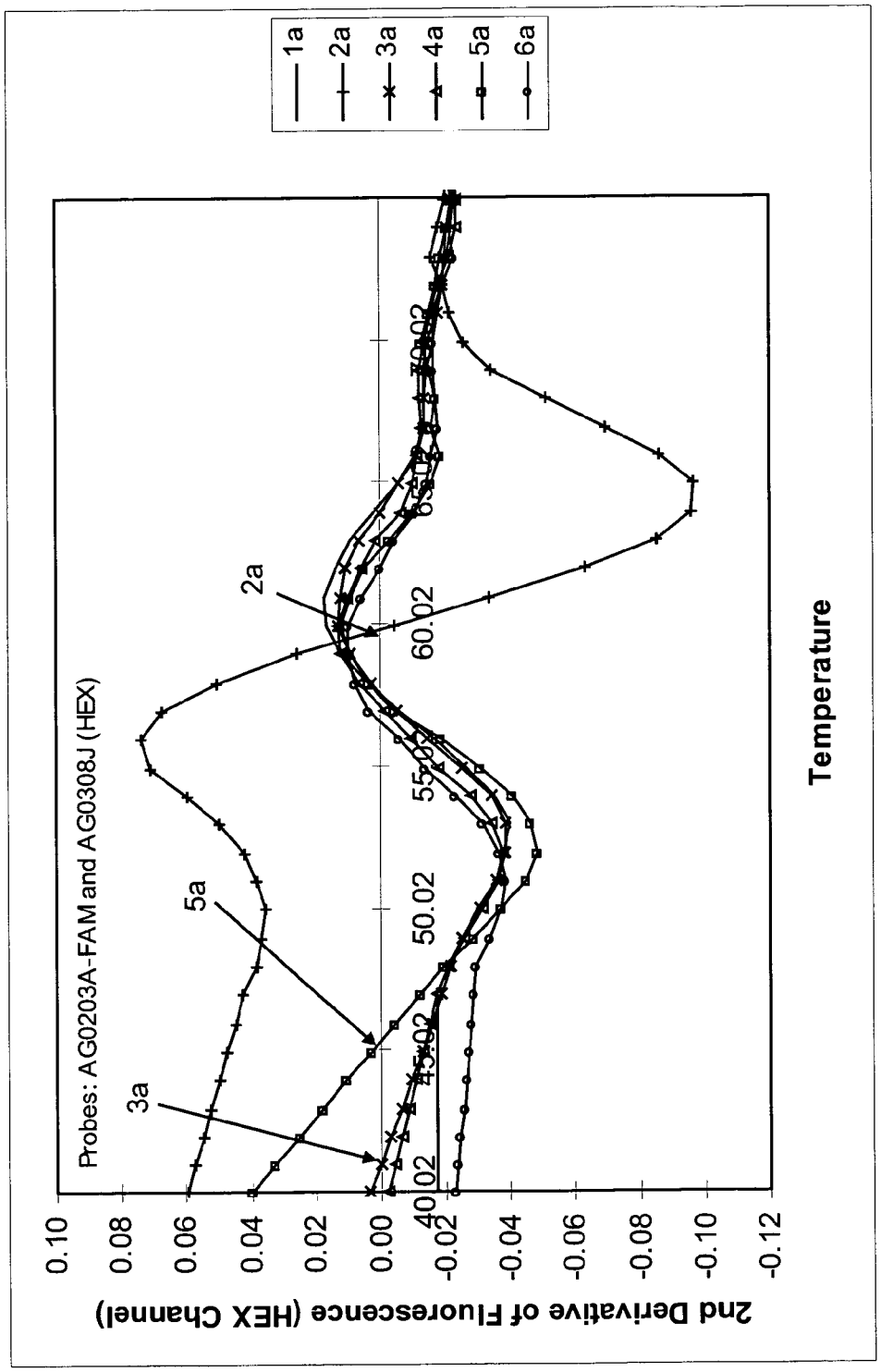
FIG. 19 provides a graph with the results of the closed-tube RT-PCR and HCV typing (melting curve) dual-probe analysis described in FIG. 18, using a second derivative plot.

The data in FIG. 18 is also plotted as a second derivative plot, as shown in FIG. 19. The intersection of each curve with the zero value on the Y-axis represents the $T_m$ of the hybridization complex at those particular hybridization conditions. As can be seen using the AG0308J probe, the $T_m$ for HCV types 2a and 5a can be distinguished from types 1a, 3a, 4a, and 6a, all of which have melting points near or below 40 C.

Figure 20:
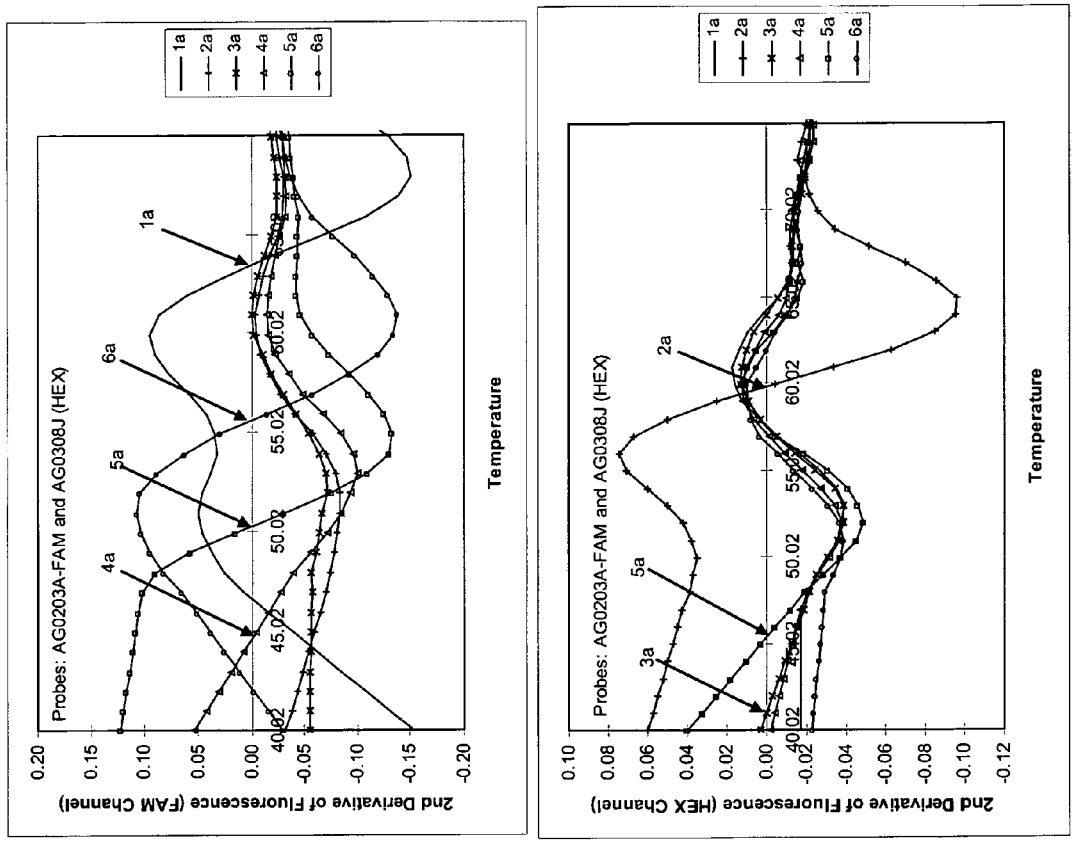
FIG. 20 provides a side-by-side comparison of the second derivative plots of FIGS. 17 and 19, read using the FAM channel and HEX channel, respectively. The $T_m$ values for each probe and each HCV type combination are indicated on the graphs.

FIG. 20 illustrates how the data from FIGS. 17 and 19 can be used in a complimentary fashion make a definitive genotyping assignment. Although the assignment of types 2a and 3a remained ambiguous using probe AG0203A (in the FAM channel), that information can be obtained from probe AG0308J in the HEX channel. Probe AG0308J is able to make a definitive assignment to types 2a and 5a. Thus, these two data sets are complementary and provide enough information to make an HCV type assignment to types 1a, 2a, 3a, 4a, 5a or 6a. Using this technique, the number of HCV types that can be resolved using the combined datasets from the two probes is larger than the number of HCV types that can be definitively identified using either probe alone.

Example 4

HCV Typing Using Multidimensional $T_m$ Analysis with Probes AG0308AA and AG0308H in a Single Reaction System A third probe pair was tested as described in EXAMPLE 2 for their ability to provide mutually complementary datasets for HCV typing. This probe pair also used the FAM and HEX fluors in a dual-channel system. This pair demonstrates again the effectiveness of a multidimensional analysis to differentiate at least five or more HCV types.

This pair of probes was used as described in EXAMPLE 2. The template RNA for generating HCV amplicons by RT-PCR was derived by in vitro transcription from plasmids carrying HCV genomic material inserts corresponding to types 1a, 2a, 3a, 4a, 5a and 6a. The HCV RNA was used in the RT-PCR/$T_m$ reactions. The RT-PCR and the melting curve analyses were conducted in a single reaction mix that included the probes AG0308AA (SEQ ID NO: 57; labelled with FAM), and AG0308H (SEQ ID NO: 52; labelled with HEX). The RT-PCR and $T_m$ analysis was done as described in EXAMPLE 2.

Figure 21:
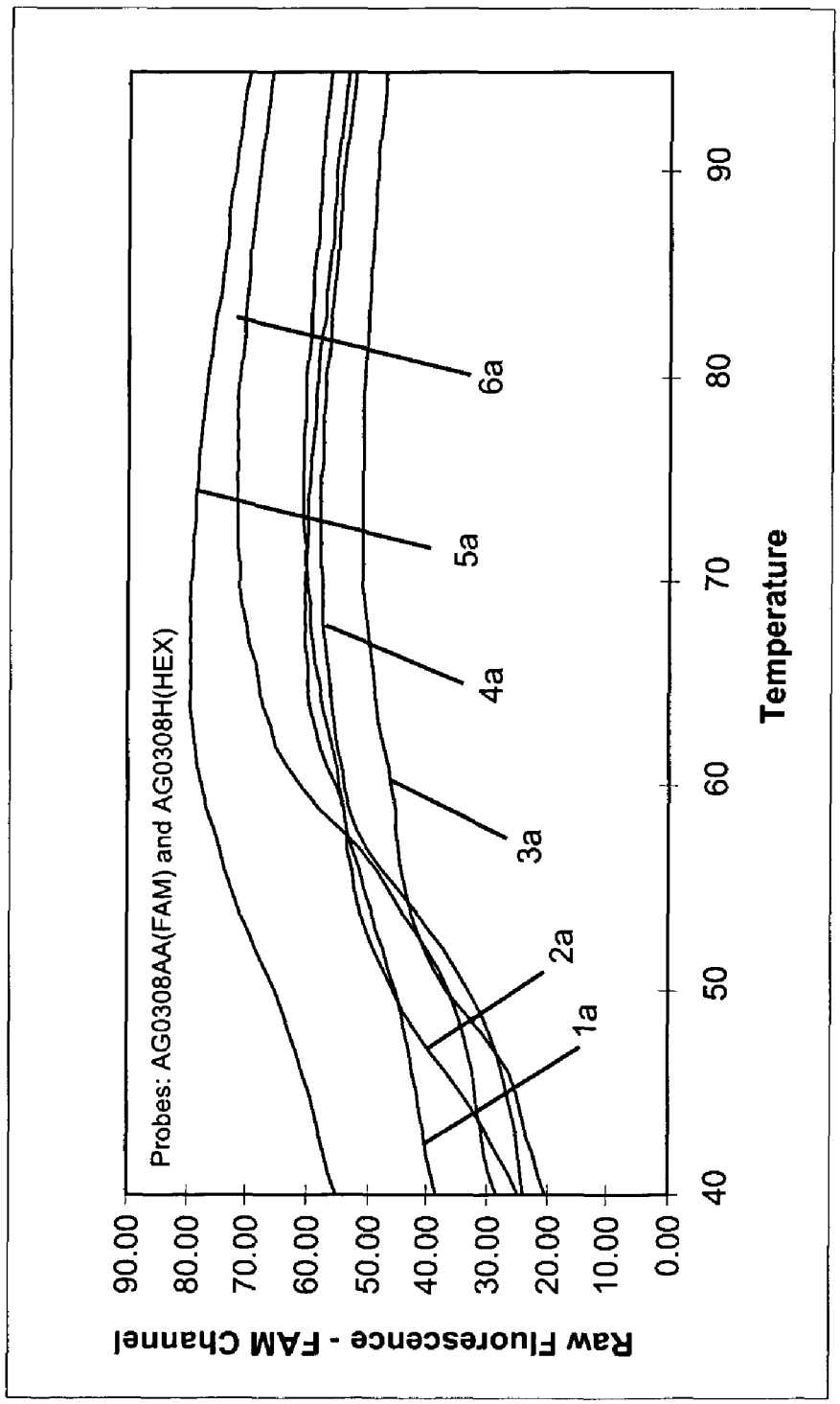
FIG. 21 provides a graph with the results of a closed-tube, dual-probe, dual-channel RT-PCR and HCV typing melting curve analysis, where the graph plots the melting curve raw fluorescence data as a function of temperature. The RT-PCR reaction generated 5'-UTR amplicons from each of the genotypes indicated. The reaction mix for the analysis comprised both the AG0308AA probe with a FAM label, and the AG0308H probe with a HEX label. The two fluorescence emission readings were measured on two different channels. The data is this figure is from the FAM channel alone, corresponding to the AG0308AA probe. The results of six separate experiments corresponding to six HCV types are overlaid on the same graph. A set of representative data is shown.

The collected FAM data, corresponding to the AG0308AA probe, is shown graphically in FIG. 21 in a plot of raw fluorescence as a function of temperature. The results of six separate analyses (corresponding to each HCV type) were overlaid on the same plot. A set of representative data is shown.

Figure 22:
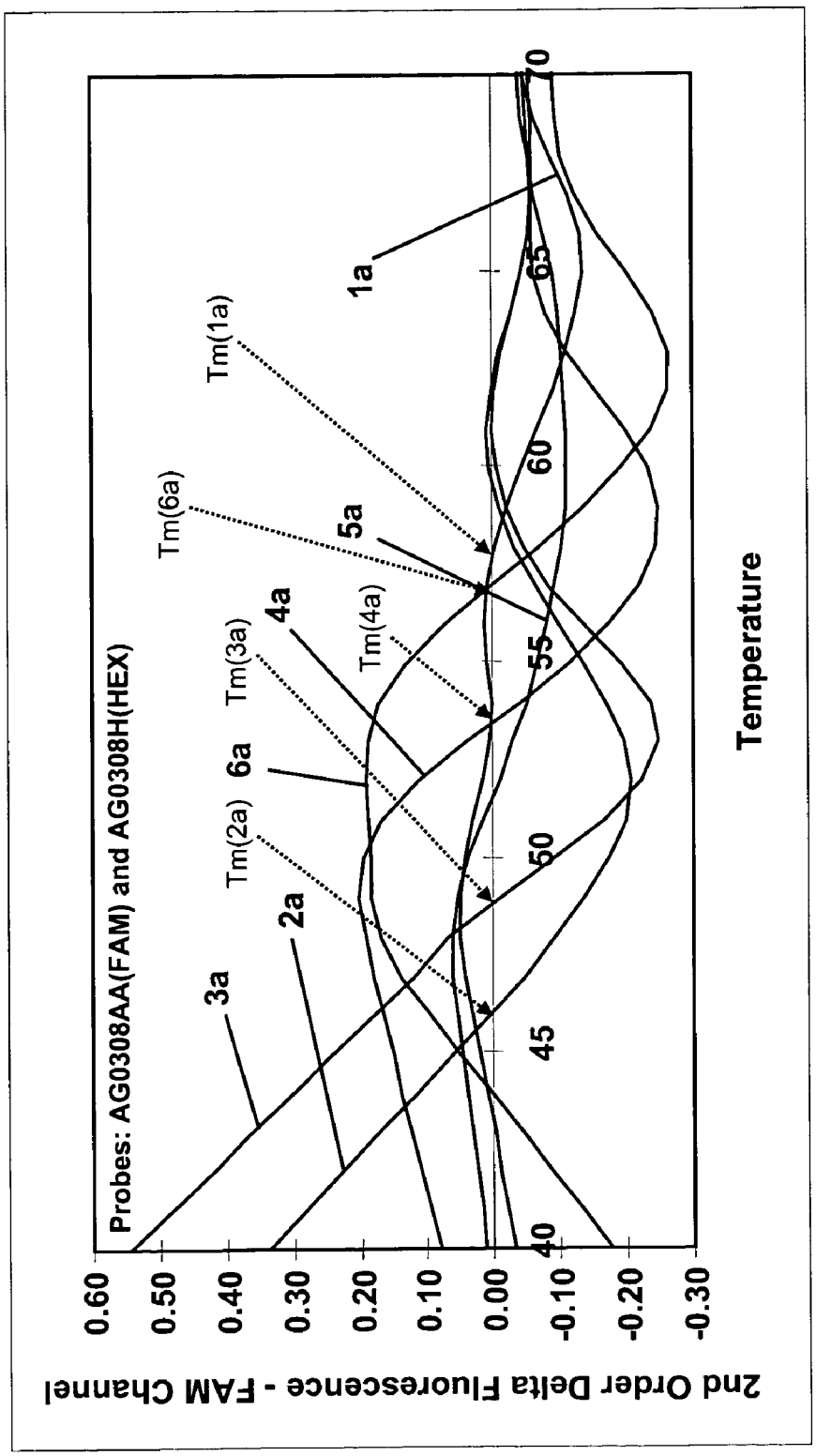
FIG. 22 provides a graph with the results of the closed-tube RT-PCR and HCV typing (melting curve) dual-probe analysis described in FIG. 21, using a second derivative plot.

The data in FIG. 21 can be more readily interpreted (and quantitated) by using a second derivative plot of the same data. FIG. 22 shows the data in FIG. 21 as a second derivative plot. The intersection of each curve with the zero value on the Y-axis represents the $T_m$ of the hybridization complex at those particular hybridization conditions. As can be seen using the AG0308AA probe, the $T_m$ for HCV types 1a, 4a, 3a and 2a can be easily distinguished on the graph. However, the $T_m$ for types 6a and 5a can not be resolved from each other.

Figure 23:
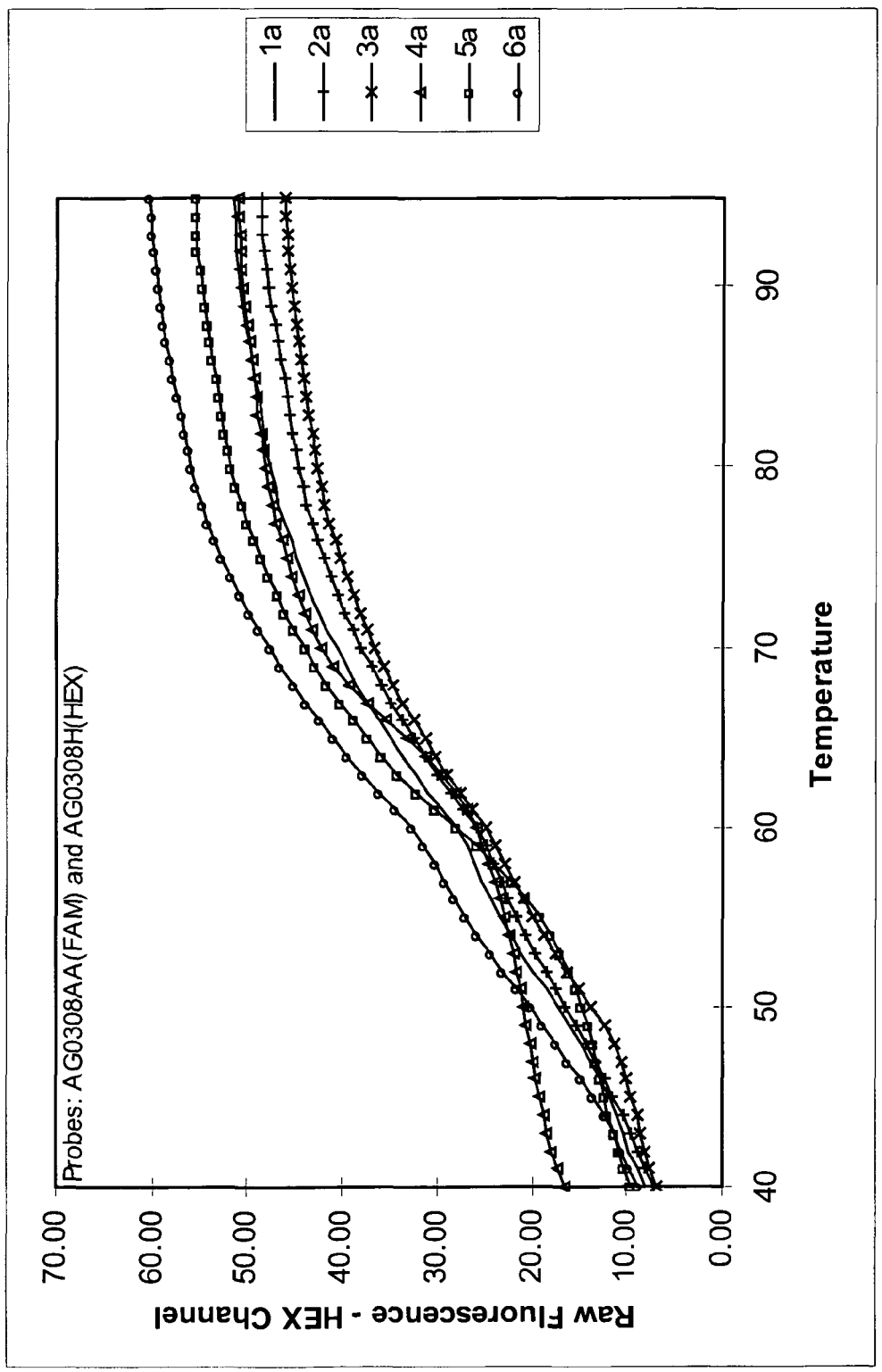
FIG. 23 provides a graph with the results of the closed-tube, dual-probe, dual-channel RT-PCR and HCV typing melting curve analysis in FIG. 21, except where the raw fluorescence is measured on the HEX channel alone, corresponding to the AG0308H probe. The results of six separate experiments corresponding to six HCV types are overlaid on the same graph. A set of representative data is shown.

Similarly, the fluorescence on the HEX channel, corresponding to probe AG0308H, is shown graphically in FIG. 23 in a plot of raw fluorescence as a function of temperature. The results of six separate analyses (corresponding to each HCV type) were overlaid on the same plot. A set of representative data is shown.

Figure 24:
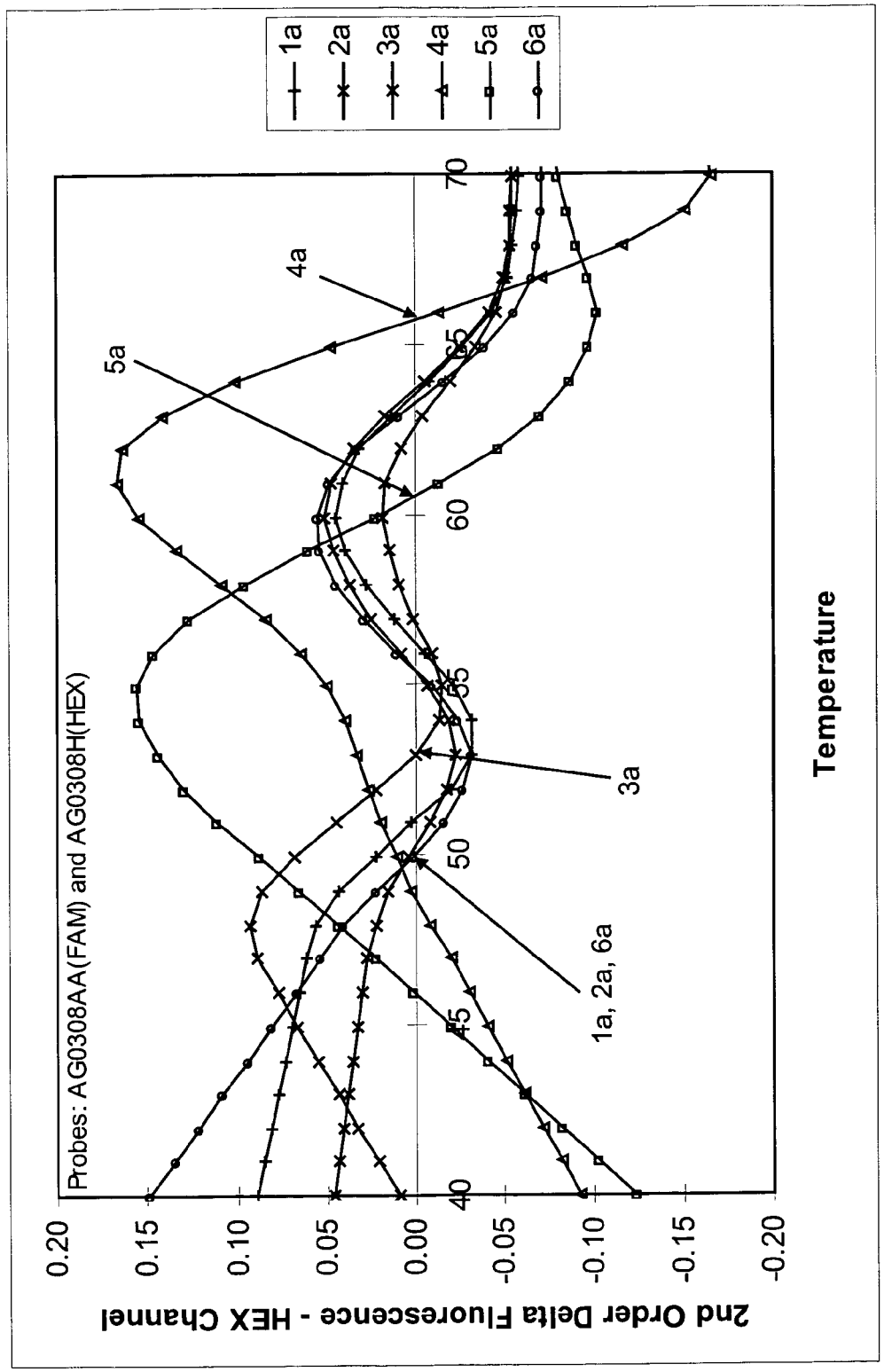
FIG. 24 provides a graph with the results of the closed-tube RT-PCR and HCV typing (melting curve) dual-probe analysis described in FIG. 23, using a second derivative plot.

The data in FIG. 23 is also plotted as a second derivative plot, as shown in FIG. 24. The intersection of each curve with the zero value on the Y-axis represents the $T_m$ of the hybridization complex at those particular hybridization conditions. As can be seen using the AG0308H probe, the $T_m$ for HCV types 4a, 5a and 3a can be distinguished from types 1a, 2a and 6a.

FIG. 25 illustrates how the data from FIGS. 22 and 24 can be used in a complimentary fashion make a definitive genotyping assignment. Although the assignment of types 6a and 5a remained ambiguous using probe AG0308AA (in the FAM channel), that information can be obtained from probe AG0308H in the HEX channel. Probe AG0308H is able to make a definitive assignment to types 4a, 5a and 3a. Thus, these two data sets are complementary and provide enough information to make an HCV type assignment to types 1a, 2a, 3a, 4a, 5a or 6a. Using this technique, the number of HCV types that can be resolved using the combined datasets from the two probes is larger than the number of HCV types that can be definitively identified using either probe alone.

Example 5

Multidimensional HCV Typing and Viral Quantitation in a Closed-Tube Reaction

This example describes a method for the simultaneous determination of HCV type and HCV viral load (i.e., HCV quantitation) in a closed-tube quantitation/typing reaction. This combined quantitation and typing reaction closed-tube system does not require any purification steps or addition of supplemental components once the reaction mix is made.

The HCV quantitation was accomplished by incorporating a suitable quantitation probe. The HCV quantitation takes place in the same reaction mix as the typing analysis by including a probe suitable for use in real-time monitoring of the accumulation of the HCV amplicon during the RT-PCR step. In these reactions, the reaction mixes included the TaqMan probe ST650AAFBHQ2 (SEQ ID NO: 60). $C_T$ and viral quantitation are calculated from the fluorescence profile during the RT-PCR amplification portion of the temperature cycling program.

The HCV typing was accomplished using reaction conditions essentially as described in EXAMPLE 2, namely by generating 5'-UTR HCV amplicons in an RT-PCR reaction, followed by a melting curve analysis. This multidimensional analysis entailed the use of two HCV typing probes, one labeled with FAM, the other labeled with HEX. The reactions with these probes were run in separate reaction tubes, although the experiment can also be run with both probes in a single reaction tube. The probes used in this analysis were the AG0203A-FAM probe (labelled with FAM; SEQ ID NO: 10) and the AG0308K probe (labelled with HEX; SEQ ID NO: 54), provided in FIG. 6. The two fluorescence emission readings were measured in their respective FAM and HEX channels (in two different reaction tubes).

The hybridization reactions included in vitro transcribed RNA templates corresponding to the HCV types 1a, 5a or 6a, or alternatively, 3a or 4a. Concentrations of these templates ranged from 1,000 ($10^3$) to 1,000,000 ($10^6$) copies per reaction. Each different RNA template concentration was run in a separate hybridization reaction. Each of the RT-PCR/$T_m$/quantitation reactions included an HCV typing probe as well as the quantitation probe ST650AAFBHQ2. These closed-tube reactions were established essentially as follows:

| Component | Concentration |
|---|---|
| poly rA carrier | 9 µg/mL |
| Glycerol | 6.2% |
| DMSO | 7.5% |
| Tricine, pH 8.3 | 50 mM |
| KOAc | 100 mM |
| dATP | 300 µM each |
| dCTP | |
| dGTP | |
| dUTP | 550 µM |
| ST280ATBUA1 amplification primer SEQ ID NO: 58 | 0.1 µM (10 pmol/rx) |
| ST778AATBA1 amplification primer SEQ ID NO: 59 | 0.5 µM (50 pmol/rx) |
| ST650AAFBHQ2 TaqMan Quantitation Probe SEQ ID NO: 60 | 0.15 µM (15 pmol/rx) |
| AG0203A-FAM HCV Typing Probe SEQ ID NO: 10 or AG0308K (HEX) HCV Typing Probe SEQ ID NO: 54 | 0.15 µM |
| UNG nuclease | 10 U/reaction |
| ZO5 polymerase | 40 U/reaction |
| Mn(OAc)$_2$ | 3 mM |
| New Methylene Blue | 25 µg/mL |
| HCV TARGET RNA | $10^3$-$10^6$ copies |

Figure 26:
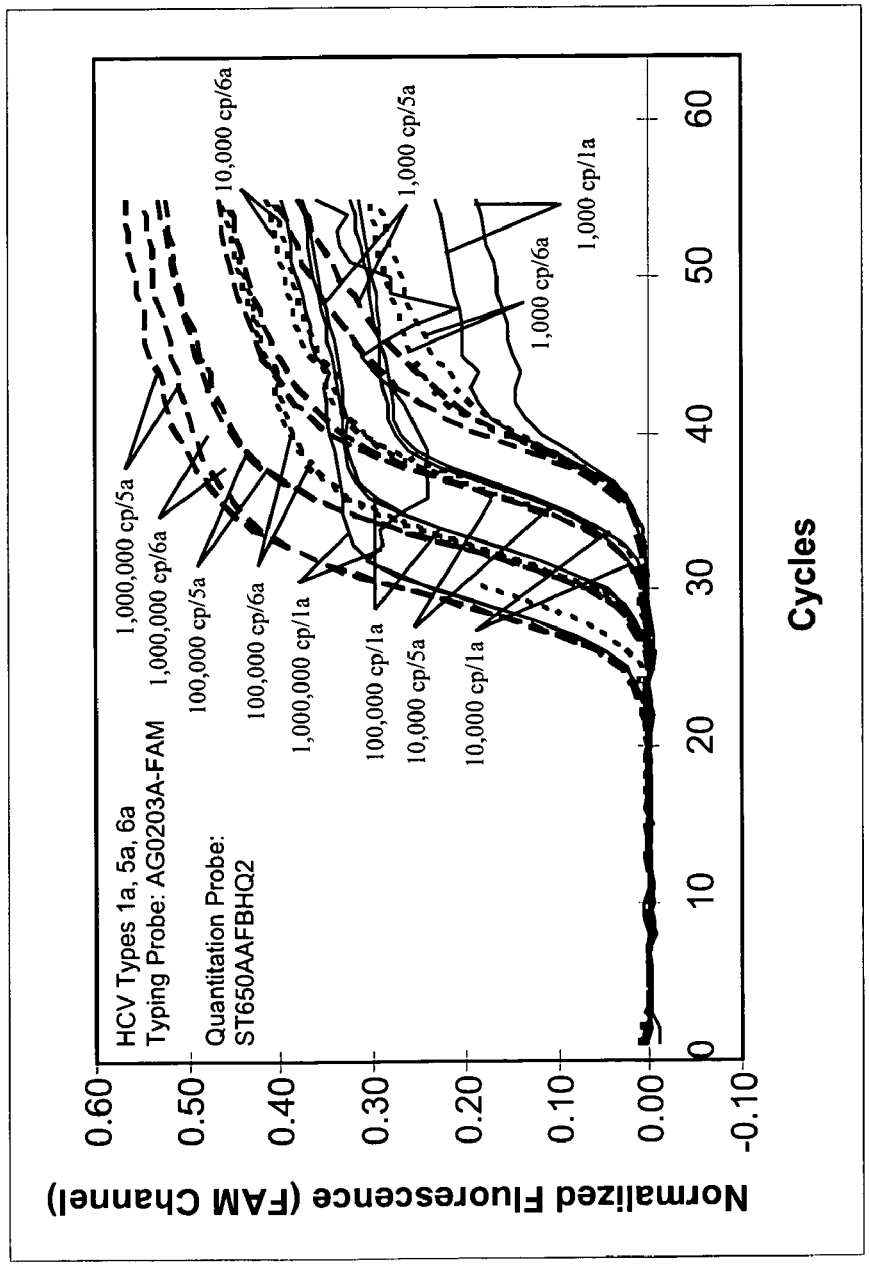
FIG. 26 provides a graph with the results of a closed-tube RT-PCR and HCV typing (melting curve) analysis that also incorporates HCV quantitation by use of a FAM-BHQ labeled TaqMan probe (ST650AAFBHQ2). The graph shows an overlay of normalized fluorescence increase as a function of cycle number during the PCR amplification phase of the thermocycling. HCV RNA transcripts from HCV types 1a, 5a and 6a were analyzed at 1000, 10,000, 100000, or 1,000,000 copies each (in duplicate). In addition to the quantitation probe, each reaction mix also contained the AG0203A-FAM probe for genotyping. The portion of the analysis shown in this figure only includes the RT-PCR amplification portion of the cycling program using only the FAM channel. Fluorescence data is displayed as a plot of normalized FAM fluorescence as a function of cycle number. The PCR amplification profiles for each HCV type and concentration are overlaid on the same graph. A representative set of data is shown. $C_T$ and viral quantitation are calculated from this portion of the fluorescence profile. A set of representative data is shown.
Figure 27:
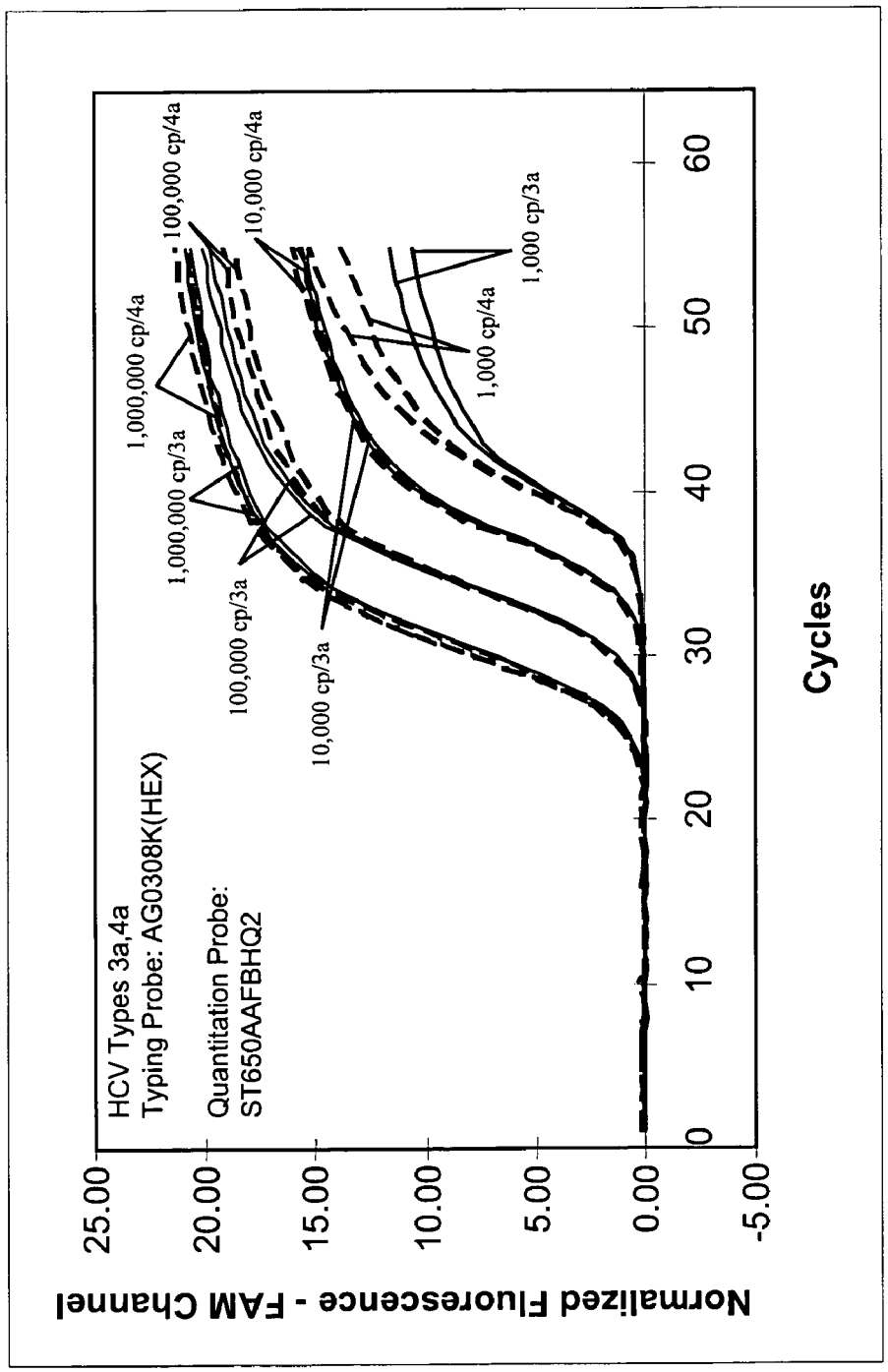
FIG. 27 provides a graph with the results of a closed-tube RT-PCR and HCV typing (melting curve) analysis that also incorporates HCV quantitation by use of a FAM-labeled TaqMan probe (ST650AAFBHQ2) using conditions similar to those described in FIG. 26. The RT-PCR reaction generated 5'-UTR amplicons from HCV types 3a and 4a. The amplicons were used at various concentrations, as shown. The reaction mix for the $T_m$ analysis comprised the AG0308K(HEX) probe. The portion of the analysis shown in this figure only includes the RT-PCR amplification portion of the cycling program using only the FAM channel. Fluorescence data is displayed as a plot of normalized HEX fluorescence as a function of cycle number. The PCR amplification profiles for each HCV type and concentration are overlaid on the same graph. A representative set of data is shown. $C_T$ and viral quantitation are calculated from this portion of the fluorescence profile. A set of representative data is shown.

ST650AAFBHQ2 TaqMan FCGGTGTACTCACCGQT- SEQ ID NO: 60
Quantitation Probe TCCGCAGACCACTATGP F = FAM; Q = BHQ-2; P = Terminal Phosphate Asymmetric RT-PCR reactions were run using the above reaction mix and with the thermal cycling conditions shown in FIG. 10. Fluorescence from the TaqMan quantitation probe was measured for 50 milliseconds during each PCR amplification cycle for 50 cycles at the 58° C. phase. The $C_T$ analysis is shown in FIGS. 26 and 27. The portion of the analysis shown in FIGS. 26 and 27 includes only the RT-PCR amplification portion of the cycling program using the FAM channel to detect the fluorescence from the cleaved TaqMan probe. Fluorescence data is displayed as a plot of normalized FAM fluorescence as a function of cycle number. The PCR amplification profiles for each HCV type and each concentration are overlaid on the same graph. Representative sets of data are shown.

FIGS. 26 and 27 illustrate that an HCV quantitation probe can be successfully incorporated into an HCV RT-PCR amplification and melting curve analysis to obtain viral load quantitative information using a closed-tube reaction system. Furthermore, the $C_T$ analysis shown here is able to distinguish the 1,000 fold variation in viral concentrations used in the reactions. This hold true for each of the HCV genotypes tested.

Figure 28:
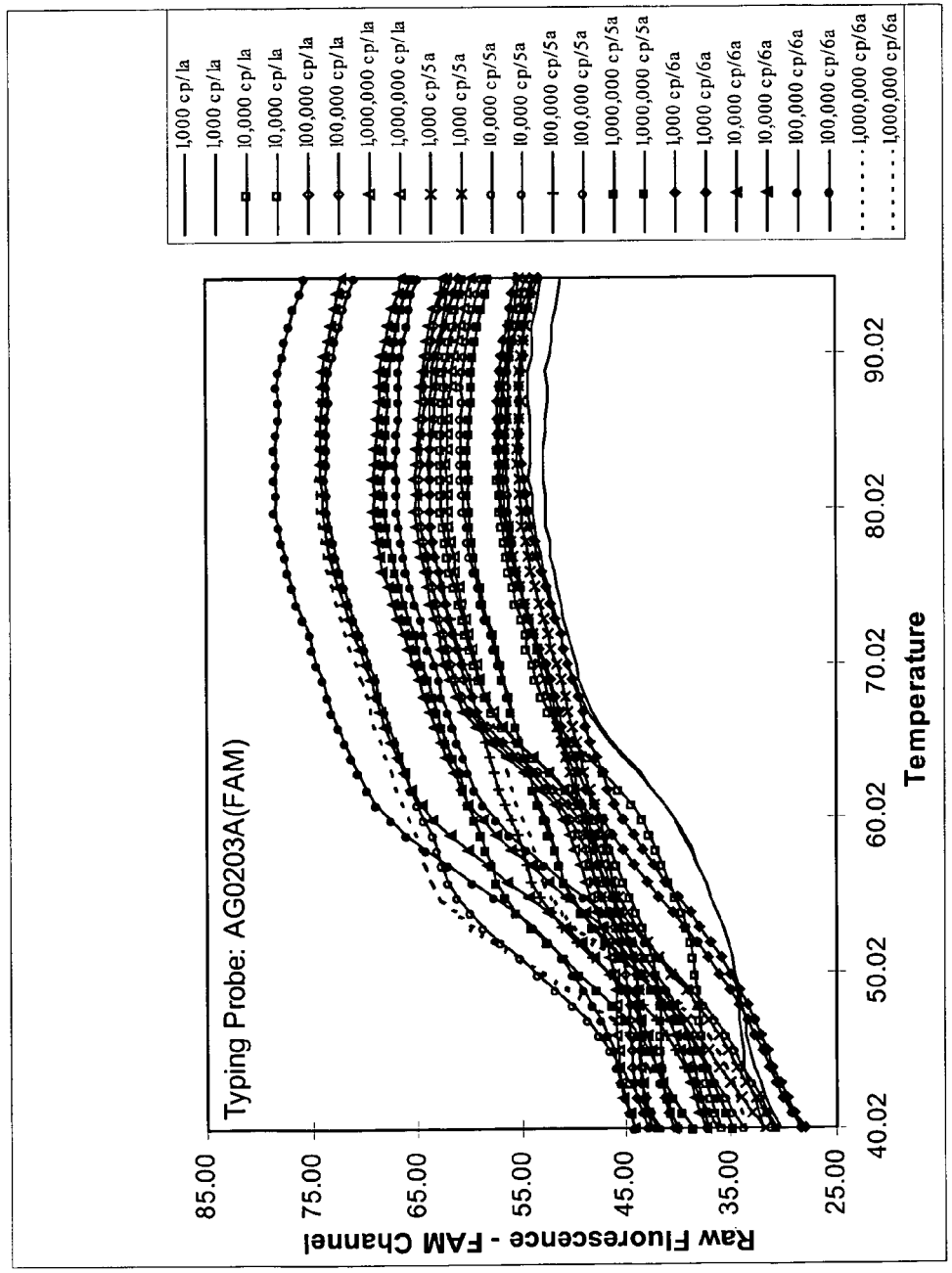
FIG. 28 provides a graph with results of the closed-tube, RT-PCR, HCV quantitation and HCV typing melting curve analysis from FIG. 26. The fluorescence data shown in this figure covers the HCV genotyping (melting curve) portion of the cycling program monitored on the FAM channel, corresponding to the AG0203A-FAM probe. The graph plots the melting curve raw FAM fluorescence data as a function of temperature. The melting curve profiles for each HCV type and concentration are overlaid on the same graph. A set of representative data is shown.

Following the RT-PCR amplification, this same reaction mix is used in the melting analysis. FIG. 28 shows the collected FAM fluorescence data from the melting analysis corresponding to the AG0203A-FAM probe (collected on the FAM channel) in a plot of raw fluorescence as a function of temperature. The results of multiple analyses (corresponding to each HCV type and at each concentration) were overlaid on the same plot. A set of representative data is shown.

Figure 29:
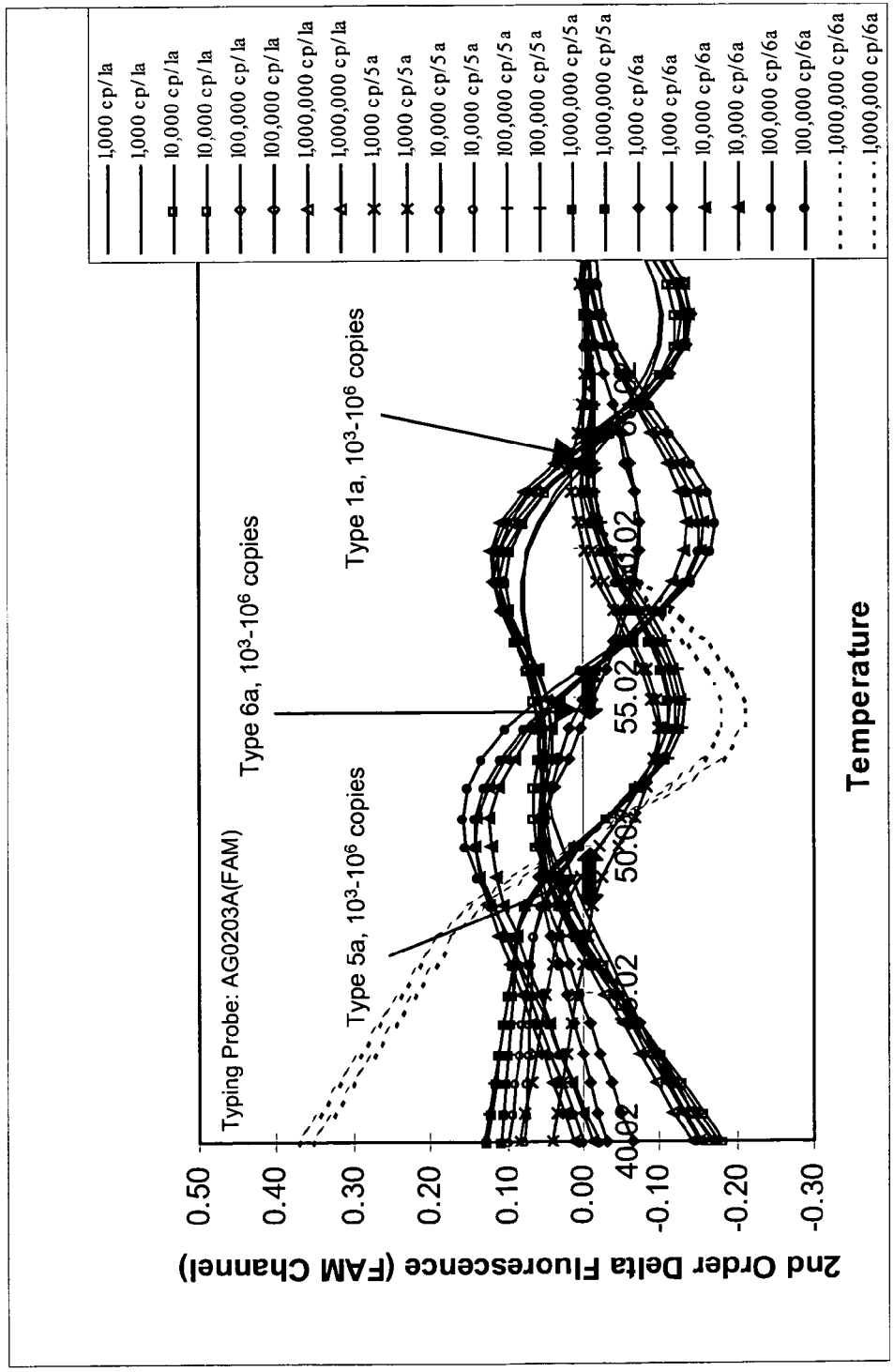
FIG. 29 provides a graph with results of the closed-tube, RT-PCR, HCV quantitation and HCV typing melting curve analysis from FIG. 28, displaying the same data using a second derivative plot. The graph plots the melting curve FAM fluorescence data second derivative as a function of temperature. The melting curve profiles for each HCV type and concentration are overlaid on the same graph. A set of representative data is shown.

The data in FIG. 28 can be more readily interpreted by using a second derivative plot of the same data. This second derivative plot is shown in FIG. 29. The intersection of each curve with the zero value on the Y-axis represents the $T_m$ of the hybridization complex at those particular hybridization conditions. As can be seen using the AG0203A-FAM probe, the $T_m$ for HCV types 1a, 5a and 6a can be easily distinguished on the graph.

Figure 30:
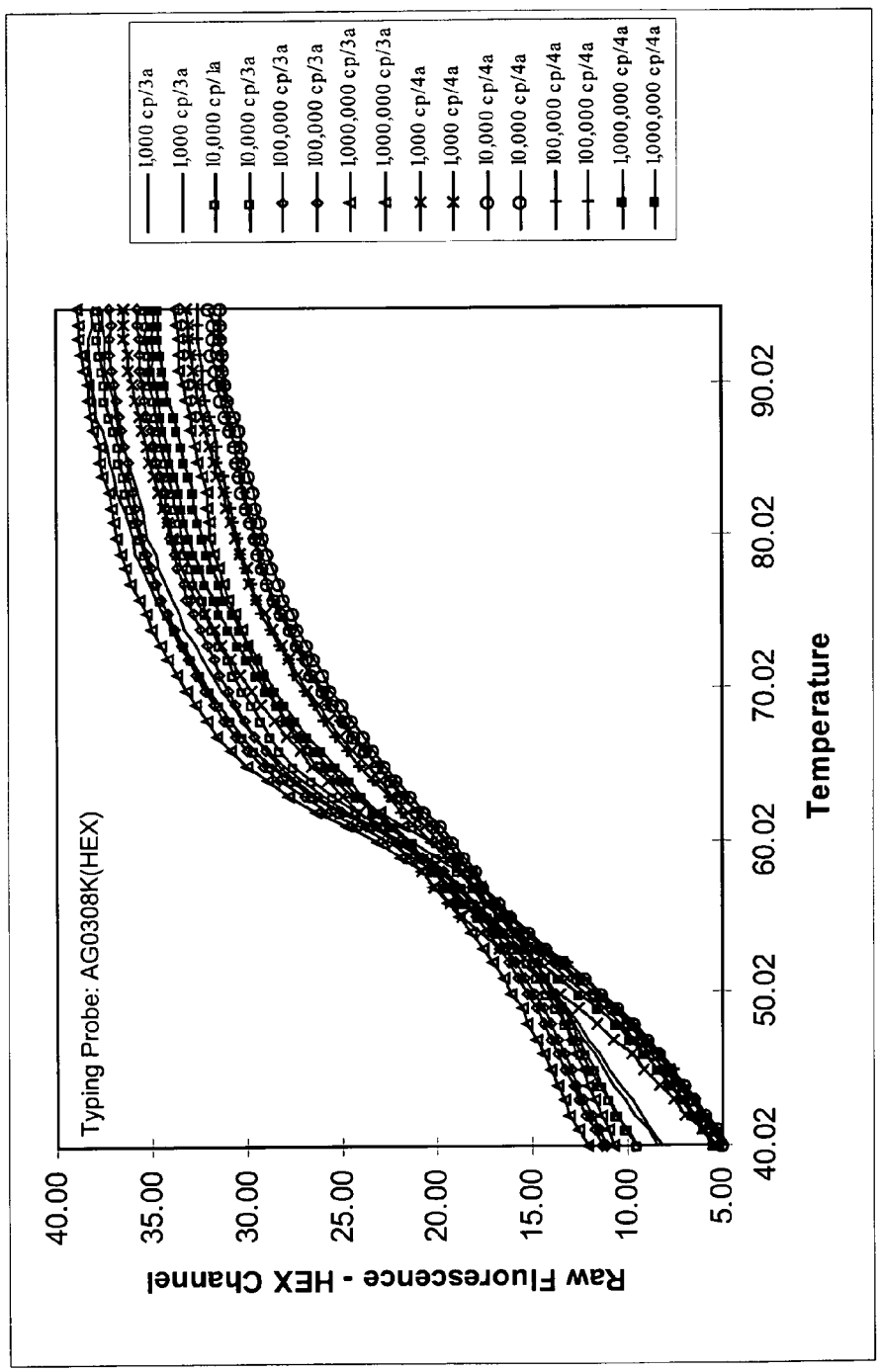
FIG. 30 provides a graph with results of the closed-tube, RT-PCR, HCV quantitation and HCV typing melting curve analysis from FIG. 27. The fluorescence data shown in this figure covers the HCV genotyping (melting curve) portion of the cycling program monitored on the HEX channel, corresponding to the AG0308K(HEX) probe. The graph plots the melting curve raw HEX fluorescence data as a function of temperature. The melting curve profiles for each HCV type and concentration are overlaid on the same graph. A set of representative data is shown.

Similarly, the fluorescence readings on the HEX channel during a melting curve analysis, corresponding to probe AG0308K, is shown graphically in FIG. 30 in a plot of raw fluorescence as a function of temperature. The results of multiple separate analyses (corresponding to each HCV type at each concentration) were overlaid on the same plot. A set of representative data is shown.

Figure 31:
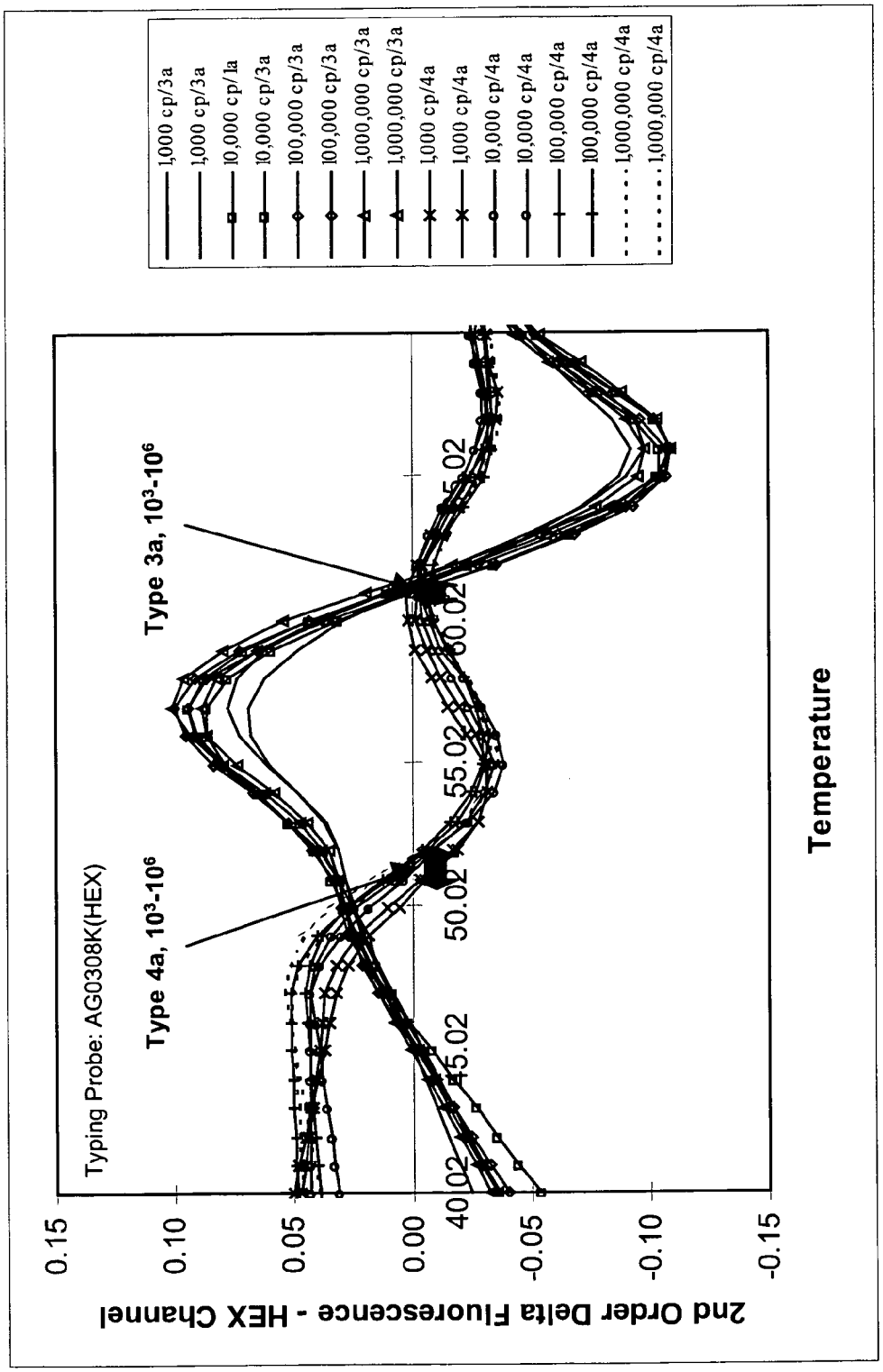
FIG. 31 provides a graph with results of the closed-tube, RT-PCR, HCV quantitation and HCV typing melting curve analysis from FIG. 30, displaying the same data using a second derivative plot. The graph plots the melting curve FAM fluorescence data second derivative as a function of temperature. The melting curve profiles for each HCV type and concentration are overlaid on the same graph. A set of representative data is shown.

The raw fluorescence data in FIG. 30 is also plotted as a second derivative plot, as shown in FIG. 31. The intersection of each curve with the zero value on the Y-axis represents the $T_m$ of the hybridization complex at those particular hybridization conditions. As can be seen in FIG. 31, using the AG0308K probe, the $T_m$ for HCV types 3a and 4a can be readily differentiated.

Thus, with the combined data from FIGS. 29 and 31, it is possible to make a definitive HCV typing assignment. Probe AG0203A (in the FAM channel) is able to assign an HCV sample to type 1a, 5a or 6a, where in contrast, probe AG0308K is able to make an HCV typing assignment to either type 3a or 4a using the HEX channel. Thus, these two data sets are complementary and provide enough information to make an HCV type assignment to types 1a, 3a, 4a, 5a or 6a.

As can be seen in this example, it is possible to combine multidimensional HCV typing analysis with HCV quantitation in a closed-tube reaction system, where all necessary reagents for the RT-PCR, quantitative (TaqMan) analysis and HCV typing (melting analysis) are included in one reaction mixture that does not require modification (e.g., purification steps or additional components). Progression of the HCV quantitation analysis and the HCV melting ($T_m$) analysis is regulated by the thermal cycling program.

Example 6

Nucleotide Sequences

This EXAMPLE provides nucleotide sequences used in the description of the present invention. The sequences provided in the TABLE below is meant to provide examples only, and it is not intended that the invention be limited in any way to the sequences provided in the TABLE below.

TABLE

| SEQ ID NO: | Description | SEQUENCE |
|---|---|---|
| 1 | HCV 5'-UTR consensus base sequence HCV Type 1a/1b/1c | TGAGTACACCGGAATTGCCAGGACGACCGGGTC |

TABLE-continued

| SEQ ID NO: | Description | SEQUENCE |
|---|---|---|
| 2 | HCV 5'-UTR consensus base sequence HCV Type 2a/2c | TGAGTACACCGGAATTGCCGGGAAGACTGGGTC |
| 3 | HCV 5'-UTR consensus base sequence HCV Type 2b | TGAGTACACCGGAATTACCGGAAAGACTGGGTC |
| 4 | HCV 5'-UTR consensus base sequence HCV Type 3a | TGAGTACACCGGAATCGCTGGGGTGACCGGGTC |
| 5 | HCV 5'-UTR consensus base sequence HCV Type 4a | TGAGTACACCGGAATCGCCGGGATGACCGGGTC |
| 6 | HCV 5'-UTR consensus base sequence HCV Type 5a | TGAGTACACCGGAATTGCCGGGATGACCGGGTC |
| 7 | HCV 5'-UTR consensus base sequence HCV Type 6a | TGAGTACACCGGAATTGCCAGGATGACCGGGTC |
| 8 | HCV 5'-UTR base sequence HCV Type 2a variant | TGAGTACACCGGAATTGCTGGGAAGACTGGGTC |
| 9 | HCV Typing Probe AG0203A | FCGGAATTGCCAGGACGACCGG |
| 10 | HCV Typing Probe AG0203A-FAM | FCGGAATTGCCAGGACGACCGGP |
| 11 | HCV Typing Probe AG0203A_HEX | HCGGAATTGCCAGGACGACCGGP |
| 12 | HCV Typing Probe AG0203A_JA | WCGGAATTGCCAGGACGACCGGP |
| 13 | HCV Typing Probe AG0203A_ET | WFCGGAATTGCCAGGACGACCGGP |
| 14 | HCV Typing Probe AG0303A | CGGAATTGCCAGGACGACCGG |
| 15 | HCV Typing Probe AG0303B | FJCGGAATTGCCAGGACGACCGG |
| 16 | HCV Typing Probe AG0403B | FVMMKKBBMVVKMMKVMKVVMMP |
| 17 | HCV Typing Probe AG0503A | FCCGGAATTGCCAGGACGACCGG |
| 18 | HCV Typing Probe AG0305B | FACCGGAATTGCCAGGACGACCGG |
| 19 | HCV Typing Probe AG0503D | FCACCGGAATTGCCAGGACGACCGG |
| 20 | HCV Typing Probe AG0503E | FCGGAATTGCCAGGACGACCGGG |
| 21 | HCV Typing Probe AG0503F | FCGGAATTGCCAGGACGACCGGGT |
| 22 | HCV Typing Probe AG0503G | FCGGAATTGCCAGGACGACCGGTC |
| 23 | HCV Typing Probe AG0503H | FCCGGAATTGCCAGGACGACCGGG |
| 24 | HCV Typing Probe AG0303A-SYBR | CGGAATTGCCAGGACGACCGG |
| 25 | HCV Typing Probe AG0307D | FDGGAASSGDDAGGADGADDGGP |
| 26 | HCV Typing Probe AG0307M | FCGGAATTGCCAGGACGACCGGGP |
| 27 | HCV Typing Probe AG0307N | FDGGAASSGDDAGGADGADDGGGP |
| 28 | HCV Typing Probe AG0308A | FDGGAASSGDDAGGADGADDGP |
| 29 | HCV Typing Probe AG0308B | FDGGAASSGDDAGGADGADDP |
| 30 | HCV Typing Probe AG0308F | FGTACACCGGAATTGCCAGGACGACCP |
| 31 | HCV Typing Probe AG0308L | FGTACACCGGAATTGCCAGGACGACP |
| 32 | HCV Typing Probe AG0308M | FGTACACCGGAATTGCCAGGACGAP |
| 33 | HCV Typing Probe AG0308N | FGTACACCGGAATTGCCAGGACGP |
| 34 | HCV Typing Probe AG0308P | FTACACCGGAATTGCCAGGACGACCP |
| 35 | HCV Typing Probe AG0308Q | FACACCGGAATTGCCAGGACGACCP |
| 36 | HCV Typing Probe AG0308R | FCACCGGAATTGCCAGGACGACCP |
| 37 | HCV Typing Probe AG0308S | FTACACCGGAATTGCCAGGACGACP |
| 38 | HCV Typing Probe AG0308T | FAGTACACCGGAATTGCCAGGACGACCP |
| 39 | HCV Typing Probe AG0308U | FGAGTACACCGGAATTGCCAGGACGACCP |
| 40 | HCV Typing Probe AG0308V | FTGAGTACACCGGAATTGCCAGGACGACCP |
| 41 | HCV Typing Probe AG0308W | FGTACACCGGAATTGCCAGGACGACCGP |
| 42 | HCV Typing Probe AG0308X | FGTACACCGGAATTGCCAGGACGACCGGP |
| 43 | HCV Typing Probe AG0308Y | FGTACACCGGAATTGCCAGGACGACCGGGP |
| 44 | HCV Typing Probe AG0308Z | FAGTACACCGGAATTGCCAGGACGACCGP |
| 45 | HCV Typing Probe AG0308AB | FAGTACACCGGAATTGCCAGGACGACP |

TABLE-continued

| SEQ ID NO: | Description | SEQUENCE |
|---|---|---|
| 46 | HCV Typing Probe AG0308AC | FGAGTACACCGGAATTGCCAGGACGAP |
| 47 | HCV Typing Probe AG0308AD | FTGAGTACACCGGAATTGCCAGGACGP |
| 48 | HCV Typing Probe AG0308C | FCGGAATTGCCAGGATGACCGGP |
| 49 | HCV Typing Probe AG0308D | FCGGAATTGCCGGGATGACCGGP |
| 50 | HCV Typing Probe AG0308E | FCGGAATTGCCGGGACGACCGGP |
| 51 | HCV Typing Probe AG0308H-FAM | FCGGAATCGCCGGGATGACCGGP |
| 52 | HCV Typing Probe AG0308H-HEX | HCGGAATCGCCGGGATGACCGGP |
| 53 | HCV Typing Probe AG0308J | HCGGAATTGCTGGGAAGACTGGP |
| 54 | HCV Typing Probe AG0308K | HCGGAATCGCTGGGGTGACTGGP |
| 55 | HCV Typing Probe AG0308G (FAM) | FCCCGCAAGACTGCTAGCCGAGP |
| 56 | HCV Typing Probe AG0308G (HEX) | HCCCGCAAGACTGCTAGCCGAGP |
| 57 | HCV Typing Probe AG0308AA | FTTCTTGGATCAACCCGCTCAATGCCTGGAGP |

TABLE-continued

| SEQ ID NO: | Description | SEQUENCE |
|---|---|---|
| 58 | HCV Amplification Primer ST280ATBUA1 | GCAGAAAGCGTCTAGCCATGGCGTTZ |
| 59 | HCV Amplification Primer ST778AATBA1 | GCAAGCACCCTATCAGGCAGTACCACAZ |
| 60 | HCV TaqMan Quantitation Probe ST650AAFBHQ2 | FCGGTGTACTCACCGQTTCCGCAGAC-CACTATGP |

F = 6-carboxy-fluorescein (FAM)
H = 2', 4, 4', 5', 7, 7'-hexachlorofluorescein (HEX)
W = JA270 rhodamine derivative (see, U.S. Pat. No. 6,184,379, issued Feb. 6, 2001, to Josel et al.)
P = 3'-terminal phosphate group/enzymatically blocked
J = acridine
S = 5-propynyl-dU
D = 5-Me-dC
B = 2'-O-methyl-U
K = 2'-O-methyl-rA
M = 2'-O-methyl-rG
V = 2'-O-methyl-rC
Q = BHQ-2
Z = N6-t-butylbenzyl-dA While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A closed-tube method for determining the type of a hepatitis C virus (HCV) in a sample, the method comprising:
   a) amplifying a portion of the HCV genome from the sample, thereby producing at least one amplicon;
   b) hybridizing the amplicon with at least a first probe and a second probe in a single hybridization reaction to form at least two target hybridization complexes, wherein:
      i) each probe has a nucleotide sequence that targets the probe to the same target region in the HCV genome and contains a minimum of six nucleotide overlap with the other probe, and is complementary or partially complementary to nucleotide sequences within the HCV genome;
      ii) the regions of hybridization complex complementarity or partial complementarity show sequence heterogeneity among at least two HCV types;
      iii) hybridization complexes comprising the first probe have a distinguishing range of melting temperature ($T_m$) that differentiates more than two HCV types but is indistinguishable for at least two other HCV types, wherein said range of melting temperature ($T_m$) is caused by sequence variations within a particular HCV type;
      iv) hybridization complexes comprising the second probe have a distinguishing range of melting temperature ($T_m$) that differentiates more than two HCV types but is indistinguishable for at least two other HCV types, wherein the more than two virus types differentiated by the first probe are different than the more than two HCV types differentiated by the second probe, wherein said range of melting temperature ($T_m$) is caused by sequence variations within a particular HCV type; and
      v) each probe comprises a different FRET donor moiety having a different excitation and emission spectra;
   c) simultaneously measuring the distinguishing range of melting temperature ($T_m$) of the target hybridization complexes; and,
   d) correlating the measured distinguishing range of melting temperature ($T_m$) of the target hybridization complexes with one of at least five HCV types, wherein an assignment of an HCV type is made based on the distinguishing range of melting temperature ($T_m$) of the hybridization complexes comprising the first probe and second probe in a multidimensional analysis.

2. The method of claim 1, wherein the HCV type is selected from genotypes 1, 2, 3, 4, 5 and 6.

3. The method of claim 1, wherein the HCV type is selected from any subtype of genotype 1, 2, 3, 4, 5 and 6.

4. The method of claim 1, wherein the HCV type is subtype 1a, 1b, 1c, 2a, 2b, 2c, 3a, 3b, 4a, 5a or 6a.

5. The method of claim 1, wherein the sample comprises human blood or human serum.

6. The method of claim 1, wherein the step of amplifying is by reverse transcription and polymerase chain reaction (RT-PCR).

7. The method of claim 6, wherein the PCR uses a primer pair comprising the nucleotide sequences of SEQ ID NOS: 58 and 59.

8. The method of claim 6, wherein the PCR uses primers that generate a PCR amplicon from a plurality of HCV types.

9. The method of claim 1, wherein:
   a) the hybridizing step further comprises at least one additional probe in addition to the first and second probes, to form a plurality of at least three target hybridization complexes;
   b) the plurality of hybridization complexes have a distinguishing range of melting temperature ($T_m$), wherein said range of melting temperature (T$_m$) is caused by sequence variations within a particular HCV type; and, c) the assignment of an HCV type in the correlating step is made based on the distinguishing range of melting temperature (T$_m$) of the plurality of at least three hybridization complexes.

10. The method of claim 1, wherein the nucleotide sequences of the at least first and second probes are complementary or partially complementary to nucleotide sequences within the 5'-UTR or the NS5 open reading frame of an HCV genome.

11. The method of claim 1, wherein the first and second probes comprise nucleotide sequences selected from SEQ ID NOS: 26 and 54.

12. The method of claim 1, wherein at least one probe comprises a FRET quencher moiety.

13. The method of claim 1, wherein the hybridizing step comprises admixing with a soluble FRET quencher.

14. The method of claim 13, wherein the soluble FRET quencher is a thiazine dye.

15. The method of claim 1, wherein the measuring step comprises detecting emitted light at more than one wavelength.

16. The method of claim 1, wherein at least one probe is a nucleotide oligomer comprising naturally occurring nucleotides, modified nucleotides, nucleotide analogs, one or more unnatural bases, unnatural internucleotide linkages, unnatural nucleotide backbones, or any combination thereof.

17. The method of claim 1, wherein the correlating step comprises comparing the distinguishing range of melting temperature (T$_m$) of the target hybridization complexes to the distinguishing range of melting temperature (T$_m$) of hybridization complexes comprising each probe and a plurality of HCV types.

18. The method of claim 1, wherein the method further is for determining the viral load of the HCV in the sample, wherein the amplifying step further comprises monitoring a rate of accumulation of the amplicon using reagents for real-time detection of amplicon accumulation and correlating the rate of amplicon accumulation with the viral load.

19. The method of claim 18, wherein the reagents for real-time detection of amplicon accumulation comprise an amplicon quantitation probe.

20. The method of claim 19, wherein the amplicon quantitation probe comprises a nucleotide sequence of SEQ ID NO: 60.

21. The method of claim 19, wherein the amplicon quantitation probe comprises a FRET donor moiety and a FRET quencher moiety wherein the amplicon quantitation probe forms a quantitation hybridization complex with the amplicon under conditions wherein base-pairing occurs.

22. The method of claim 21, wherein the amplifying step comprises detecting the donor moiety during the amplification step.

23. A closed-tube method for determining the type of a hepatitis C virus (HCV) in a sample, the method comprising:

a) hybridizing a nucleic acid derived from the HCV genome with at least a first probe and a second probe in a single hybridization reaction to form at least two target hybridization complexes, wherein:
   i) each probe has a nucleotide sequence that targets the probe to the same target region in an HCV genome and contains a minimum of six nucleotide overlap with the other probe, and is complementary or partially complementary to nucleotide sequences within the HCV genome;
   ii) the regions of hybridization complex complementarity or partial complementarity show sequence heterogeneity among at least two HCV types;
   iii) hybridization complexes comprising the first probe have a distinguishing range of melting temperature (T$_m$) that differentiates more than two HCV types but is indistinguishable for at least two other HCV types, wherein said range of melting temperature (T$_m$) is caused by sequence variations within a particular HCV type;
   iv) hybridization complexes comprising the second probe have a distinguishing range of melting temperature (T$_m$) that differentiates more than two HCV types but is indistinguishable for at least two other HCV types, wherein the more than two virus types differentiated by the first probe are different than the more than two HCV types differentiated by the second probe, wherein said range of melting temperature (T$_m$) is caused by sequence variations within a particular HCV type; and
   v) each probe comprises a different FRET donor moiety having a different excitation and emission spectra;
b) simultaneously measuring the distinguishing range of melting temperature (T$_m$) of the target hybridization complexes; and,
c) correlating the measured distinguishing range of melting temperature (T$_m$) of the target hybridization complexes with one of at least five HCV types, wherein an assignment of an HCV type is made based on the distinguishing range of melting temperature (T$_m$) of the hybridization complexes comprising the at least the first probe and second probe in a multidimensional analysis.

24. The method of claim 23, wherein the first and second probes comprise nucleotide sequences selected from SEQ ID NOS: 26 and 54.

25. The method of claim 1, wherein the first and second probes comprise nucleotide sequences independently selected from the nucleotide sequences provided in SEQ ID NOS: 9-57.

26. The method of claim 25, wherein the first and second probes comprise nucleotide sequences selected from SEQ ID NOS: 26 and 54, SED ID NOS: 10 and 53, and SEQ ID NOS: 57 and 52.

* * * * *